United States Patent [19]
Khodadoust

[11] Patent Number: 6,031,078
[45] Date of Patent: Feb. 29, 2000

[54] MTBX PROTEIN AND NUCLEIC ACID MOLECULES AND USES THEREFOR

[75] Inventor: Mehran Khodadoust, Chestnut Hill, Mass.

[73] Assignee: Millennium Pharmaceuticals, Inc., Cambridge, Mass.

[21] Appl. No.: 09/189,760

[22] Filed: Nov. 10, 1998

Related U.S. Application Data

[63] Continuation-in-part of application No. 09/163,116, Sep. 29, 1998, and a continuation-in-part of application No. 09/188,811, Nov. 9, 1998.
[60] Provisional application No. 60/089,467, Jun. 16, 1998.
[51] Int. Cl.[7] .................................................. C07K 14/00
[52] U.S. Cl. ........................................... 530/350; 530/300
[58] Field of Search ...................................... 530/350, 300

*Primary Examiner*—Karen Cochrane Carlson
*Attorney, Agent, or Firm*—Lahive & Cockfield, LLP; Amy E. Mandragouras, Esq.

[57] ABSTRACT

Novel MTbx polypeptides, proteins, and nucleic acid molecules are disclosed. In addition to isolated, full-length MTbx proteins, the invention further provides isolated MTbx fusion proteins, antigenic peptides and anti-MTbx antibodies. The invention also provides MTbx nucleic acid molecules, recombinant expression vectors containing a nucleic acid molecule of the invention, host cells into which the expression vectors have been introduced and non-human transgenic animals in which a MTbx gene has been introduced or disrupted. Diagnostic, screening and therapeutic methods utilizing compositions of the invention are also provided.

17 Claims, 29 Drawing Sheets

```
CATGGACAGCCTGAGCTCCGAGCGGTACTACCTCCAGTCCCCCGGTCCTCAGGGGTCGGAGCT
GGCTGCGCCCTGCTCACTCTTCCCGTACCAGGCGGCGGCTGGGGCGCCCCACGGACCTGTGTA
CCCGGCTCCTAACGGGGCGCGCTACCCCTACGGCTCCATGCTGCCCCCCGGCGGCTTCCCCGCG
GCTGTGTGCCCACCCGGGAGGGCGCAGTTCGGCCCAGGAGCCGGTGCGGGCAGTGGCGCGGG
CGGTAGCAGCGGCGGGGCGGCGGCCCGGGCCCTATCAAGTACAAGCCAGGGGGCTCCGCT
CTACGGGCCCGTACCCTGGAGCCCGCAGCGGCGGGATCTTGCGGAGGACTGGGGGGCCTGGG
GGTTCCAGGTTCTGGCTTCCGTGCCCACGTCTACCTGTGCAACCGGCCTCTGTGGCTCAAATTC
CACCGCCACCAAACTGAGATGATCATTACGAAACAGGGCAGGCGCATGTTTCCTTTCTTGAGC
TTCAACATAAACGGACTCAATCCCACTGCCCACTACAATGTGTTCGTAGAGGTGGTGCTGGCG
GACCCCAACCACTGGCGCTTCCAGGGGGGCAAATGGGTGACCTGTGGCAAAGCCGACAATAA
CATGCAGGGCAACAAAATGTATGTTCACCCAGAGTCTCCTAATACTGGTTCCCACTGGATGAG
ACAGGAGATTTCATTCGGGAAATTAAAACTCACCAATAACAAAGGCGCAAATAACAACAACA
CCCAGATGATAGTCTTACAATCCTTACACAAATACCAACCCCGACTGCATATTGTTGAAGTTAC
AGAGGATGGCGTGGAGGACTTGAATGAGCCCTCAAAGACCCAGACTTTTACCTTCTCAGAAAC
GCAATTCATTGCAGTGACTGCCTACCAAAACACCGATATTACTCAACTAAAGATTGATCATAA
CCCCTTTGCAAAAGGCTTCAGAGACAACTATGATTCCATGTACACCGCTTCAGAAAATGACAG
GTTAACTCCATCTCCCACGGATTCTCCTAGATCCCATCAGATTGTCCCTGGAGGTCGGTACGGC
GTTCAATCCTTCTTCCCGGAGCCCTTTGTCAACACTTTACCTCAAGCCCGCTATTATAATGGCG
AGAGAACCGTGCCACAGACCAACGGCCTCCTTTCACCCCAACAGAGCGAAGAGGTGGCCAAC
CCTCCCCAGCGGTGGCTTGTCACGCCTGTCCAGCAACCTGGGACCAACAAACTAGACATCAGT
TCCTATGAATCTGAATATACTTCTAGCACATTGCTCCCATATGGCATTAAATCCTTGCCCCTTC
AGACATCCCATGCCCTGGGGTATTACCCAGACCCAACCTTTCCTGCAATGGCAGGGTGGGGAG
GTCGAGGTTCTTACCAGAGGAAGATGGCAGCTGGACTACCATGGACCTCCAGAACAAGCCCCA
CTGTGTTCTCTGAAGATCAGCTCTCCAAGGAGAAAGTGAAAGAGGAAATTGGCTCTTCTTGGA
TAGAGACACCCCCTTCCATCAAATCTCTAGATTCCAATGATTCAGGAGTATACACCAGTGCTTG
TAAGCGAAGGCGGCTGTCTCCTAGCAACTCCAGTAATGAAAATTCACCCTCCATAAAGTGTGA
GGACATTAATGCTGAAGAGTATAGTAAAGACACCTCAAAAGGCATGGGAGGGTATTATGCTTT
TTACACAACTCCCTAAAGAGTTATTTTAACCTCAAAAATTAGCTAACTTTTTGCAGATGGACTT
GGTGGTGTTTTTGTTGTCTTCTTTGCCTAGGTKGCCAAAAAGAWGTTKGCCTTCCACCTTGAT
GCWTCCTGKTTKGTGCAATTCTCTAAAAGAAGGTGCCAAAGCTTTTTGATTGCTGCAGGTAAC
TGAAACAAACCTAGCATTTTTWAAAAATTARGATTAATGGAAGCCTTTAAGGATTTTAAATTC
GAAGGGATCCAAGGTTCTGTATTTATCTTATTGGGGAGACACTAACMMTTCAAAGAAGCAGG
CTGTGAACATTGGGTGCCCAGTGCTATCAGATGAGTTAAAACCTTTGATTCTCATTTCTATTTG
TAAATTCTTAAGCAAATAGAAGCCGAGTGTTAAGGTGTTTTGCTTCTGAAAGAGGGCTGTGCC
TTCCGTTTCAGAAGGAGACATTTTGCTGTTACATTCTGCCAGGGGCAAAAGATACTAGGCCCA
GGAGTCAAGAAAAGCTTTTGTGAAAGTGATAGTTTCACCTGACTTTGATTCCTTAACCCCCGGC
TTTTGGAACAAGCCATGTTTGCCCTAGTCCAGGATTGCCTCACTTGAGACTTGCTAGGCCTCTG
CTGTGTGCTGGGGTGGCCAGTGGGACTCAGGAGAGAGCAAGCTAAGGAGTCACCAAAAAAAA
AAAAAAAAAAAAGGGAGAATTTAAAAGTGTACAGTTGTGTGTTTAGATACACTATAGAATAA
TGTGGTATATATTGTACAAATAGTCTACAGGGTGT
```

Fig. 1

MLPPGGFPAAVCPPGRAQFGPCAGAGSGAGGSSGGGGGPGTYQYSQGAPLYGP
YPGAAAAGSCGGLGGLGVPGSGFRAHVYLCNRPLWLKFHRHQTEMIITKQGRR
MFPFLSFNINGLNPTAHYNVFVEVVLADPNHWRFQGGKWVTCGKADNNMQGN
KMYVHPESPNTGSHWMRQEISFGKLKLTNNKGANNNNTQMIVLQSLHKYQPRL
HIVEVTEDGVEDLNEPSKTQTFTFSETQFIAVTAYQNTDITQLKIDHNPFAKGFRD
NYDSMYTASENDRLTPSPTDSPRSHQIVPGGRYGVQSFFPEPFVNTLPQARYYNG
ERTVPQTNGLLSPQQSEEVANPPQRWLVTPVQQPGTNKLDISSYESEYTSSTLLPY
GIKSLPLQTSHALGYYPDPTFPAMAGWGGRGSYQRKMAAGLPWTSRTSPTVFSE
DQLSKEKVKEEIGSSWIETPPSIKSLDSNDSGVYTSACKRRRLSPSNSSNENSPSIK
CEDINAEEYSKDTSKGMGGYYAFYTTPN

Fig. 2

ALIGN calculates a global alignment of two sequences
version 2.0uPlease cite: Myers and Miller, CABIOS (1989)
> m154 protein                                                517 aa vs.
> SwissProt p79944 - EOMESODERMIN.                            692 aa
scoring matrix: pam120.mat, gap penalties: -12/-4
57.6% identity;          Global alignment score: 1419

```
                                                        10
inputs  MLP-------------------------------PGGF-------PAAVCPPG
        :.:                               : :        ..:: .:.
        MVPGAWHSLLFTTSSASEKEENRSQRMQLGEQLLNSSTPNLPHTFYFLTGDPSSAVHSPS
                10        20        30        40        50        60

20              30
inputs  -------RAQ----FGPGAGAG------SGAGGSS------GGG-------------GGP
           ..:    ...:..  :         ::.::     : :              :.:
        LEFSVGHKGQQHKKYSSGSSRGLQLDSPREAGSSSTMLSETGEGFSVAKTLPDNVRKGSP
                70        80        90       100       110       120

40                                     50
inputs  GT-------------Y----------QY---SQGAPL-------------YGP----
        ..              :          .:   .:: .:               :.:
        SAEEELNTAVPTSAPRYLDGSLQAASERYYLQPQGQQLQQTTTELGSPCSIFPYAPPQHS
               130       140       150       160       170       180

60
inputs  --YPGAAAA-----------------------------------------GSCGGL
        ::...::                                           :. .::
        AVYPAGGAARYPPYGSMLPPAGFSPPVCPSRPQYSSGYQYSQAPGTMYSPYPPAGTGSGL
               190       200       210       220       230       240

70        80        90       100       110       120
inputs  GGLGVPGSG--FRAHVYLCNRPLWLKFHRHQTEMIITKQGRRMFPFLSFNINGLNPTAHY
        ..::.::.:   ::..:::::::::::::::::::::::::::::::::.::::::::
        SALGLPGGGAGVRAQVFLCNRPLWLKFHRHQTEMIITKQGRRMFPFLSFNITGLNPTAHY
               250       260       270       280       290       300

130       140       150       160       170       180
inputs  NVFVEVVLADPNHWRFQGGKWVTCGKADNNMQGNKMYVHPESPNTGSHWMRQEISFGKLK
        ::::::::::::::::::::::::::::::::::.::::::::::.::::::::::::
        NVFVEVVLADPNHWRFQGGKWVTCGKADNNMQGNKVYVHPESPNTGAHWMRQEISFGKLK
               310       320       330       340       350       360

190       200       210       220       230       240
inputs  LTNNKGANNNNTQMIVLQSLHKYQPRLHIVEVTEDGVEDLNEPSKTQTFTFSETQFIAVT
        :::::::::::.::::::::::::::::::::.:::::::::....::::::..:::::
        LTNNKGANNNSTQMIVLQSLHKYQPRLHIVEVSEDGVEDLNDSAKNQTFTFPENQFIAVT
               370       380       390       400       410       420
```

Fig. 3-1

```
         250        260        270        280        290        300
inputs AYQNTDITQLKIDHNPFAKGFRDNYDSMYTASENDRLTPSPTDSPRSHQIVPGGRYGVQS
       ::::::::::::::::::::::::::::::::::::.::::::::.:::::::::: ::.::.
       AYQNTDITQLKIDHNPFAKGFRDNYDSMYTASESDRLTPSPADSPRSHQIVPGTRYSVQP
         430        440        450        460        470        480

310        320        330        340        350        360
inputs FFPEPFVNTLPQARYYNGERTVPQTNGLLSPQQSEEVAN-PPQRWLVTPVQQPGTNKLDI
       ::...:::.::.::::.::::::::.::::::: .::::: :::::..::::::...::::.
       FFQDQFVNNLPPARYYSGERTVPQANGLLSPQTNEEVANVPPQRWFVTPVQQAAANKLDM
         490        500        510        520        530        540

370        380        390        400        410        420
inputs SSYESEYTSSTLLPYGIKSLPLQTSHALGYYPDPTFPAMAGWGGRGS-YQRKMAAGLPWT
       ..:..:.....:: :::::::::.::::...::::...:.::::::.::: :::::...:::.
       GAYETDYSSGSLLTYGIKSLPIQTSHPMAYYPDAAFASMAGWGSRGSTYQRKMTTSLPWS
         550        560        570        580        590        600

430        440        450        460        470        480
inputs SRTSPTVFSEDQLSKEKVKEEIGSSWIETPPSIKSLDSNDSGVYTSACKRRRLSPSNSSN
       ::..::. :::: :..:::::..:::.:::::::::::::::::::::..:::::::::::.:::
       SRSSPSGFSEDLLPKDKVKEEMSSSWVETPPSIKSLDSNDSGVYTGACKRRRLSPSTSSN
         610        620        630        640        650        660

490        500        510
inputs ENSPSIKCEDINAEEYSKDTSKGMGGYYAFYTTPN
       ::::.::::::...:.: ::...::.: ::.::...
       ENSPPIKCEDIGTEDY-KDATKGLG-YYSFYSSS-
```

Fig. 3-2

ALIGN calculates a global alignment of two sequences
 version 2.0uPlease cite: Myers and Miller, CABIOS (1989)
> m154 protein                                          517 aa vs.
> SwissProt Q16650 - T-BRAIN-1 PROTEIN (T-BOX BRA  682aa
scoring matrix: pam120.mat, gap penalties: -12/-4
44.2% identity;         Global alignment score: 822

```
inputs  M-----LPP------------------GG-----------------------------
        :    :.:                   ::
        MQLEHCLSPSIMLSKKFLNVSSSYPHSGGSELVLHDHPIISTTDNLERSSPLKKITRGMT
                10        20        30        40        50        60

10        20                                      30
inputs  -------FPAAVCPPG---RAQFGP-------------GAGAG----------SGAGGS
        ::..  .::   :....:              :...:.             :.: ..
        NQSDTDNFPDSKDSPGDVQRSKLSPVLDGVSELRHSFDGSAADRYLLSQSSQPQSAATAP
                70        80        90        100       110       120

40        50        60        70
inputs  SG-----GGGGPGTYQYSQGAPL-YGPYPGAAAAGSCGGL----GGLGVPGSGF------
        :.     :  ::.  .: :.: : .  . ...:  ...:     . : : .:.
        SAMFPYPGQHGPAHPAFSIGSPSRYMAHHPVITNGAYNSLLSNSSPQGYPTAGYPYPQQY
                130       140       150       160       170       180

80        90        100       110
inputs  ----------------------RAHVYLCNRPLWLKFHRHQTEMIITKQGRRMFPFLSFN
                              .:.::::::::::::::::::::::::::::::::::
        GHSYQGAPFYQFSSTQPGLVPGKAQVYLCNRPLWLKFHRHQTEMIITKQGRRMFPFLSFN
                190       200       210       220       230       240

120       130       140       150       160       170
inputs  INGLNPTAHYNVFVEVVLADPNHWRFQGGKWVTCGKADNNMQGNKMYVHPESPNTGSHWM
        :.::.:::::::.::.:.:::::::::::::::::: ::::::.:.::..:.::::::.:::
        ISGLDPTAHYNIFVDVILADPNHWRFQGGKWVPCGKADTNVQGNRVYMHPDSPNTGAHWM
                250       260       270       280       290       300

180       190       200       210       220       230
inputs  RQEISFGKLKLTNNKGANNNNTQMIVLQSLHKYQPRLHIVEVTEDGVEDLNEPSKTQTFT
        :::::::::::::::::::.:::  ::..:::::::::::::.:::.:::  ..:...::::
        RQEISFGKLKLTNNKGASNNNGQMVVLQSLHKYQPRLHVVEVNEDGTEDTSQPGRVQTFT
                310       320       330       340       350       360

240       250       260       270       280       290
inputs  FSETQFIAVTAYQNTDITQLKIDHNPFAKGFRDNYDSMYTASENDRLTPSPTDSPRSHQI
        :.:::::::::::::::::::::::::::::::::::..::. . :::::::.::::: ::
        FPETQFIAVTAYQNTDITQLKIDHNPFAKGFRDNYDTIYTGCDMDRLTPSPNDSPRS-QI
                370       380       390       400       410
```

Fig. 4-1

```
         300        310        320                   330        340
inputs VPGGRYGVQ-SFFPEPFVNTLPQARYYNG---------ERTVPQTNGLLSPQQSEEVANP
       :::.::..  ::....::..  ..::.  :        .:.::.::::::::::.:. ..:
       VPGARYAMAGSFLQDQFVSNYAKARFHPGAGAGPGPGTDRSVPHTNGLLSPQQAEDPGAP
      420        430        440        450        460        470

350        360        370        380        390
inputs -PQRWLVTPVQQPGTNKLDISSYESEYTSS--TLLPY---GIKSLPLQ----TSHALGYY
       ::::.:::...  . .......  ::::.:  :.:.::::     :,...::::
       SPQRWFVTPANNRLDFAASAYDTATDFAGNAATLLSYAAAGVKALPLQAAGCTGRPLGYY
      480        490        500        510        520        530

400        410        420        430
inputs PDPT---------F------PAMAGWGGRGSYQRKMAAGLPWTSRTSPTVFSE-DQLS--
       .::.     .    .... :  . ..   .:::.. :  .   . .: ..:.
       ADPSGWGARSPPQYCGTKSGSVLPCWPNSAAAAARMAGANPYLGEEAEGLAAERSPLPPG
      540        550        560        570        580        590

440        450        460        470        480        490
inputs ---KEKVKEEIGSSWIETPPSIKSLDSNDSGVYTSACKRRRLSPSNSS-NENSPSIKCED
       .: :.  .::::::::.::::.::.:::.:  :  ::::.::.... .:.:...: :
       AAEDAKPKDLSDSSWIETPSSIKSIDSSDSGIYEQA-KRRRISPADTPVSESSSPLKSEV
      600        610        620        630        640        650

500        510
inputs INAEEYSKDTSKGMGGYYAFYTTPN
       .. .  :.  .:....:::.::. .
       LAQRDCEKNCAKDISGYYGFYS-HS
      660        670        680
```

Fig. 4-2

ALIGN calculates a global alignment of two sequences
 version 2.0uPlease cite: Myers and Miller, CABIOS (1989)
> SwissProt q64336 - T-BRAIN-1 PROTEIN (T-BOX BRA    681 aa vs.
> m154 protein                                      517 aa
scoring matrix: pam120.mat, gap penalties: -12/-4
43.9% identity;        Global alignment score: 830

```
                    10        20        30        40        50        60
inputs   MQLEHCLSPSIMLSKKFLNVSSSYPHSGGSELVLHDHPIISTTDNLERSSPLEKITRGMT
         :   :.:                      ::
         M-----LPP------------------GG-----------------------------

70        80        90       100       110       120
inputs   NQSDTDNFPDSKDSPGDVQRSKLSPVLDGVSELRHSFDGSAADRYLLSQSSQPQSAATAP
         ::..  .::    :....:              :...:.   : ... ... .:
         -------FPAAVCPPG---RAQFGP------------GAGAG----SGAGGSSGGGGGP
                10        20                                30

130       140       150       160       170       180
inputs   SAMFPYPSQHGPAHPAFSIGSPSRYMAHHPVITNGAYNSLLSNSSPQGYPTAGYPYPQQY
         .. ..:  ::  .:    ...  ....            :. ..:  .  : : .:.
         GT-YQY-SQGAPLYGPYPGAAAA-----------GSCGGL----GGLGVPGSGF------
         40        50        60                      70

190       200       210       220       230       240
inputs   GHSYQGAPFYQFSSTQPGLVPGKAQVYLCNRPLWLKFHRHQTEMIITKQGRRMFPFLSFN
                                 .:.:::::::::::::::::::::::::::::::::
         ----------------------RAHVYLCNRPLWLKFHRHQTEMIITKQGRRMFPFLSFN
                                80        90       100       110

250       260       270       280       290       300
inputs   ISGLDPTAHYNIFVDVILADPNHWRFQGGKWVPCGKADTNVQGNRVYMHPDSPNTGAHWM
         :.::.::::::.:.:.:::::::::::::::::  :::::..:::.:.::::::::.:::
         INGLNPTAHYNVFVEVVLADPNHWRFQGGKWVTCGKADNNMQGNKMYVHPESPNTGSHWM
         120       130       140       150       160       170

310       320       330       340       350       360
inputs   RQEISFGKLKLTNNKGASNNNGQMVVLQSLHKYQPRLHVVEVNEDGTEDTSQPGRVQTFT
         ::::::::::::::::::.:::  ::..:::::::::::::::.:::..:...:.::::
         RQEISFGKLKLTNNKGANNNNTQMIVLQSLHKYQPRLHIVEVTEDGVEDLNEPSKTQTFT
         180       190       200       210       220       230

370       380       390       400       410
inputs   FPETQFIAVTAYQNTDITQLKIDHNPFAKGFRDNYDTIYTGCDMDRLTPSPNDSPRS-QI
         :.::::::::::::::::::::::::::::::::::..::.  . ::::::::.::::: ::
         FSETQFIAVTAYQNTDITQLKIDHNPFAKGFRDNYDSMYTASENDRLTPSPTDSPRSHQI
         240       250       260       270       280       290
```

Fig. 5-1

```
         420       430       440       450       460       470
inputs VPGARYAMAGSFLQDQFVSNYAKARFHPGAGAGPGPGTDRSVPHTNGLLSPQQAEDPGAP
       :::.::..  ::.....:..  ..::.    :         .:.::.::::::::.:. ..:
       VPGGRYGVQ-SFFPEPFVNTLPQARYYNG---------ERTVPQTNGLLSPQQSEEVANP
            300       310       320                 330       340

480       490       500       510       520       530
inputs SPQRWFVTPANNRLDFAASAYDTATDFAGNAATLLSYAAAGVKALPLQAAGCTGRPLGYY
       :::::.:::...      . .......    .::::.:    :.:.::::     :....::::
       -PQRWLVTPVQQPGTNKLDISSYESEYTS--STLLPY---GIKSLPLQ----TSHALGYY
             350       360       370          380            390

540       550       560       570       580       590
inputs ADPSGWGARSPPQYCGAKSGSVLPCWPNSAAAAARMAGANPYLGEEAEGLAAERSPLAPA
       .::.        .    . ..   ....  . ..    .::..  :    ..:  ..:.
       PDPT---------F------PAMAGWGGRGSYQRKMAAGLPWTSRTSPTVFSE-DQLS--
                                  400       410       420       430

600       610       620       630       640       650
inputs AEDAKPKDLSDSSWIETPSSIKSIDSSDSGIYEQA-KRRRISPADTPVSESSSPLKSEVL
       .: :.    .::::::::.::::.::.:.::::.:   :  ::::..::....  .:.:....: :  .
       --KEKVKEEIGSSWIETPPSIKSLDSNDSGVYTSACKRRRLSPSNSS-NENSPSIKCEDI
            440       450       460       470       480       490

660       670       680
inputs AQRDCEKNCAKDIGGYYGFYS-HS
        .   .  :.  .:...:::::.::.   .
        NAEEYSKDTSKGMGGYYAFYTTPN
              500       510
```

Fig. 5-2

```
ALIGN calculates a global alignment of two sequences
 version 2.0uPlease cite: Myers and Miller, CABIOS (1989)
> Genbank U75996 - Xenopus laevis eomesodermin mR    2900 aa vs.
> M154                                               2491 aa
scoring matrix: pam120.mat, gap penalties: -12/4
53.9% identity;        Global alignment score: 4643

10        20        30        40        50        60
inputs  CCCGGCGCACACAGAGGAGGCTGGTGCATGTGGGAGCTTTCTCCATTCATGTGCAGACAC
         ::    ::::        :  ::.:            ::::         :.::
        CATGG-----ACAG------------CCTGAG--------CTCC------GAGC------
                            10                  20

70        80        90       100       110
inputs  CTATGGAACACGTCCCTCACTGACAGCCTATATCTCCTATGACTCAGTCCCCCC-TCCCC
           ::.::   : ::::                              :::::::::: ::: :
        ----GGTAC---TACCTC------------------------CAGTCCCCCGGTCCTC
                30                                        40        50

120       130       140       150       160       170
inputs  GTGTGTAAGTGAAGCCCCGCAGTGCATGGTGCCTGGCGCCTGGCACTCCCTATTATTTAC
         . : ::           :..:.:: :::  ::: ::::  ::.:.:          .:
        AGGGGT------------CGGAGC-TGG---CTG-CGCCCTGCTCAC----------TC
                             60             70        80

180       190       200       210       220       230
inputs  TACAAGTTCTGCTTCAGAAAAAGAAGAGAATCGCAGTCAGAGGATGCAGCTGGGAGAGCA
         :.: ::..:                         ::: :.:        :.::::::
        TTCCCGTAC---------------------CAGGCGG------CGGCTGGG------
                 90                                   100

240       250       260       270       280       290
inputs  GCTACTGAACAGCTCCACTCCTAACCTGCCCCACACCTTCTACCCTCTGACAGGCGACCC
          ::                       :::::::.            :::  : :. ::
        GC----------------------GCCCCACG-------------GACCTGTGTACC
                                    110                    120

300       310       320       330       340       350
inputs  CAGCAGTGCTGTCCATAGTCCCAGCTTGGAGTTTAGTGTGGGGCACAAGGGCCAACAGCA
         :..::         :::  :.:            ::::::.:.        :...:
        CGGC------------TCCTAAC--------------GGGGCGCG--------CTACC
          130                                    140                150

360       370       380       390       400       410
inputs  CAAGAAATACAGCAGCGGCAGCAGCAGGGGGCTCCAGTTAGACAGTCCCAGAGAAGCTGG
         :         :..::::          ::::      .:.: :::
        C-----------CTACGGC-------------TCCAT----GCTGCCCC----------
                        160                      170
```

Fig. 6-1

```
        420        430        440        450        460        470
inputs TTCCAGCAGCACAATGCTCAGCGAAACTGGAGAAGGTTTCTCGGTAGCCAAAACGTTACC
         ::..::.::                           :::      ::    ::     :
       --CCGGCGGC--------------------------TTC-------CC----CG----C
           180

480        490        500        510        520        530
inputs GGACAACGTGCGCAAAGGCTCCCCATCCGCAGAGGAGGAACTGAACACCGCGGTACCAAC
       ::  :..  ::::           :::  :::       :::::.             :::.::
       GG-CTGTGTGC-----------CCACCCG----GGAGGG---------CGCAGT------
         190                   200           210

540        550        560        570        580        590
inputs TTCAGCTCCTCGCTACCTGGACGGCAGCCTACAGGCGGCATCTGAGCGCTACTACCTACA
          ::..::           ::..:::  :  :..:   :.:.:::..:      ::  ::::
       -TCGGC---------CCAGGA-GCCGG--TGCGGGCAG----TG-GCGC-----------
         220              230             240

600        610        620        630        640        650
inputs GCCCCAGGGCCAACAGTTGCAGCAAACTACCACAGAGCTCGGCTCCCCATGTTCCATCTT
            :::      :..::..:::::..       :..:.:    ::::      :::. :
       ------GGG----CGGTAGCAGCGG-------CGGGG-GCGGCGGCCCGGG---------
             250        260              270          280

660        670        680        690        700        710
inputs CCCTTATGCGCCTCCACAGCACAGCGCCGTGTATCCTGCAGGAGGCGCCGCCAGGTACCC
       :..:::       .:::  :::::             ::::.:::   ::::
       --------CACCTA-TCAGTACAGC-------------CAGGGGGCTCCGC---------
                   290                      300        310

720        730        740        750        760        770
inputs ACCATACGGCAGCATGTTGCCCCCAGCCGGCTTCTCCCCTCCTGTGTGCCCATCCCGGCC
         .:   :::::                   ::::  :..:     ::::  :..:::
       TC--TACGG-----------------GCCG--TAC-----CCTG-GAGCC----------
                320                                  330

780        790        800        810        820        830
inputs TCAGTACTCCTCAGGCTACCAGTACAGCCAGGCCCCAGGGACCATGTATAGCCCATACCC
                              .::::   :::    ::::  :..::
       ----------------------GCAGC--GGC----GGGATCTTG--------------
                                340            350

840        850        860        870        880        890
inputs ACCCGCAGGTACTGGCAGTGGACTCAGTGCGCTTGGGCTGCCAGGCGGCGGTGCGGGAGT
           ::  :::  :::::       ::.:    ::  :::  :  :::::          :  :: :
       ---CGGAGG-ACTGG---GGGGC--------CTGGGGGTTCCAGG------TTCTGGCTT
          360              370                 380              390
```

Fig. 6-2

```
inputs TCGTGCCCAGGTCTTCCTCTGTAACCGGCCCCTCTGGCTGAAATTCCACCGGCACCAGAC
       ::::::::: ::::.::: :: :::::::: :: ::::: :::::::::::: :::::.::
       CCGTGCCCACGTCTACCTGTGCAACCGGCCTCTGTGGCTCAAATTCCACCGCCACCAAAC
                400       410       420       430       440       450

960       970       980       990      1000      1010
inputs TGAGATGATCATCACCAAGCAGGGCAGGAGGATGTTCCCTTTCCTCAGTTTCAACATCAC
       :::::::::::: :: ::.:::::::::: : ::::: :::::: : :: :::::::: :
       TGAGATGATCATTACGAAACAGGGCAGGCGCATGTTTCCTTTCTTGAGCTTCAACATAAA
                460       470       480       490       500       510

1020      1030      1040      1050      1060      1070
inputs TGGCCTGAACCCCACGGCCCATTACAATGTGTTTCTAGAGGTGGTTCTGGCCGACCCCAA
       :: :: :: ::::: ::::: :::::::::::: :::::::::::: ::::: :::::::
       CGGACTCAATCCCACTGCCCACTACAATGTGTTCGTAGAGGTGGTGCTGGCGGACCCCAA
                520       530       540       550       560       570

1080      1090      1100      1110      1120      1130
inputs CCACTGGCGCTTCCAAGGAGGCAAATGGGTGACTTGCGGCAAAGCGGACAACAATATGCA
       :::::::::::::::::.::.:::::::::::: :: :::::::: ::::: :: :::::
       CCACTGGCGCTTCCAGGGGGGCAAATGGGTGACCTGTGGCAAAGCCGACAATAACATGCA
                580       590       600       610       620       630

1140      1150      1160      1170      1180      1190
inputs AGGGAATAAGGTTTATGTGCACCCAGAATCTCCCAACACTGGAGCGCACTGGATGCGCCA
       .:: :: ::..: ::::: ::::::::.:::: :: :::::. : :::::::::: : ::
       GGGCAACAAAATGTATGTTCACCCAGAGTCTCCTAATACTGGTTCCCACTGGATGAGACA
                640       650       660       670       680       690

1200      1210      1220      1230      1240      1250
inputs AGAAATCTCCTTTGGGAAACTCAAACTCACCAACAACAAAGGCGCTAATAACAACAGCAC
       .:.:: :: :: :::::: : :::::::::.::::::::::::::::.:::::::::.::
       GGAGATTTCATTCGGGAAATTAAAACTCACCAATAACAAAGGCGCAAATAACAACAACAC
                700       710       720       730       740       750

1260      1270      1280      1290      1300      1310
inputs CCAGATGATCGTGCTCCAGTCTCTGCACAAGTACCAGCCGCGTCTGCACATAGTGGAAGT
       :::::::::: :: : :::.:: :.::::::.::::::.:: ::.::::: ::..:::::
       CCAGATGATAGTCTTACAATCCTTACACAAATACCAACCCCGACTGCATATTGTTGAAGT
                760       770       780       790       800       810

1320      1330      1340      1350      1360      1370
inputs GAGTGAGGATGGAGTGGAGGATCTGAACGACTCTGCTAAAAACCAGACCTTTACCTTCCC
       : ..:::::::::: :::::::::: :::: :: : :.::.: :::::: ::::::::: :
       TACAGAGGATGGCGTGGAGGACTTGAATGAGCCCTCAAAGACCCAGACTTTTACCTTCTC
                820       830       840       850       860       870
```

Fig. 6-3

```
        1380      1390      1400      1410      1420      1430
inputs GGAGAACCAGTTCATCGCAGTGACCGCCTACCAGAACACCGATATTACTCAGCTGAAGAT
       .::.:   ::.:::::  :::::::: :::::::.:::::::::::::::.::.:::::
       AGAAACGCAATTCATTGCAGTGACTGCCTACCAAAACACCGATATTACTCAACTAAAGAT
         880       890       900       910       920       930

1440      1450      1460      1470      1480      1490
inputs TGACCACAACCCATTCGCAAAAGGGTTCAGGGATAATTATGATTCCATGTACACAGCATC
       :::  :: :::::  ::  :::::::::: :::::.:: :: ::::::::::::::: ::.::
       TGATCATAACCCCTTTGCAAAAGGCTTCAGAGACAACTATGATTCCATGTACACCGCTTC
         940       950       960       970       980       990

1500      1510      1520      1530      1540      1550
inputs AGAAAGTGACAGATTAACGCCATCTCCTGCGGATTCTCCTAGATCTCACCAGATAGTCCC
       :::::.:::::::.::::: :::::::: .:::::::::::::: :: :::::.:::::
       AGAAAATGACAGGTTAACTCCATCTCCCACCCATTCTCCTAGATCCCATCAGATTGTCCC
         1000      1010      1020      1030      1040      1050

1560      1570      1580      1590      1600      1610
inputs TGGGACCCGATACAGTGTGCAGCCTTTCTTCCAGGACCAGTTTGTCAACAACCTGCCCCC
       :::..  ::.:::.: :: ::. : :::::::: ::: :  ::::::::::   :.:: :
       TGGAGGTCGGTACGGCGTTCAATCCTTCTTCCCGGAGCCCTTTGTCAACACTTTACCTCA
         1060      1070      1080      1090      1100      1110

1620      1630      1640      1650      1660      1670
inputs TGCCAGATACTACAGTGGGGAGAGGACTGTCCCCCAAGCAAATGGTCTCCTGTCCCCACA
       .::: : :: :: :..::: :::::::.:: :: ::  .: :: :: ::::: :: :: ::
       AGCCCGCTATTATAATGGCGAGAGAACCGTGCCACAGACCAACGGCCTCCTTTCACCCCA
         1120      1130      1140      1150      1160      1170

1680      1690      1700      1710      1720      1730
inputs GACTAATGAAGAAGTGGCAAATGTTCCTCCACAGAGGTGGTTTGTGACCCCCGTGCAACA
       .    :.. :::::.::::: ::       :::::  :::   :::::  :: :: :: ::.::
       ACAGAGCGAAGAGGTGGCCAA---CCCTCCCCAGCGGTGGCTTGTCACGCCTGTCCAGCA
         1180      1190      1200      1210      1220

1740      1750      1760      1770      1780      1790
inputs AGCTGCTGCAAATAAACTGGACATGGGGGCCTACGAAACAGACTACTCCTCAGGTTCCCT
       : :::  .: :: :::::.:::::  .:  :::: :::..:.:: :: .: :::..: .: :
       ACCTGGGACCAACAAACTAGACATCAGTTCCTATGAATCTGAATATACTTCTAGCACATT
         1230      1240      1250      1260      1270      1280

1800      1810      1820      1830      1840      1850
inputs CCTCACCTATGGCATTAAGTCTCTGCCCATCCAAACCTCCCA--CCCAATGGCCTACTAC
       ::: : ::::::::::::.::  ::::: : ::.:: ::::: :::.. :: :: :::
       GCTCCCATATGGCATTAAATCCTTGCCCCTTCAGACATCCCATGCCCTGGGG--TATTAC
         1290      1300      1310      1320      1330      1340

1860      1870      1880      1890      1900      1910
inputs CCAGATGCAGCCTTTGCCTCCATGGCAGGCTGGGGAAGCAGAGGTTCTACCTATCAGAGG
       :::::  ::..:::::  : : ::::::::  :::::::.: ::::::::. :   ::::::
       CCAGACCCAACCTTTCCTGCAATGGCAGGGTGGGGAGGTCGAGGTTCTTAC---CAGAGG
         1350      1360      1370      1380      1390      1400
```

Fig. 6-4

```
        1920       1930       1940       1950       1960       1970
inputs  AAAATGACAACAAGTTTACCTTGGTCCTCAAGGTCAAGTCCTTCAGGTTTCTCAGAAGAT
        ::..:::.::.:...  :::::.:::.:::  :::...::::  ::  .:.:  :::::.:::::
        AAGATGGCAGCTGGACTACCATGGACCTCCAGAACAAGCCCCACTGTGTTCTCTGAAGAT
            1410       1420       1430       1440       1450       1460

1980       1990       2000       2010       2020       2030
inputs  CTCCTACCTAAGGACAAGGTCAAGGAAGAGATGAGCTCTTCCTGGGTAGAAACCCCTCCC
        :.  ::   :  :::::  ::..::  ::..::.::.::   .::::::: :::.:::::.:: :: ::
        CAGCTCTCCAAGGAGAAAGTGAAAGAGGAAATTGGCTCTTCTTGGATAGAGACACCCCCT
            1470       1480       1490       1500       1510       1520

2040       2050       2060       2070       2080       2090
inputs  TCCATTAAATCACTAGACTCTAATGATTCAGGGGTGTATACGGGTGCATGTAAGAGAAGG
        :::::  :::::.::::  ::  :::::::::::.::.::  ::  .::::.:::::: :::::
        TCCATCAAATCTCTAGATTCCAATGATTCAGGAGTATACACCAGTGCTTGTAAGCAAGG
            1530       1540       1550       1560       1570       1580

2100       2110       2120       2130       2140       2150
inputs  AGGCTCTCCCCTAGCACCTCAAGCAATGAAAACTC-CCCTCCTATAAAATGTGAAGACAT
        ::::  ::  :::::::  :::  ::  :::::::::  ::  :::::: :::::.:::::.:::::
        CGGCTGTCTCCTAGCAACTCCAGTAATGAAAATTCACCCTCC-ATAAAGTGTGAGGACAT
            1590       1600       1610       1620       1630       1640

2160       2170       2180       2190       2200       2210
inputs  TGGCACTGAGGACTATAAAGATG---CCACTAAGGGACT---TGGGTATTACTCTTTCTA
        :...  .:::::.::  :::::...:.:    :::.:.::.::   :   .:::::::: :::: ::
        TAATGCTGAAGAGTATAGTAAAGACACCTCAAAAGGCATGGGAGGGTATTATGCTTTTTA
            1650       1660       1670       1680       1690       1700

2220       2230                  2240       2250
inputs  CTCTAGTTCTTAAAGAAAGGTT-----------AATATGCTGTATTAATATATA---ACT
        :..:.: : : :::::::.. .::           :::..:::..  ::...:. : :    :::
        CACAACTCCCTAAAGAGTTATTTTAACCTCAAAAATTAGCTAACTTTTTGCAGATGGACT
            1710       1720       1730       1740       1750       1760

2260                 2270       2280       2290       2300
inputs  TCGGGGA--------TGGAC--CATTG--TATAT-GCCAAAAAGTGGGTTTGCATTTCA-
        :  :  ::.          :  :.:   :.:::  ::  .:  :::::::::.  :  ::  ::  ::  ::
        TGGTGGTGTTTTTTGTTGTCTTCTTTGCCTAGGTKGCCAAAAAGAWG-TTKGCCTTCCAC
            1770       1780       1790       1800       1810       1820

2310       2320       2330       2340       2350
inputs  --TTTGGCGTCCTCACT-CAGCCATGAAAGTGTTAAAGCCTCAGTATTATTTTTATTTTT
        :  .  ::  ::::   :   .::  ::  .   .....:::   :  ..:  .::::  :::  :
        CTTGATGCWTCCTGKTTKGTGCAATTCTCTAAAAGAAGGTGCCAAAGCTTTTTGATTGCT
            1830       1840       1850       1860       1870       1880
```

Fig. 6-5

```
         2360      2370      2380      2390      2400      2410
inputs TCAGGAAA-TGGAATAAACTTGGCACTAAT-GAGCAAAACAAAACAGG------TTTTAT
       :::: .::  ::..::  ::::  :.:::  :..:  .::.  :...  .:...  : :           :::..:
       GCAGGTAACTGAAACAAACCTAGCATTTTTWAAAAATTARGATTAATGGAAGCCTTTAAG
         1890      1900      1910      1920      1930      1940

2420      2430      2440      2450      2460
inputs AAATATATATATATGTATATAGTTGTTATTATATATAT-TTATAAATGTATAAATA----
       .:: .::..::.  ... .  ::   ...:  :..  :.:::.:::   ::::-...  :....  :  ::
       GATTTTAAATTCGAAGGGATCCAAGGTTCTGTATTTATCTTATTGGGGAGACACTAACMM
         1950      1960      1970      1980      1990      2000

2470      2480      2490      2500      2510
inputs -TATATAATTATTATTATTATTATTATGTTTTATTTA-TGGCACAA-----AAAGCCAAT
        :  ..:..:.   . .  :..:  :.  :::.  ::     . :.  :.  :: :.        :::..:::..:
       TTCAAAGAAGCAGGCTGTGAACATTGGGTGCCCAGTGCTATCAGATGAGTTAAAACCTTT
         2010      2020      2030      2040      2050      2060

2520         2530      2540      2550      2560
inputs GTA---CATTT---ATTGTATATACACCTGCATATTGTGG---AGTAT-AAGATATTGT-
       :..    :::::    .:::::.::.:.   .:::..::.:..:    :::.: :::..:.:: :
       GATTCTCATTTCTATTTGTAAATTCTTAAGCAAATAGAAGCCGAGTGTTAAGGTGTTTTG
         2070      2080      2090      2100      2110      2120

2570      2580      2590      2600      2610
inputs ------ATAAATAGCAGCGTCT-CTGTTT-GGAAAGATGTACCTGACA-TTAAATGCA--
       :.:.:  .::.:  :  ::  : ::::  .:::.::  . :  : .:.  :::  ::  :.
       CTTCTGAAAGAGGGCTGTGCCTTCCGTTTCAGAAGGAGACATTTTGCTGTTACATTCTGC
         2130      2140      2150      2160      2170      2180

2620      2630      2640      2650      2660      2660
inputs CTGGTGGGTTGTATATTGTAT--TAGTGGCACACAGCTGTATATTTCTAGAGTTAGGTGG
       :.::  :  ....  :::  :.. .     ..::  ::  .  :.  :.::  :  :  ::.::.. :
       CAGGGGCAAAAGATACTAGGCCCAGGAGTCAAGAAAAGCTTTTGTGAAAGTGATAGTTTC
         2190      2200      2210      2220      2230      2240

2680      2690      2700      2710      2720      2730
inputs CAATGTCA--GATTGTATGTCCACTTTGTCTTGAAAGATTTCTATTTAAAACTTGTCTCT
       ::..:.   ::::    .:..::  :      :  :::::.:: :.    :..  ::..      ::.:::
       ACCTGACTTTGATTCCTTAACCCCCGGCTTTTGGAACAAGCCATGTTTGCCCTAGTCCAG
         2250      2260      2270      2280      2290      2300

2740      2750      2760      2770      2780
inputs TAAGGCAAATCTTGT-ACAAATGTAAAGTC--CAGTA--CTGAATGTTCCAGAGTGGGAC
       :.  ::  .  .:::::.  ::::...    ...    ::  :.::.    :::..   ::::   ::::::
       GATTGCCTCACTTGAGACTTGCTAGGCCTCTGCTGTGTGCTGGGGTGGCCAG--TGGGAC
         2310      2320      2330      2340      2350

2790      2800      2810      2820      2830
inputs GCAT-TGTGGGTTTACCTTGCTTTC--CTTTTTGTTATGTCATGTATA------TATTGC
       ::    ..:::.:    ...: ..     ::   :.............:              ...:.
       TCAGGAGAGAGCAAGCTAAGGAGTCACCAAAAAAAAAAAAAAAAAAAAGGGAGAATTTAA
         2360      2370      2380      2390      2400      2410
```

Fig. 6-6

```
        2840      2850      2860      2870      2880      2890
inputs TGGCAATTTTTAATAAATGTGGTGCCTCTTGGGAAATCCAAAAAAAAAAAAAAAAAAAAAA
        ..:  ... . :..:...: :.:.  :.::. .:::..  .....:.:.....: :::.:
       AAGTGTACAGTTGTGTGTTTAGATACACTATAGAATAATGTGGTATATATTGTACAAATA
        2420      2430      2440      2450      2460      2470

2900
inputs A------------

GTCTACAGGGTGT
        2480      2490
```

Fig. 6-7

```
ALIGN calculates a global alignment of two sequences
 version 2.0uPlease cite: Myers and Miller, CABIOS (1989)
> Genbank U49250 - Human putative cerebral cortex 2894 aa vs.
> M154                                                  2491 aa
scoring matrix: pam120.mat, gap penalties: -12/-4
49.7% identity;         Global alignment score: 4192

10        20        30        40        50        60
inputs  GGCGAGTGTTCAGGTTCTAGAGCTATGCAGCTGGAGCACTGCCTTTCTCCTTCTATCATG
          .::  .:::    : .:::::  : ::: : :   ::   ::. :: ::  : .::
        --C--ATGGACAG---CCTGAGCTCCG-AGCGGTACTACCTCCAGTCCCC--CGGTC---
                      10        20        30        40

70        80        90       100       110       120
inputs  CTCTCCAAGAAATTTCTCAATGTGAGCAGCAGCTACCCACATTCAGGCGGATCCGAGCTT
        :::  ..:.      ::.    ::::.: :::.:         ::       ::
        --CTCAGGGG------TCG----GAGCTG--GCTGC----------GC----CC------
                 50               60                        70

130       140       150       160       170       180
inputs  GTCTTGCACGATCATCCCATTATCTCGACCACTGACAACCTGGAGAGAAGTTCACCTTTG
        :::.:. ::.:::::.:  .:  :.:    :.:...: :::.:          :.:::
        ----TGCTCACTCTTCCCGT--ACCAGGC----GGCGGC-TGGGG-------CGCC----
             80        90            100              110

190       200       210       220       230       240
inputs  AAAAAAATTACCAGGGGGATGACGAATCAGTCAGATACAGACAATTTTCCTGACTCCAAG
                :::           :.:.:          :...: :.:: :.::::.:
        ----------CCA-------------CGGAC---------CTGTGTACCCGGCTCCTA-
                                                      120       130

250       260       270       280       290       300
inputs  GACTCACCAGGGGACGTCCAGAGAAGTAAACTCTCTCCTGTCTTGGACGGGGTCTCTGAG
         ::     :::.::             : ::  ::   ::   ::::   :::  ..:
        -AC-------GGGGCG--------------CGCTACCC---CT---ACGG---CTCCATG
                140                             150             160

310       320       330       340       350       360
inputs  CTTCGTCACAGTTTCGATGGCTCTGCTGCAGATCGCTACCTCCTCTCTCAGTCCAGCCAG
        ::  :   :  :.:    ::.   :  :: ::..:.   ::   ::..:       :..   .:
        CTGCCCCCCGG---CGGCTTCCCCGCGGCTGTGTGC--CCACC---------CGGGAGG
           170       180       190       200                   210

370       380       390       400       410       420
inputs  CCACAGTCTGCGGCCACTGCTCCCAGTGCCATGTTCCCGTACCCCGGCCAGCACGGACCG
        :..:::   :::::     :  .:.:::.    ::.:   ::    .:.:.   :
        GCGCAGT--TCGGCC-------CAGGAGCCG-------GTGC---GG-----GCAGT--G
           220              230               240
```

Fig. 7-1

```
              430       440       450       460       470       480
inputs GCGCACCCCGCCTTCTCCATCGGCAGCCCTAGCCGCTACATGGCCCACCACCCGGTCATC
       :::::.            :::.:  ::::  ::  ...  ::  :  .:  .:::::  ::  :
       GCGCG---------------GGCGG---TAGCAGCGGCGGGGGCGGCGGCCCGGGCACC
       250                         260         270       280

490       500       510       520       530       540
inputs ACCAACGGAGCCTACAACAGCCTCCTGTCCAACTCCTCGCCGCAGGGATACCCCACGGCC
       .  :::.:.         ::::::.    :    ..::::  :    :   .:.::            ::
       T--ATCAGT-------ACAGCCA--GGG--GGCTCCGCTCTACGGG------------CC
       290             300        310                           320

550       560       570       580       590
inputs GGCTACCCCTAC-CCACAGCAGTACGGCCACTCCTACCAAGGAGCTCCGTTCTACCAGTT
       :  :::::   .   ::.::::.:   :::   .  ::  :.:   ::::  .:  :        .:::
       G--TACCCTGGAGCCGCAGCGG--CGG--GATCTTGC---GGAGGACTGGGGGGCCTGGG
          330       340           350         360         370

600       610       620       630       640       650
inputs CTCCTCCACCCAGCCGGGGCTGGTGCCCGGCAAAGCACAGGTGTACCTGTGCAACAGGCC
       ::::       ::   ::::     :::          .::  ::  ::  :::::::::::::  ::::
       -GGTTCCA-------GGTTCTGGCTTCCG----TGCCCACGTCTACCTGTGCAACCGGCC
        380            390                400        410       420

660       670       680       690       700       710
inputs CCTTTGGCTGAAATTTCACCGGCACCAAACGGAGATGATCATCACCAAACAGGGAAGGCG
       ::  :::::  :::::  :::::  ::::::::  :::::::::::  ::  :::::::::  :::::
       TCTGTGGCTCAAATTCCACCGCCACCAAACTGAGATGATCATTACGAAACAGGGCAGGCG
          430       440       450       460       470       480

720       730       740       750       760       770
inputs CATGTTTCCTTTTTTAAGTTTTAACATTTCTGGTCTCGATCCCACGGCTCATTACAATAT
       :::::::::::  ::..::  ::  ::::::..   ::.:::.:::::::  ::  ::  :::::::.:
       CATGTTTCCTTTCTTGAGCTTCAACATAAACGGACTCAATCCCACTGCCCACTACAATGT
          490       500       510       520       530       540

780       790       800       810       820       830
inputs TTTTGTGGATGTGATTTTGGCGGATCCCAATCACTGGAGGTTTCAAGGAGGCAAATGGGT
       ::  ::..::  :::.:   :::::::  :::::   :::::  :  ::   ::..::.::::::::::
       GTTCGTAGAGGTGGTGCTGGCGGACCCCAACCACTGGCGCTTCCAGGGGGGCAAATGGGT
          550       560       570       580       590       600

840       850       860       870       880       890
inputs TCCTTGCGGCAAAGCGGACACCAATGTGCAAGGAAATCGGGTCTATATGCATCCGGATTC
       :  ::  :::::::::  ::::     ::  .:::::..::  :    ...:  ::::.:  ::  ::..::  ::
       GACCTGTGGCAAAGCCGACAATAACATGCAGGGCAACAAAATGTATGTTCACCCAGAGTC
          610       620       630       640       650       660

900       910       920       930       940       950
inputs CCCCAACACTGGGGCTCACTGGATGCGCCAAGAAATCTCTTTTGGAAAATTAAAACTTAC
       ::  ::  :::::            :  :::::::::::  ::.::..::  :::..:  .::.:::::::  ::
       TCCTAATACTGGTTCCCACTGGATGAGACAGGAGATTTCATTCGGGAAATTAAAACTCAC
          670       680       690       700       710       720
```

Fig. 7-2

```
              960        970       980        990       1000      1010
inputs  GAACAACAAAGGAGCTTCAAATAACAATGGGCAGATGGTGGTTTTACAGTCCTTGCACAA
        ::  ::::::::: ::.. .::  :::::  .   :::::: .:.:: :::::.:::::.:::::
        CAATAACAAAGGCGCAAATAACAACAACACCCAGATGATAGTCTTACAATCCTTACACAA
              730        740       750        760       770        780

1020       1030      1040       1050      1060      1070
inputs  GTACCAGCCCCGCCTGCATGTGGTGGAAGTGAACGAGGACGGCACGGAGGACACTAGCCA
         .:::::.::::: ::::::::.: :: :::::: :  :::::  :::. ::::::::. :. :
        ATACCAACCCCGACTGCATATTGTTGAAGTTACAGAGGATGGCGTGGAGGACTTGAATGA
              790       800        810       820        830        840

1080       1090      1100       1110      1120       1130
inputs  GCCCGGCCGCGTGC-AGACGTTCACTTTCCCTGAGACTCAGTTCATCGCCGTCACCGCCT
        ::::  : . ::. : :::: :: ::  ::: :.::.::  ::.:::::  ::  ::  ::::
        GCCCT-CAAAGACCCAGACTTTTACCTTCTCAGAAACGCAATTCATTGCAGTGACTGCCT
              850       860        870       880        890

1140       1150      1160       1170      1180       1190
inputs  ACCAGAACACGGATATTACACAACTGAAAATAGATCACAACCCTTTTGCAAAAGGATTTC
        ::::.::::: :::::::::..:::::.::.::.:::::  :::::  :::::::::::  ::
        ACCAAAACACCGATATTACTCAACTAAAGATTGATCATAACCCCTTTGCAAAAGGCTTCA
         900        910       920        930      940        950

1200       1210      1220       1230      1240      1250
inputs  GGGATAATTATGACACGATCTACACCGGCTGTGACATGGACCGCCTGACCCCCTCGCCCA
        :..::  ::  :::::  .:  ::  ::::::::   :  .::  .  :::  :  ::.::  ::  ::  ::::
        GAGACAACTATGATTCCATGTACACCGCTTCAGAAAATGACAGGTTAACTCCATCTCCCA
             960        970       980        990       1000      1010

1260       1270      1280       1290      1300       1310
inputs  ACGACTCGCCGCGCTC---GCAGATCGTGCCCGGGGCCCGCTACGCCATGGCCGGCTCTT
        ::  ::  ::  :  :::  :::::  ::  ::  ::..  ::  ::::  :.:            ::..
        CGGATTCTCCTAGATCCCATCAGATTGTCCCTGGAGGTCGGTACGGCGT-------TCAA
             1020       1030      1040       1050      1060       1070

1320       1330      1340       1350      1360      1370
inputs  TCCTGCAGGACCAGTTCGTGAGCAACTACGCCAAGGCCCGCTTCCACCCGGGCGCGGGCG
        ::::  :.   .::    ::  ::::   ::. : :::  :  :   :.::..:    ..::  :     ::
        TCCTTCT--TCC----CG-GAGCC-CTTTGTCAA--CACTTTACCTC--AAGC-C---CG
                   1080       1090      1100       1110

1380       1390      1400       1410      1420      1430
inputs  CGGGCCCCGGGCCGGGTACGGACCGCAGCGTGCCGCACACCAACGGGCTGCTGTCGCCGC
        :  .    . : ::..   .:::::    :::::.:: ::::::::  ::   ::  ::.:: :
        CTATTATAATGGCGAGA--GAACCG-----TGCCACAGACCAACGGCCTCCTTTCACCCC
             1120       1130            1140       1150       1160

1440       1450      1460       1470      1480       1490
inputs  AGCAGGCCGAGGACCCGGGCGCGCCCTCGCCGCAACGCTGGTTTGTGACGCCGG-CCAAC
        :..:::.  :::.::   ::  :.  .:::::  ::  ::.. ::  ::::  :::::  :   :::..:
        AACAGAGCGAAGAGGTGGCCA-ACCCTC-CC-CAGCGGTGGCTTGTCACGCCTGTCCAGC
             1170       1180       1190       1200       1210       1220
```

Fig. 7-3

```
        1500      1510      1520      1530      1540      1550
inputs AACCGGCTGGACTTCGCGGCCTCGGCCTATGACACGGCCACGGACTTCGCGGGCAACG-C
       :::: :   :::: . .:.. :: :.:     ..:: ::. ::  .:: ..  .:: :
       AACCTG--GGACCA-ACAAACTAGAC----ATCAGTTCCTATGA-ATCTGAATATACTTC
        1230      1240          1250      1260      1270

1560      1570      1580      1590      1600      1610
inputs GGCCACGCTGCTCTCTTACGCGGCGGCGGGCGTGAAGGCGCTGCCGCTGCAGGCTGCAGG
       . :::. ::::: :.::                :::.: ::. :  ::::   :  :: :::.
       TAGCACATTGCTCCCATA---------TGGCATTAAATCCTTGCC----C---CTTCAGA
         1280      1290              1300      1310              1320

1620      1630      1640      1650      1660      1670
inputs CTGCACTGGCCGCCCGCTCGGCTACTACGCCGACCCGTCGGGCTGGGGCGCCCGCAGTCC
       :. : :. :::     :: :: :: ::: : :::::...:  ::      :: :::.:
       CATCCCATGCC-----CTGGGGTATTACCCAGACCCAAC---CTTT----CCTGCAATG-
          1330         1340      1350      1360

1680      1690      1700      1710      1720      1730
inputs CCCGCAGTACTGCGGCACCAAGTCGGGCTCGGTGCTGCCCTGCTGGCCCAACAGCGCCGC
       :::: . :: ::    :.:::::.:      :: ::  ::.: :.         ::    .
       ---GCAGGG-TGGGG----AGGTCGAG----GTTCTTACCAGAGGA------AG----AT
          1370      1380              1390      1400

1740      1750      1760      1770      1780      1790
inputs GGCCGCCGCGCGCATGGCCGGCGCCAATCCCTACCTGGGCGAGGAGGCCGAGGGCCTGGC
       ::: ::        ::: : .: : ..  ::: ::.:...:    :.:::         :
       GGCAGC--------TGGACTAC-CATGGACCT-CCAGAAC----AAGCC----------C
         1410              1420       1430      1440

1800      1810      1820      1830      1840      1850
inputs CGCCGAGCGCTCGCCGCTGCCGCCCGGCGCCGCCGAGGACGCCAAGCCCAAGGACCTGTC
       :.: :.: :::     :: : :.::: ::.::.::: . ...:    .:::: :
       CACTGTGTTCTC-----TGAAGATCAGCTC-TCCAAGGAGAAAGTGAAAGAGGAAATTGG
          1450         1460      1470      1480      1490

1860      1870      1880      1890      1900      1910
inputs CGATTCCAGCTGGATCGAGACGCCCTCCTCGATCAAGTCCATCGACTCCAGCGACTCGGG
       :  :::   :::::: :::::.::: : :: :::::.:: : :: ::::. :: ::.::
       CTCTTC---TTGGATAGAGACACCCCCTTCCATCAAATCTCTAGATTCCAATGATTCAGG
         1500      1510      1520      1530      1540      1550

1920      1930      1940      1950      1960
inputs GATTTAC----GAGCAGGCCAAGCGGAGGCGGATCTCGCCGGCCGACACGCCCGTGTCCG
       ..:.:::     :.::. : ::::::.:::::: : :: ::  .:..:.: : ::.. :
       AGTATACACCAGTGCTTGT-AAGCGAAGGCGGCTGTCTCCTAGCAACTC--CAGTAAT-G
         1560      1570      1580      1590      1600      1610

1970      1980      1990      2000      2010      2020
inputs AGAGTTCGTCCCCGCTCAAGAGCGAGGT-GCTGGCCCAGCGGGACTGCGAGAAGAACTGC
       :.:.:::. :: : : :::.: ::::. . ... :.: .:... . :...::::: :. :
       AAAATTCACCCTCCATAAAGTGTGAGGACATTAATGCTGAAGAGTATAGTAAAGA-CACC
         1620      1630      1640      1650      1660
```

Fig. 7-4

```
          2030      2040      2050      2060      2070      2080
inputs GCCAAGGACATTAGCGGCTACTATGGCTTCTACTCGCACAGCTAGGCCGCCCCTACCCGC
       : ::.:.::: .: :: ::  ::::     ::. :  .:::::.::      :::::  .
       TCAAAAGGCATGGGAGGGTATTATG----CTTTTTACACAACT-------CCCTAAAGAG
      1670      1680      1690      1700             1710

2090      2100      2110      2120      2130      2140
inputs CCGGCCCCGCCGCGGCCCGGACCCCCAGCCAGCCCCTCACAGCTCTTCCCCAGCTCCGCC
          .        .:: :..      ..:    :::: :.:    :  .:::  :  .:     .:  :
       TTATTTTAACCTCAA---AAA---TTAGCTAACTTTTTGCAGATGGAC--TTGGTGGTGT
      1720      1730         1740      1750      1760      1770

2150      2160      2170      2180      2190      2200
inputs TCCCCACACTCCTCCTTGCGCACCCACTCATTTTAT--TTGACCCTCGATGGCCGT-CTG
       :     . .  ::  ::  ::::   :          ::......  ::  .::  ::  :     ::  :    ::
       TTTTTGTTGTCTTCTTTGCCTAGGTKGCCAAAAAGAWGTTKGCCTTCCA---CCTTGATG
         1780      1790      1800      1810      1820

2210      2220      2230      2240      2250      2260
inputs C-AGCGAATAAGTGCAGGTCTCCGAGCGTGATTTTAACCTTTTTTGCACAGCAGTCTCTG
       : . : . :. :::::.  :::: .:. :... :    .::..     .::.  . ..: :::
       CWTCCTGKTTKGTGCAATTCTCTAAAAGAAGGT---GCCAA---AGCTTTTTGATTGCTG
      1830      1840      1850      1860             1870      1880

2270      2280      2290      2300      2310      2320
inputs CAATTAGCT--CACCGACCTTCAACTTTGCTGTAAACCTTTTGGTTTTGCTACTTACTCT
       ::. ::.::   ::  .::::    :.:.::   :  .:::   .::.  :.::..  :. ...:
       CAGGTAACTGAAACAAACCT--AGCATTTTTWAAAA--ATTARGATTAA-TGGAAGC---
         1890      1900      1910      1920      1930

2330      2340      2350      2360      2370      2380
inputs TCTTCTGTGGAGTTATCCTCCTACATTCCCCTCCCCCTCGTCTTCTCTTACCTCCTACTT
       :::   ..  :...  :::.    ::  .: .: ..  ::     ::   . ::  ::::  :  .  .
       -CTTTAAGGATTTTAAAATTCGAAGGGATCCAAGGTTCTGTATTTATCTTAT-TGGGGAGA
       1940      1950      1960      1970      1980      1990

2390      2400      2410      2420      2430
inputs CTCTTTCTTGT-AATGAAACT--CT-TCACCTTTAGGAGACCTGGGCAGTCTGTCAGGCA
       :.::..:     :  ::..:::.:.      ::  :  :  :.::.::..:  ::..:  ::...:.:.  ...:  .
       CACTAACMMTTCAAAGAAGCAGGCTGTGAACATTGGGTGCCCAGTGCTATCAGATGAGTT
         2000      2010      2020      2030      2040      2050

2440          2450      2460      2470      2480
inputs GCAGC----GATTC-CTCCGCCAAGTCTCGGCCCTC---CACATTAA--CCATAGGATGT
        . ..:     :::::: :.   : :. : :..   ::    :: :::...:  ::.... :.:..
       AAAACCTTTGATTCTCATTTCTATTTGTAAATTCTTAAGCAAATAGAAGCCGAGTGTTAA
         2060      2070      2080      2090      2100      2110

2490      2500      2510      2520      2530      2540
inputs TGACTCTAGAACCTGGACCCACCCAGCGCGTCCTTTCTTATCCCCGAGTGGATGGATGGA
       :.. : :..:  .:::..:         .::    ::::  :  :..:      ...:.. .   .::  .
       GGTGTTTTGCTTCTGAAAGAG---GGCTGTGCCTTCCGTTTCAGAAGGAGACATTTTGCT
         2120      2130         2140      2150      2160
```

Fig. 7-5

```
        2550      2560      2570      2580      2590      2600
inputs TGGATGGATGGATGGATGTTAATAATTTAGTGGACAAGCCTGTGAAATGATTGTACATA-
        : . .  :  .:. :  .::..::  : :.:.:    ::..:  ...  ..........:.:.
       GTTACATTCTGCCAGGGGCAAAAGAT--ACTAGGC---CCAGGAGTCAAGAAAAGCTTTT
        2170      2180      2190      2200      2210      2220

2610      2620      2630      2640      2650      2660
inputs GTGTAATTAT--GTAACGAATGGCAT-GTTTTATTCTCGTCAAGGCACAAAACCAGTTCA
       :::.::  :..   ::..:.   ::.:.:  :.::  ::  .:   :  .:   . ...:  ::.   ::
       GTGAAAGTGATAGTTTCACCTGACTTTGATTCCTTAACCCCCGGCTTTTGGAACAAGCCA
        2230      2240      2250      2260      2270      2280

2670      2680      2690      2700      2710      2720
inputs TGCTTAACCTTTTTCCTTTCCTTTCTTTGCTTTT--CTTTCTCTCCTCTCATACTTTCT-
       ::  ::..::  :.  ::: .    ::  :  :  .:::  .   :::  ::     :  :::  :.::  :  :
       TG-TTTGCCCTAGTCCAGGA-TTGCCTCACTTGAGACTTGCTAGGC-CTC-TGCTGTGTG
         2290      2300      2310      2320      2330

2730      2740      2750      2760      2770      2780
inputs CTTCTCTCTCTTTTAATTTTCTTGTGAGATAATATTCTAAGAGGCTCTAGAAACATGAAA
       ::     :   :  .  :...  .  ::.  :..::::   :..  :  ..:..:::  :.:   :.::  :...:::
       CTGGGGTGGCCAGTGGGACTCAGGAGAGAGCAAGCT-AAGGAGTCACCAAAAAAAAAAAA
        2340      2350      2360      2370      2380      2390

2790      2800      2810      2820      2830      2840
inputs TACTCAGTAGTGATGGGTTTCCCACTTCTCCTCAATCCGTTGCATGAAATAATTACTATG
        .:    :...:...:.  .:...::    :   :        ...: ::::  .::..  ::...:::.
       AA---AAAAAAGGGAGAATTTAAAAGT------GTACAGTTGTGTGTT-TAGATACA---
        2400      2410      2420             2430      2440

2850      2860      2870      2880      2890
inputs TGCCCTAATGCACACAAATAGCTAAGGAGAATCCACCCAAACACCTTTAAAGG
        :::..:  : :  :...:.:  ::..  :  ..: ::    :....  :.    ...:
       ----CTATAGAATA-ATGTGG-TATATATTGTACAAATAGTCTACAG-GGTGT
           2450      2460      2470      2480      2490
```

Fig. 7-6

ALIGN calculates a global alignment of two sequences
 version 2.0uPlease cite: Myers and Miller, CABIOS (1989)
> Genbank U49251 - Mus musculus putative cerebral   3814 aa vs.
> M154                                              2491 aa
scoring matrix: pam120.mat, gap penalties: -12/-4
42.6% identity;        Global alignment score: 1634

```
                10        20        30        40        50        60
inputs  TTTCTGTCTAGTGGAGGGGTCTGTGGATTCCTAGTGTATGATAAACAGGACTTTAAAACC
         :..:      :.:.:       :::                       :...::    ::
        ------CATG-------GACAG------CCT---------------GAGCT------CC
                                    10

70        80        90       100       110       120
inputs  CAGGGACGGGAGGGCAGTGTTCAGGTTCTAGAGCTATGCAGCTGGAGCATTGCCTCTCTC
                :..::         :::.:::                           ::::
        ----------GAGC--------GGTACTA---------------------CCTC----
                  20                30

130       140       150       160       170       180
inputs  CTTCTATCATGCTCTCCAAGAAATTTCTCAATGTGAGCAGCAGCTACCCACATTCGGGCG
            :..::    : ::..    : :::: : :.  :.: ::::           :::
        ---CAGTC-----CCCCGG-----TCCTCA--GGGGTCGG-AGCT-----------GGC-
                40          50            60

190       200       210       220       230       240
inputs  GATCTGAGCTTGTCTTGCATGATCATCCCATTATCTCGACCACTGACAACCTGGAGAGAA
         :: ::     : :::.   ::.:::::.:.   :  :.: .: :     :::::.:
        ----TGCGC----CCTGCTCACTCTTCCCGTA--CCAGGCGGCGG-----CTGGGG----
            70         80        90           100

250       260       270       280       290       300
inputs  GTTCACCTTTGGAAAAAATTACCAGGGGGATGACGAATCAGTCAGATACAGACAATTTTC
         :..::              :::            :.:.:           :...: :.:
        ---CGCC-------------CCA------------CGGAC---------CTGTGTAC
           110                                          120

310       320       330       340       350       360
inputs  CTGACTCCAAGGACTCACCAGGGGACGTCCAGAGAAGTAAACTCTCTCCTGTCTTGGACG
        : :..:::.:  ::     :::.::               : :: ::   ::   :::
        CCGGCTCCTA--AC-------GGGGCG--------------CGCTACCC---CT---ACG
        130                140                             150

370       380       390       400       410       420
inputs  GGGTCTCTGACCTTCGTCACAGTTTCGATGGCTCTGCTGCAGATCGTTACCTACTCTCTC
        :   :::  ..:::  :   : :.:   ::.    :  : :: ::.:.   :..::  :.:
        G---CTCCATGCTGCCCCCCGG---CGGCTTCCCCGCGGCTGTG---TGCC--CAC----
            160       170       180       190        200
```

Fig. 8-1

```
               430       440       450       460       470       480
inputs AGTCCAGCCAGCCACAGTCTGCGGCCACCGCTCCCAGTGCCATGTTCCCGTACCCCAGCC
       ::.:   .: :.:::: :  :::::       :  .:.:::. ::    ::  .:     ::
       ---CCGGGAGGGCGCAGT--TCGGCC-------CAGGAGCCG-GTG--CGGGC---AGT-
             210       220              230         240

490       500       510       520       530       540
inputs AGCACGGACCGGCGCATCCCGCCTTCTCCATCGGCAGCCCCAGTCGCTACATGGCCCACC
       .::.:::.:  :  :::  :      :  .:::::.:::::          :::   :::
       GGCGCGGGCGGTAGCAGC-----GGCGGGGGCGGCGGCCC-----------GGGC--ACC
          250       260            270                  280

550       560       570       580       590       600
inputs ACCCGGTCATTACCAACGGAGCTTACAACAGCCTGCTGTCCAACTCTTCGCCGCAGGGCT
       .  :.::  :  ..:::.  ::.:::   :  .:.   ::.:  : ::.   :::  .::.::
       TATCAGT-ACAGCCAG-GGGGCT--CCGCT--CTACGGGCCG----TAC-CCT-GGAGC-
           290       300         310       320              330

610       620       630       640       650       660
inputs ACCCCACGGCCGGCTACCCCTACCCACAGCAGTACGGCCACTCCTACCAAGGAGCCCCTT
       :  :   .::::: :: :      : :.:   : ...:.:  .  :::::.           .::.:      :
       -CGCAGCGGCGGGAT---CTTGCGGAGGACTGGGGGGCCT---------GGGGG-----T
             340       350       360                  370

670       680       690       700       710       720
inputs TCTACCAGTTCTCCTCCACCCAGCCCGGGTTGGTGCCCGGCAAGGCGCAAGTATACCTGT
       ::     :    .:::::     :  .::   .:::::.           ::   :                :::::::
       TC--CAGGTTCTG-GCTTCCGTGCCCA---------CGTC------------TACCTGT
         380       390                  400                  410

730       740       750       760       770       780
inputs GCAACAGGCCACTTTGGCTGAAATTTCATCGGCATCAAACGGAGATGATCATCACTAAAC
       :::::  :::::.::  :::::   :::::   ::   ::   ::   :::::   :::::::::::::  ::    ::::
       GCAACCGGCCTCTGTGGCTCAAATTCCACCGCCACCAAACTGAGATGATCATTACGAAAC
          420       430       440       450       460       470

790       800       810       820       830       840
inputs AGGGAAGGCGCATGTTTCCCTTTTTGAGTTTTAACATTTCTGGTCTCGATCCCACCGCTC
       ::::  :::::::::::::   ::  :::::  ::  :::::::..   ::.:::.:::::::::  ::  :
       AGGGCAGGCGCATGTTTCCTTTCTTGAGCTTCAACATAAACGGACTCAATCCCACTGCCC
          480       490       500       510       520       530

850       860       870       880       890       900
inputs ATTACAATATTTTTGTGGATGTGATTTTGGCGGATCCCAATCACTGGAGGTTTCAAGGAG
       :  ::::::.:  ::   :::.::    :::.:         :::::::   :::::  :  ::     ::.::.::.:
       ACTACAATGTGTTCGTAGAGGTGGTGCTGGCGGACCCCAACCACTGGCGCTTCCAGGGGG
           540       550       560       570       580       590
```

Fig. 8-2

```
             910       920       930       940       950       960
inputs GCAAATGGGTTCCTTGTGGCAAAGCGGACACCAATGTGCAAGGAAACCGGGTCTATATGC
       ::::::::::  :  :::::::::::: ::::  :: .:::: .:: :::  ...: :::.: :
       GCAAATGGGTGACCTGTGGCAAAGCCGACAATAACATGCAGGGCAACAAAATGTATGTTC
             600       610       620       630       640       650

970       980       990      1000      1010      1020
inputs ATCCGGATTCCCCCAACACTGGGGCTCACTGGATGCGGCAAGAAATCTCTTTTGGAAAAT
       : ::.:: :: :: :: :::::  :  :::::::::: :..::.::.::  ::.::  ::.::::
       ACCCAGAGTCTCCTAATACTGGTTCCCACTGGATGAGACAGGAGATTTCATTCGGGAAAT
             660       670       680       690       700       710

1030      1040      1050      1060      1070      1080
inputs TAAAACTTACCAACAACAAGGGAGCATCAAACAACAATGGGCAGATGGTGGTTTTACAGT
       :::::::  :::::  ::::::.::  :::.   .:::::::::  .   :::::::.:.:::   ::::::.:
       TAAAACTCACCAATAACAAAGGCGCAAATAACAACAACACCCAGATGATAGTCTTACAAT
             720       730       740       750       760       770

1090      1100      1110      1120      1130      1140
inputs CCCTGCACAAGTACCAGCCCCGTCTGCACGTGGTGGAAGTGAATGAGGATGGCACAGAGG
       ::  :..::::::..:::::.::::::.:  ::  ::::: :  .::::::::::. .::::
       CCTTACACAAATACCAACCCCGACTGCATATTGTTGAAGTTACAGAGGATGGCGTGGAGG
             780       790       800       810       820       830

1150      1160      1170      1180      1190
inputs ACACCAGCCAGCCAGGCCGAGTCC-AGACGTTCACTTTTCCGGAGACTCAGTTCATCGCT
       ::.  :.  ::::  : .::.:: ::::  ::  ::  ::  :.::.:: ::.  ::::::  ::..
       ACTTGAATGAGCCCT-CAAAGACCCAGACTTTTACCTTCTCAGAAACGCAATTCATTGCA
             840       850       860       870       880

1200      1210      1220      1230      1240      1250
inputs GTCACCGCCTACCAGAACACGGATATTACACAACTAAAAATAGATCATAACCCCTTTGCA
       ::  ::  :::::::::.:::::  :::::::::.:::::::::..:.::::::::::::::::::
       GTGACTGCCTACCAAAACACCGATATTACTCAACTAAAGATTGATCATAACCCCTTTGCA
        890       900       910       920       930       940

1260      1270      1280      1290      1300      1310
inputs AAAGGATTTCGAGATAACTATGACACGATCTACACGGGCTGC-GACATGGACCGCTTGAC
       :::::  ::  ::::  :::::::::  .: ::  :::::  :  ::  :  ::  :.  ::: : ::.::
       AAAGGCTTCAGAGACAACTATGATTCCATGTACACCG-CTTCAGAAAATGACAGGTTAAC
        950       960       970       980       990      1000

1320      1330      1340      1350      1360      1370
inputs CCCGTCGCCCAACGACTCTCCGCGCTC---GCAGATCGTGCCCGGCGCCCGCTACGCCAT
       ::.::  ::::   ::  :::::  : ::     :::::  ::   ::  ::  :  ::  ::::  :..:
       TCCATCTCCCACGGATTCTCCTAGATCCCATCAGATTGTCCCTGGAGGTCGGTACGGCGT
       1010      1020      1030      1040      1050      1060
```

Fig. 8-3

```
            1380      1390      1400      1410      1420      1430
inputs GGCCGGCTCTTTCCTGCAAGACCAGTTCGTGAGCAACTACGCCAAGGCCCGCTTCCACCC
            : :..: ::: :...  ::     :: : ::: ::.: :::   : :  :.::.:
       -------TCAATCCTTCTT--CC----CG-GAGCC-CTTTGTCAA--CACTTTACCTC--
               1070      1080         1090         1100

1440      1450      1460      1470      1480      1490
inputs GGGCGCCGGCGCGGGTCCCGGGCCGGGCACGGACCGCAGCGTGCCGCACACCAACGGGCT
        . :::  :::  ::.. :   . ::.:   :.::::    ::::::.:: :::::::: ::
       --AAGCC--CGCTATTATAATGGCGAGA--GAACCG-----TGCCACAGACCAACGGCCT
           1110      1120      1130         1140      1150

1500      1510      1520      1530      1540      1550
inputs GCTGTCCCCGCAGCAGGCCGAGGACCCGGGCGCGCCGTCGCCGCAGCGCTGGTTCGTCAC
        :: :: ::  ::.:::. :::.:: :: :. .::  : :: ::::: ::: : :::::
       CCTTTCACCCCAACAGAGCGAAGAGGTGGCCA-ACC--CTCCCCAGCGGTGGCTTGTCAC
         1160     1170      1180      1190       1200      1210

1560      1570      1580      1590      1600      1610
inputs GCCGG-CCAACAACCGGCTGGACTTCGCGGCCTCGGCCTACGACACGGCCACGGA-CTTC
       ::: : :::.:::::  :  ::::  . .:... ::  .:  :..:.. .:    : ::.: ::
       GCCTGTCCAGCAACCTG--GGACCA-ACAAACT-AGACATCAGTTC--CTATGAATCTGA
         1220     1230       1240       1250        1260

1620      1630      1640      1650      1660      1670
inputs GCCGGCAACGCGGCCACGCTGCTGTCGTATGCGGCCGCGGGCGTGAAGGCGCTGCCCTTG
        .  .:..:   :   :::.  ::::   :.:::            :::.: ::.  : :::::
       ATATACTTCTAG--CACATTGCTCCCATAT---------GGCATTAAATCCTTGCCC---
       1270     1280      1290                1300      1310

1680      1690      1700      1710      1720      1730
inputs CAGGCCGCGGGCTGCACGGGCCGCCCGCTCGGCTACTACGCCGACCCTTCGGGCTGGGGC
         :  :.:.:.  :  :. :::        :: :: :: :::  : :::::..:   ::     :
       ----CTTCAGACATCCCATGCC-----CTGGGGTATTACCCAGACCCAAC---CTT--TC
           1320      1330           1340      1350          1360

1740      1750      1760      1770      1780      1790
inputs GCGCGCAGCCCCCCGCAGTACTGCGGCGCCAAGTCGGGCTCCGTGCTCCCCTGCTGGCCC
       ::.. .:    ::::  . :: ::    :.:.:::.:    :: ::   ::.:  :.
       CTGCAATG------GCAGGG-TGGGG----AGGTCGAG----GTTCTTACCAGAGGAA--
                       1370      1380           1390      1400

1800      1810      1820      1830      1840      1850
inputs AACAGCGCCGCGGCCGCCGCGCGCATGGCCGGCGCCAACCCCTATCTGGGCGAGGAGGCC
        .: .::..  :   :.: .::.  :  .: :   ::. : .:  :.::::  .:::         .:  :
       GATGGCAGCTGGACTACCATGGACCT--CCAGAACAAGCCCC--ACTG-------TGTTC
         1410      1420      1430         1440             1450

1860      1870      1880      1890      1900      1910
inputs GAGGGCCTGGCGGCCGAGCGCTCGCCGCTGGCGCCCGCCGCCGAGGACGCCAAGCCCAAG
        :::. :. :.  ::::  ::. ..:: :        .   :..:.: :        :.:
       T-----CTGAAGATCA---GCTCTCCA-AGGAG------AAAGTGAAAG--------AGG
              1460          1470           1480            1490
```

Fig. 8-4

```
        1920      1930      1940      1950      1960      1970
inputs GACCTGTCCGACTCCAGCTGGATCGAGACGCCCTCCTCCATCAAATCCATCGACTCCAGC
       .:   ::  :   .::  :.   :::::  :::::.:::  :  ::::::::::  :  ::  ::::.
       AAATTGGC--TCTTCT--TGGATAGAGACACCCCCTTCCATCAAATCTCTAGATTCCAAT
                1500      1510      1520      1530      1540

1980      1990      2000      2010      2020      2030
inputs GACTCGGGGATTTACGAGCAGGCCAAGCGGAGGCGGATCTCGCCGGCTGACACGCCGGTG
       ::  ::..::...:.:::.   :::   :...   :  :.:::.:     :  :::::::.:.:
       GATTCAGGAGTATACAC-CAGTGCTT--GTAAGCGAA----GGCGGCTGTCTC-------
       1550      1560      1570      1580      1590

2040      2050      2060      2070      2080      2090
inputs TCTGAGAGCTCGTCCCCGCTCAAGAGCGAGGTGCTGGCCCAGCGGGACTGCGAGAAGAAC
       ::..      :..:  ::.  :  :.::     :...  :.    :::         .:   :...:::
       -CTAG-----CAACTCCAGTAATGA---AAATTCA--CCC------TC--CATAAAG---
                1600      1610      1620      1630

2100      2110      2120      2130      2140      2150
inputs TGCGCCAAGGACATAGGCGGCTACTATGGCTTCTACTCGCACAGCTAGGCCGCCAGCCCG
       ::.    :::::::...    :.::...:  :  ::        :  .:.:  :..::.   :.
       TGTG---AGGACATTAA----TGCTGAAGAGTATA--------GTAAAGACACCT---CA
                1640      1650              1660      1670

2160      2170      2180      2190      2200      2210
inputs CTCGCCCGCCCGCCCGTGCCCCCGGCCCCCCAGCTCGGCCCCACGTCCTCCTTCCCAGGC
       . :                                  ::. ::       :            :::
       AAAG-------------------------------GCATGG------G----------AGG-
                                            1680

2220      2230      2240      2250      2260      2270
inputs CCGTTCTAGCGCACTCGCTCTTTCACTTGACCCTCGATGACCGTCTGCGGGGATAAGTGC
       ::.  :...  ::.  :       ::.:.:::..  .::::                 .:...:::
       --GTA-TTATGCTTT-----TTACACAACTCCCT----------------AAAGAGT--
         1690      1700      1710

2280      2290      2300      2310      2320      2330
inputs AGGTCTCTCACTATGATTTTAAAACTCTTCTTTTTTCTTTCTTTCTCTCTACACAG
                      ..::..:..:  ::::...  ::::   ::..::::  :
       ---------------TATTTTAACCTCAAAAATTAGCTAACTTTTT--------------
                      1720      1730      1740      1750

2340      2350      2360      2370      2380      2390
inputs CCTTCTCTGCAGTTAGCGCACCGACCTTGAACCTGGCTGTAAACCTTGTGGTTTTCCAAC
              ::::.:.:       ::::.    :::  :::...   ::::  ::      :...:
       --------GCAGATGGA---------CTTGG---TGG-TGTTTT--TTGTTGT----CTTC
                               1760      1770      1780

2400      2410      2420      2430      2440      2450
inputs TTTTCGTCTGTGAGGTTATGATCCTCCCTGTCTTTTTTCCACCCCCTTCTCCTTGCCCCA
       :::  :   ::    ::::  .        ::.      .:.      ::    ::.  ::       .:::::       :
       TTTGC--CT---AGGTKG----CCAAAAAGA-WGTTKGCCTTCC-----ACCTTG----A
         1790      1800      1810      1820
```

Fig. 8-5

```
              2460       2470       2480       2490       2500       2510
inputs CTCATCCTCTCCTTTCTCTTGGAATGAAACTCTTCAACTTTAGGAGACCTGGGCAATCCT
       : ::::           : ..: ....:. :::. ::..:..::      .::         :
       TGCWTCCT------------GKTTKGTGCAATTCT-CTAAAAGA----AGG-------T
         1830                     1840      1850             1860

2520       2530       2540       2550       2560       2570
inputs GCCAGGCAGCAGCGATTCCGACCCGCCTTGTCTTGGCCTCCCTATTTAACCATAGGATGT
       ::::.  :::                                     :.:::       :..::
       GCCAA--AGC-------------------------------------TTTTT-------GATTGC
                                                       1870

2580       2590       2600       2610       2620       2630
inputs TGACTCTAGAACCTGCACCCACCCAGCGCGTCCTTTCTTATACCCGAGTGGATGGATGGA
       ::     :...:.: ::: : : :              .:::. :..:.:.
       TG---CAGGTAACTGAAACAA---------ACCTAGCATTTT----------------
    1880           1890          1900

2640       2650       2660       2670       2680       2690
inputs TGGATGGATGGATGGTAGGGATGTTAATACTTTTAGTGGAACAAAGCCTGTGAAATGATT
              : .:....:.. :::             ::.::::    :::::  :.:.   ::::
       --------TWAAAAATTARGAT----------TAATGGA----AGCCTTTAAG--GATT
            1910      1920                1930              1940

2700       2710       2720       2730       2740       2750
inputs GTATATAGTGTTAATTTATTGTAACGAATGGCTAGTTTTTATTCTCATTGTCAAGGCACA
                :::::.::     ::::: ::          .::         :::::
       ----------TTAAATT-------CGAAGGG----------ATC-------CAAGG----
                 1950              1960

2760       2770       2780       2790       2800       2810
inputs AAACCAGTTCACGCTTAACTTTTTATTCCTTTCCTTTCTTCTCCTTTTCTTTTTCTCCTC
                                                        ::::  :.:
       ------------------------------------------------TTCTGTAT------
                                                         1970

2820       2830       2840       2850       2860       2870
inputs TCATTCTTTCTCTTCTCCCACACCCTTTGTTTTCTTGTGAGTTATTAAAGATATTCTAAG
                                       ::.::::..: .:
       ----------------------------TTATCTTATTGG------------------
                                          1980

2880       2890       2900       2910       2920       2930
inputs AGGCTCTGGAAACACGAAGCACTTCATAGTGGTGGCTTTCTCACTTCTCAGTTCGTTGCA
       :::.:::: :: :  :::::.::..:                            :::      ::
       ------GGAGACACTAA-CMMTTCAAAGAAG----------------CAG------GC-
              1990       2000      2010

2940       2950       2960       2970       2980       2990
inputs TGATGTAACCACTGTGTGCCCTGGTGCACACAATGTAGCTAAGGAGAATCCACCTGAACA
       :::.: :: :: :::::::.: :::. .::..         :...: ..:..::.     ....
       ---TGTGAACATTGGGTGCCCAG-TGCTATCAGA-----TGAGTTAAAACCTTTGATTCT
          2020       2030       2040           2050       2060
```

Fig. 8-6

```
         3000      3010      3020      3030      3040      3050
inputs CCTGTAAAAGCTAGTTGTCTGTTCCTAGGCGAGTCGAGTAAGTGACACGATGCCTGCCAG
         : : :     ::: ::::  ..:::  ::.::.:.: ::.              :::..
       CATTT-----CTATTTGTAAATTCTTAAGCAAATAGAA----------------GCCGA
       2070      2080      2090                              2100

3060      3070      3080      3090      3100      3110
inputs GCGGACTTAACTGGAGTTCTATGTGTTTCTCCCTTCCTTCTAAATGGAATGGCCCCACAT
       : :    ::::  ::.:::                  ::  ::::::.::.:..   :::
       GTG---TTAA--GGTGTT---------------TTGCTTCTGAAAGAG--GGC-------
              2110                      2120          2130

3120      3130      3140      3150      3160      3170
inputs CAGCAATATTATTTTGCCTTATTTGTTTTTCCCCAAAGTGCCAAATCCATTACTGGTCTG
                   : :::::::                              ::.::.:.:.
       -----------TGTGCCTT----------------------------CCGTTTCAGA----
                  2140                                2150

3180      3190      3200      3210      3220      3230
inputs TGCAGGTGCCAAATATGCTGATAAACTGTTTCTGACTATCTTTTCAGACCCCACTCCACC
       :::.: ::.  :.:::::.::           :..:::       .::
       ---AGGAGACAT-TTTGCTGTTA------------CATTCT------GCC----------
          2160     2170                 2180

3240      3250      3260      3270      3280      3290
inputs TTTATATGCTGTAAATCTTTGTAATGAGTAATCTACTAATGATATAGATGACTGAATTGT
       : . ::...:.::                    ::::               :.:
       ---AGGGGCAAAAGAT------------------ACTA-----------GGC--------
             2190                                      2200

3300      3310      3320      3330      3340      3350
inputs TGGTAACTATAGTGTAGTCTAGTGAAGATGAATTGTGTGAGTTGTATATTTTACTGCATT
       : :       : :::::.::..::: :  .:::::..::: .:: .:: . ::: : :
       ------CCA----GGAGTCAAGAAAAGCT--TTTGTGAAAGTGATAGTTTCACCTG-ACT
              2210    2220          2230        2240

3360      3370      3380      3390      3400      3410
inputs TTAGTTTGAAAAACGATTCCCCCACCACTTAGAGACAGCTGAAATTTGACTTTCTTGGGA
       ::..::    :  ...::::                          ::.::::   :::.:
       TTGATTC-----CTTAACCCCC----------------------GGCTTT--TGGAA
       2250     2260                                2270

3420      3430      3440      3450      3460      3470
inputs AAACACTAGCATTATTGCAAGTAAGACTGATTCCCCCAAGTCTTGTTATATTTGATAAG
          :.:::      ::.::..:         :::.::::
       -----CAAGC-------CATGTTTG---------CCCTAGTC-----------------
            2280          2290

3480      3490      3500      3510      3520      3530
inputs GAGCATTAATCCCCCTGGAAATAGATTAGTAGGATTTCTAATGTTGTGTAGCAAACTTAT
       ::  :.: ::  :.                    ::       ::...:...:..
       ---CAGGATTGCCTCA-------------------CT-------TGAGACTTGCTAG-
          2300     2310                                2320
```

Fig. 8-7

```
            3540      3550      3560      3570      3580      3590
inputs ACTTTTTTTGTACTTTAAAATCAATGTGAAATATGCATCATACACAATATTCAATCTAGA
                                         :: ::.   .:..:.: :
       ---------------------------------GCCTCT---GCTGTGTGC--------
                                         2330       2340

3600      3610      3620      3630      3640      3650
inputs TTCCAGTCTATGGGGGGATTTGTCCTAATAGGAATTCAGGGTCTAAACGTGGGTATACTT
          :::::          :: ::..   .::.: :::::.         :.:.: :...::.
       ----------TGGGG-----TGGCCAG--TGGGACTCAGGA-------GAGAGCAAGCTA
                            2350       2360                2370

3660      3670      3680      3690      3700      3710
inputs TGGC-TCTCCTGTAAATCAAATGTTGTGATTTTTTATATTTGTTTTGTTTTGTCTGTGAA
       .::   ::..::...:::.  :::.......                            ::
       AGGAGTCACCAAAAAAAAAAAAAAAAAA-------------------------------AA
       2380       2390      2400

3720      3730      3740      3750      3760      3770
inputs TTGAATAATTTATACAAGTACACACTCCACTGAGAATCGTTTTGTTTTCTGCTCGTTTGT
       . .:  :::::::.:  ..:::::         . ::.:.  :::::.:.   .:.: .:.:.
       AGGGAGAATTTAAAAGTGTACA------GTTGTGT---GTTTAGAT----ACACTATAGA
        2410      2420            2430       2440          2450

3780      3790      3800      3810
inputs ATCGTCTGTGTATAACAAGTAAAATAAATCTGGTAAAATGCT
       ::  .:  :: :::::.  ..::: ::..:.:::.  :....:: :
       ATAATGTG-GTATATATTGTACAAATAGTCTA-CAGGGTG-T
        2460      2470      2480      2490
```

Fig. 8-8

MTBX PROTEIN AND NUCLEIC ACID MOLECULES AND USES THEREFOR

RELATED APPLICATIONS

This application is a continuation-in-part of U.S. patent application Ser. No. 09/163,116, filed Sep. 29, 1998, which claims priority to U.S. Provisional patent application Ser. No. 60/089,467, filed Jun. 16, 1998, and of U.S. patent application Ser. No. 09/188,811 (MNI-046CP), filed Nov. 9, 1998, the contents of which are incorporated herein by reference.

BACKGROUND OF THE INVENTION

The precise regulation of the events occurring during embryonic development as well as during tissue repair in adult organ systems is modulated in part by transcription factors.

Certain disease states, such as Dilated Cardiomyopathy (DCM), have been linked to inappropriate transcriptional regulation. DCM is a leading cause of cardiovascular morbidity and mortality and is characterized as a heterogeneous group of myocardial diseases characterized by cardiac dilation and impaired myocardial contractility (Richardson, P. et al (1996) Report of the 1995 World Health Organization/International Society and Federation of Cardiology Task Force on the Definition and Classification of Cardiomyopathies. *Circulation* 93:841–842). This syndrome consists of ventricular enlargement, abnormal systolic and diastolic left ventricular function, symptoms of congestive heart failure, and premature death due predominantly to heart failure and cardiac arrhythmias. Coronary artery disease, valvular heart disease, viral infection, toxins, autoimmunity, and primary genetic abnormalities can all cause dilated cardiomyopathy, but in many patients it is idiopathic (Leiden, J. M. (1997) *N Engl J Med* 337:1080–1081). Studies have indicated that a common set of molecular and cellular pathways accounts for the progression of this disease.

To date, two classes of genes have been implicated in DCM. The first class comprises genes that encode structural proteins like dystrophin (Muntoni, F. et al (1993) *N Engl. J Med* 329:921–925) and muscle LIM (Lin-11, Isl-1, and Mec-3) protein (Arber, S. et al (1997) *Cell* 88:393–403.; Arber, S. et al (1994) *Cell* 79:221–231). These proteins organize the contractile apparatus of cardiac myocytes and ensure their structural integrity. A related disease, Marfan's syndrome, also effects the cellular-extracellular relationship in the heart. Marfan's syndrome is an autosomal dominant disorder of connective tissue that is characterized by ocular, skeletal, and cardiovascular manifestations. With a combination of diligent tracking of the cardiovascular status of Marfan's patients, prophylactic aortic-root replacement, and the use of beta-adenergic-blocking agents morbidity and mortality from cardiovascular failure has decreased. The effective treatment of patients with Marfan's syndrome relies on early and accurate diagnosis. Heretofore, there has been a lack of sensitive and specific diagnostic tests for the disorder. A cause-and-effect relationship has been determined between mutations in the fibrillin gene (a glycoprotein component of the extracellular microfibril) and the Marfan's phenotype (Dietz, H. C. et al (1991) *Nature* 352:337–339).

A second class of genes, those which encode transcription factors that control the expression of cardiac myoctye genes, have also been implicated in DCM. For example, the cyclic AMP response-element binding protein (CREB) is a basic leucine-zipper nuclear transcription factor that regulates the expression of genes in response to a wide variety of extracellular signals. A dominant-negative CREB mouse model revealed a four chambered DCM phenotype closely resembling many of the anatomical, physiological, and clinical features of human Idiopathic-Dilated Cardiomyopathy (IDC) wherein monocyte numbers decreased, interstitial fibrosis occurred and impaired systolic and diastolic left ventricular function was in evidence (Fentzke R. C. et al (1998) *J Clin Invest* 101(11):2415–2426) Expression of certain "fetal" genes, which are normally repressed after embryonic development, is a common feature in cardiac hypertrophy. A transcription factor that has been implicated in cardiac function and specifically in the developmental progression of cardiac organogenesis is nuclear factor of activated T cells (NF-ATc). Studies with NF-ATc nonsense-mutation mouse models reveal that NF-ATc is required for the proper development of the pulmonary and aortic valves and septum in the heart. (de la Pompa, J. L. et al (1998) *Nature* 392:182–186.; Ranger, A. M. (1998) *Nature* 392: 186–190) NF-ATc, having translocated to the nucleus via a calcineurin mediated pathway, may be able to form a complex with a developmentally expressed transcription factor, GATA4, to activate so-called fetal genes (Molkentin, J. D. et al (1998) *Cell* 93 (2): 215–28). Geneticists have identified five additional loci associated with adult-onset autosomal dominant dilated cardiomyopathy. Soon it will be possible to correlate clinical outcome with genetic susceptibility profiles, as has been reported for patients with hypertrophic cardiomyopathy.

The immune system is a highly regulated and plastic system with a variety of stimulatory and responsive elements. One modality for the regulation of stimulus response and the subsequent exquisitely controlled response is via transcription factors which act on a variety of genes in the immune system singularly and in concert with one another. One example of such a transcription factor is nuclear factor-(kappa)B (NF-κB). This factor regulates the expression of many of the genes involved in proinflammatory pathways such as cytokines, chemokines, enzymes involved in mediating inflammation, immune receptors and adhesion molecules involved in the initial recruitment of leukocytes to sites of inflammation (Stein, B, and Baldwin, A. S. (1993) *Mol Cell Biol* 13:7191–7198; Kopp, E. B. and Ghosh, S. (1995) *Adv Immunol* 58:1–27). It plays a role in asthma, ulcerative colitis and rheumatoid arthritis by regulating the expression of the inducible gene for nitric oxide synthase (Xie, Q. W. et al (1994) *J Biol Chem* 269:4705–4708) and it modulates the onset of inflammatory disease via the regulation of cyclooxygenase-2 increasing the production of prostaglandins and thromboxanes (Yamamoto, K. et al (1995) *J Biol Chem* 270:31315–50; Crofford, L. J. et al (1994) *J Clin Invest* 93:1095–101). Changes in the expression or activation of specific oncogenes encoding transcription factors cause many leukemias characterized by particular chromosomal translocations (Rabbitts, T. H. (1994) *Nature* 372:143–9.). T-cell acute leukemias may have a variety of genes fused to their T-cell-receptor gene loci, but the fusion partners have a common function: they are almost all genes for transcription factors (Fisch, P. et al (1992) *Oncogene* 7:2389–97; Korsmeyer, S. J. (1992) *Annu Rev Immunol* 10:785–807; Cleary, M. L. (1991) *Cell* 66:619–22; Cline, M. J. (1996) *N Engl J Med* 330:328–336), for example, in acute childhood leukemia the expression of the homeobox-containing gene HOX-11 is activated by translocation to the T-cell receptor locus (Hatano, M. et al (1991) *Science* 253:79–82). The molecular characterization of the defects associated with diseases such as are stated herein point the way towards therapeutic approaches. Immunosuppressive agents such as cyclosporin and tacrolimus (FK 506) exert their effects by inhibiting specific transcription factors that are required for T-cell activation (Liu, J. et al (1991) *Cell* 66:807–15). Thus, it is clear that a greater understanding of role which transcription factors play in the immune system would lead to the determination of highly specific drug targets which would work to treat immune system disorders, such as chronic inflammatory disease.

Other embryonic developmental transcription factors play integral roles in organogenesis and tissue repair. A subset of these factors, called T-Box transcription factors, share several common features: DNA-binding and transcriptional regulatory activity; retention of conserved expression patterns between orthologs and within subfamilies; modulation of regulatory pathways; mediation of mesodermal induction as well as other inductive interactions; and some modulate embryogenesis, organogenesis, organ regeneration, and tissue repair.

The mouse Brachyury (T) gene was the first T-Box gene to be discovered (Dobrovolskaia-Zavadskaia, N. (1927) *C.R. Seanc Soc Biol* 97:114–116.) and it is by far the most studied. Recently it was identified by positional cloning (Herrmann et al. (1990) *Nature* 343:617–622.) and was found to be a murine semi-dominant mutation that caused a short tail in heterozygotes, and embryonic lethality in homozygotes. The T-protein was described as having a highly conserved DNA-binding domain known as a T-Box (Pflugfelder et al. (1992) *Biochem Biophys Res Commun* 186:918–925; Bollag et al. (1994) *Nat Genet* 7:383–389). This DNA-binding domain binds a 24 base pair palindromic element (AATTTC ACACCT AGGTGT GAAATT) and regulates transcription though two pairs of activation and repression domains (Kispert et al. (1995) *EMBO J* 14:4763–4772).

Sequence homology was found between the mouse T gene and a cloned Drosophila gene called omb (Pflugfelder et al., *Biochem Biophys Res Commun* 186:918–925, 1992). The Xenopus Brachyury (Xbra) induces different mesodermal cell types in a dose-dependent manner. (O'Reilly et al. (1995) *Development* 121:1351–1359). Expression of Xbra in Xenopus is an immediate-early response to mesoderm-inducing factors, such as members of the transforming growth factor-β (TGF-β) family and the fibroblast growth factor (FGF) family (as reviewed by Smith et al. (1995) *Semin Dev Biol* 6:405–410).

There is a high level of conservation associated with this isolated region of each member of the T-Box family. The T-Box extends across a region of 180 to 190 amino acid residues, which can be located at any position within the polypeptide (Agulnik, S. I., et al. (1996) *Genetics* 144:249–254; Agulnik et al. (1997) *Genome* 40: 458–464). Thus far, no sequence similarity has been found outside the T-Box region among different T-Box family members.

The T-Box gene family can be said to consist of several generic entities: T, Tbr-1, Tbx1–9, 11, 12, 17 and T2 and many species has been shown to contain orthologs. Several mouse T-Box genes have been reported; mu-T, mu-Thr1 (identified in a subtractive hybridization screen for genes specifically involved in regulating forebrain development (Bulfone et al. (1995) *Neuron* 15:63–78), mu-Tbx1–6, mm-Tbx13 (Wattler et al., *Genomics* 48:24–33), and mm-Tbx14 (Wattler et al. (1998) *Genomics* 48:24–33, 1998). There are four Xenopus genes (Xbra, x-eomes, x-ET and x-VegT (Zhang et al. (1996) *Development* 122:4119–4129; Smith et al. (1995) *Semin Dev Biol* 6:405–410; Lustig et al. (1996) *Development* 122:4001–4012; Stennard et al. (1996) *Development* 122:4179–4188; Horb et al. (1997) *Development* 124:1689–1698; Ryan et al. (1996) *Cell* 87:989–1000).

Human orthologs for six of eight mouse genes have been identified. Hu-T (Edwards et al. (1996) *Genome Res* 6:226–233; Morrison et al. (1996) *Hum Mol Genet* 5:669–674) and hu-TBR1 (Bulfone et al. (1995) *Neuron* 15:63–78) were found by homology with the mouse orthologs. Hu-TBX2 was isolated independently by two groups from embryonic kidney cDNA libraries (Campbell et al. (1995) *Genomics* 28:255–260; Law et al. (1995) *Mamm Genome* 6:267–277). Hu-TBX1, hu-TBX3, and hu-TBX5 were found during investigations aimed at uncovering the genetic basis of human developmental dysmorphic syndromes and were recognized as orthologs of the mouse genes by sequence homology (Li et al. (1997) *Nat Genet* 15:21–29; Basson et al. (1997) *Nat Genet* 15:30–35; Chieffo et al. (1997) *Genome* 43:267–277).

There is currently only a handful of known mutations in T-Box genes. Spontaneous mutations in hu-TBX3 (Bamshad et al. (1997) *Nat Genet* 16:311–315) and hu-TBX5 (Li et al. (1997) *Nat Genet* 15:21–29; Basson et al. (1997) *Nat Genet* 15:30–35) have been reported. These mutations at T-Box genes play a role in several human autosomal, dominant developmental syndromes: Ulnar-Mammary syndrome and Holt-Oram syndrome. Ulnar-Mammary syndrome is characterized by limb defects, abnormalities of apocrine glands such as the absence of breasts, axillary hair and perspiration, dental abnormalities such as ectopic, hypoplastic and absent canine teeth, and genital abnormalities such as micropenis, shawl scrotum and imperforate hymen. Holt-Oram syndrome is characterized by cardiac septal defects and preaxial radial ray abnormalities of the forelimbs (Li et al. (1997) *Nat Genet* 15:21–29; Basson et al. (1997) *Nat Genet* 15:30–35; Bamshad et al. (1997) *Nat Genet* 16:311–315). Mutations in the 5' end of TBX5 lead to substantial cardiovascular malformations and relatively mild skeletal defects while mutations in the 3' end of the gene cause severe skeletal malformation and have less effect on cardiac development (McCarthy, M (1998) *Lancet* 351(9115):1564; Basson, C. T. et al (1997) *Nature Genetics* 15:30–35).

A better understanding of the role which T-Box transcription factors play in embryogenesis, organogenesis and organ regeneration has been recently recognized. T-Box related genes have been found in many species, making up a large group of T-Box transcription factors which are highly conserved in their DNA-binding capacity but may be highly divergent in the non-DNA-binding regions. There are common features which define the family, as well as specific differences that define individual members. Phylogenetic analysis suggests that the genome of most animal species will have at least five T-Box genes (related to mu-Tbx2, mu-Tbx, mu-Tbx1, mu-T, and mu-Thr1). There are at least 16 distinct members in 11 different animal groups that have been reported and human orthologs of six of the eight mouse genes have already been identified. The human orthologs of the other mouse T-Box genes have yet to be revealed.

Given the importance of such T-Box DNA-binding transcription factors in proper embryogenesis, organogenesis, organ regeneration and tissue repair, there exists a need to identify other novel transcription factors which function to regulate cell differentiation, whose aberrant function can result in developmental disorders such as Ulnar-Mammary syndrome and Holt-Oram syndrome, and which can be used in the treatment of organ injury by way of regeneration and/or tissue repair such as in hibernating myocardium during myocardial ischemia. By identifying the genes that initiate and exacerbate dilated cardiomyopathy, and by assembling the gene products into biochemical pathways, therapeutic targets for new drugs and gene therapies for this disease may be discovered.

SUMMARY OF THE INVENTION

The present invention is based, at least in part, on the discovery of nucleic acid and protein molecules, referred to herein as MTbx molecules. The MTbx molecules of the present invention are useful as modulating agents in regulating a variety of cellular processes. Accordingly, in one aspect, this invention provides isolated nucleic acid molecules encoding MTbx proteins or biologically active portions thereof, as well as nucleic acid fragments suitable as primers or hybridization probes for the detection of MTbx-encoding nucleic acids.

In one embodiment, a MTbx nucleic acid molecule includes a nucleotide sequence at least about 53.9%, 54%, 55%, 60%, 65%, 70%, 75%, 80%, 85%, 90%, 95% or more homologous to the nucleotide sequence shown in SEQ ID NO:1, or the nucleotide sequence of the DNA insert of the plasmid deposited with ATCC as Accession Number 209973, or a complement thereof. In a preferred embodiment, the isolated nucleic acid molecule includes a nucleotide sequence shown in SEQ ID NO:1, or a complement thereof.

In another preferred embodiment, the nucleic acid molecule has the nucleotide sequence shown in SEQ ID NO:1. In yet another preferred embodiment, an isolated nucleic acid molecule has the nucleotide sequence of the DNA insert of the plasmid deposited with ATCC as Accession Number 209973. In another preferred embodiment, the nucleic acid molecule comprises a fragment of at least 358 nucleotides of the nucleotide sequence of SEQ ID NO:1, the DNA insert of the plasmid deposited with ATCC as Accession Number 209973, or a complement thereof.

In another preferred embodiment, an isolated nucleic acid molecule has the nucleotide sequence shown in SEQ ID NO:1, or the nucleotide sequence of the DNA insert of the plasmid deposited with ATCC as Accession Number 209973, or a complement thereof. In yet another preferred embodiment, an isolated nucleic acid molecule has the nucleotide sequence of the DNA insert of the plasmid deposited with ATCC as Accession Number 209973, or a complement thereof.

In another embodiment, a MTbx nucleic acid molecule includes a nucleotide sequence encoding a protein or polypeptide having an amino acid sequence sufficiently homologous to the amino acid sequence of SEQ ID NO:2, or the amino acid sequence encoded by the DNA insert of the plasmid deposited with ATCC as Accession Number 209973. In a preferred embodiment, a MTbx nucleic acid molecule includes a nucleotide sequence encoding a protein or polypeptide which includes an amino acid sequence at least 53.9%, 54%, 55%, 60%, 65%, 70%, 75%, 80%, 85%, 90%, 95% more homologous to the amino acid sequence of SEQ ID NO:2, or the amino acid sequence encoded by the DNA insert of the plasmid deposited with ATCC as Accession Number 209973. In another preferred embodiment, an isolated nucleic acid molecule encodes the amino acid sequence of human MTbx. In yet another preferred embodiment, the nucleic acid molecule includes a nucleotide sequence encoding a protein having the amino acid sequence of SEQ ID NO: 2, or the amino acid sequence encoded by the DNA insert of the plasmid deposited with ATCC as Accession Number 209973.

In another embodiment, an isolated nucleic acid molecule of the present invention encodes a protein, preferably a MTbx protein, which includes a T-Box DNA-binding domain. In another embodiment, an isolated nucleic acid molecule of the present invention encodes a protein, preferably a MTbx protein, which includes a MTbx C-terminal unique domain. In another embodiment, an isolated nucleic acid molecule of the present invention encodes a protein, preferably a MTbx protein, which includes a T-Box DNA-binding domain and a MTbx C-terminal unique domain. In another embodiment, an isolated nucleic acid molecule of the present invention encodes a protein, preferably a MTbx protein, which includes a T-Box DNA-binding domain and a MTbx C-terminal unique domain, and, preferably, is localized to the cytoplasm and nucleus. In yet another embodiment, a MTbx nucleic acid molecule encodes a MTbx protein and is a naturally occurring nucleotide sequence.

Another embodiment of the invention features nucleic acid molecules, preferably MTbx nucleic acid molecules, which specifically detect MTbx nucleic acid molecules relative to nucleic acid molecules encoding non-MTbx proteins. For example, in one embodiment, such a nucleic acid molecule is at least 100, preferably 100–200, more preferably 200–300, more preferably 300–400, more preferably 400–500, and even more preferably 500–517 nucleotides in length and hybridizes under stringent conditions to a nucleic acid molecule comprising the nucleotide sequence shown in SEQ ID NO:1, the nucleotide sequence of the DNA insert of the plasmid deposited with ATCC as Accession Number 209973, or a complement thereof. In preferred embodiments, the nucleic acid molecules are at least 15 (e.g., contiguous) nucleotides in length and hybridize under stringent conditions to nucleotides 355–436 or 1108–1183 of SEQ ID NO:1. In other preferred embodiments, the nucleic acid molecules include nucleotides 355–436 or 1108–1183 of SEQ ID NO:1.

In other preferred embodiments, the nucleic acid molecule encodes a naturally occurring allelic variant of a polypeptide which includes the amino acid sequence of SEQ ID NO:2, or an amino acid sequence encoded by the DNA insert of the plasmid deposited with ATCC as Accession Number 209973, wherein the nucleic acid molecule hybridizes to a nucleic acid molecule which includes SEQ ID NO:1 under stringent conditions.

Another embodiment of the invention provides an isolated nucleic acid molecule which is antisense to a MTbx nucleic acid molecules, e.g., the coding strand of a MTbx nucleic acid molecule.

Another aspect of the invention provides a vector comprising a MTbx nucleic acid molecule. In certain embodiments, the vector is a recombinant expression vector. In another embodiment, the invention provides a host cell containing a vector of the invention. The invention also provides a method for producing a protein, preferably a MTbx protein, by culturing in a suitable medium, a host cell, e.g., a mammalian host cell such as a non-human mammalian cell, of the invention containing a recombinant expression vector such that the protein is produced.

Another aspect of this invention features isolated or recombinant MTbx proteins and polypeptides. In one embodiment, an isolated protein, preferably a MTbx protein, includes aT-Box DNA-binding domain. In another embodiment, an isolated protein, preferably a MTbx protein, includes a MTbx C-terminal unique domain. In another embodiment, an isolated protein, preferably a MTbx protein, includes a T-Box DNA-binding domain and a MTbx C-terminal unique domain. In another embodiment, an isolated protein, preferably a MTbx protein, includes a T-Box DNA-binding domain and a MTbx C-terminal unique domain and is, preferably, localized to the cytoplasm and nucleus. In another embodiment, an isolated protein, preferably a MTbx protein, has an amino acid sequence sufficiently homologous to the amino acid sequence of SEQ ID NO:2, or the amino acid sequence encoded by the DNA insert of the plasmid deposited with ATCC as Accession Number 209973. In a preferred embodiment, a protein or polypeptide, preferably a MTbx protein, includes an amino acid sequence at least about 57.6%, 60%, 65%, 70%, 75%, 80%, 85%, 90%, 95% or more homologous to the amino acid sequence of SEQ ID NO:2, or the amino acid sequence encoded by the DNA insert of the plasmid deposited with ATCC as Accession Number 209973. In another preferred embodiment, a protein or polypeptide, preferably a MTbx protein, includes an amino acid sequence at least about 57.6%, 60%, 65%, 70%, 75%, 80%, 85%, 90%, 95% or more homologous to the amino acid sequence of SEQ ID NO:2 and a T-Box DNA-binding domain. In yet another preferred embodiment, a protein or polypeptide, preferably a MTbx protein, includes an amino acid sequence at least about 57.6%, 60%, 65%, 70%, 75%, 80%, 85%, 90%, 95% or more homologous to the amino acid sequence of SEQ ID NO:2 and a MTbx C-terminal unique domain. In a preferred embodiment, a protein or polypeptide, preferably a MTbx protein, includes an amino acid sequence at least about 53.9%, 54%, 55%, 60%, 65%, 70%, 75%, 80%, 85%, 90%, 95% or more homologous to the amino acid sequence of SEQ ID NO:2, a T-Box DNA-binding domain and a MTbx C-terminal unique domain.

In another embodiment, the invention features fragments of the proteins having the amino acid sequence of SEQ ID NO:2, wherein the fragment comprises at least 15 contiguous amino acids of the amino acid sequence of SEQ ID NO:2, or an amino acid or an amino acid sequence encoded by the DNA insert of the plasmid deposited with the ATCC as Accession Number 209973. In another embodiment, a protein, preferably a MTbx protein, includes the amino acid sequence of SEQ ID NO:2, or the amino acid sequence encoded by the DNA insert of the plasmid deposited with ATCC as Accession Number 209973. In yet another embodiment, the protein has the amino acid sequence SEQ ID NO:2, or the amino acid sequence encoded by the DNA insert of the plasmid deposited with ATCC as Accession Number 209973.

Another embodiment of the invention features an isolated protein, preferably a MTbx protein, which is encoded by a nucleic acid molecule which includes a nucleotide sequence at least about 53.9%, 54%, 55%, 60%, 65%, 70%, 75%, 80%, 85%, 90%, 95% or more homologous to a nucleotide sequence of SEQ ID NO:1, or a complement thereof. This invention further features an isolated protein, preferably a MTbx protein, which is encoded by a nucleic acid molecule having a nucleotide sequence which hybridizes under stringent hybridization conditions to a nucleic acid molecule comprising the nucleotide sequence of SEQ ID NO:1, or a complement thereof.

The proteins of the present invention, preferably MTbx proteins, or biologically active portions thereof, can be operatively linked to a non-MTbx polypeptide (e.g., heterologous amino acid sequences) to form fusion proteins. The invention further features antibodies, such as monoclonal or polyclonal antibodies, that specifically bind proteins of the invention, preferably MTbx proteins. In addition, the MTbx proteins or biologically active portions thereof can be incorporated into pharmaceutical compositions, which optionally include pharmaceutically acceptable carriers.

In another aspect, the present invention provides a method for detecting MTbx expression in a biological sample by contacting the biological sample with an agent capable of detecting a MTbx nucleic acid molecule, protein or polypeptide such that the presence of a MTbx nucleic acid molecule, protein or polypeptide is detected in the biological sample.

In another aspect, the present invention provides a method for detecting the presence of MTbx activity in a biological sample by contacting the biological sample with an agent capable of detecting an indicator of MTbx activity such that the presence of MTbx activity is detected in the biological sample.

In another aspect, the invention provides a method for modulating MTbx activity comprising contacting a cell capable of expressing MTbx with an agent that modulates MTbx activity such that MTbx activity in the cell is modulated. In one embodiment, the agent inhibits MTbx activity. In another embodiment, the agent stimulates MTbx activity. In one embodiment, the agent is an antibody that specifically binds to a MTbx protein. In another embodiment, the agent modulates expression of MTbx by modulating transcription of a MTbx gene or translation of a MTbx mRNA. In yet another embodiment, the agent is a nucleic acid molecule having a nucleotide sequence that is antisense to the coding strand of a MTbx mRNA or a MTbx gene.

In one embodiment, the methods of the present invention are used to treat a subject having a disorder characterized by aberrant MTbx protein or nucleic acid expression or activity by administering an agent which is a MTbx modulator to the subject. In one embodiment, the MTbx modulator is a MTbx protein. In another embodiment the MTbx modulator is a MTbx nucleic acid molecule. In yet another embodiment, the MTbx modulator is a peptide, peptidomimetic, or other small molecule. In a preferred embodiment, the disorder characterized by aberrant MTbx protein or nucleic acid expression is an immune system disease, for example, HIV, leukemia4 and chronic inflammatory disease, e.g., asthma, rheumatoid arthritis, inflammatory bowel disease and psoriasis; a developmental disorder; a cardiovascular disorder, e.g., congestive heart failure, Dilated Cardiomyopathy; or other disorder arising from improper transcriptional regulation.

In one embodiment, the methods of the present invention are used to treat a subject having a condition characterized by the loss of tissue integrity relating to disease and/or injury, such as in an immune system disease, for example, HIV, leukemia, and chronic inflammatory disease, e.g., asthma, rheumatoid arthritis, inflammatory bowel disease and psoriasis; hibernating myocardium during myocardial ischemia and Dilated Cardiomyopathy, by administering an agent which is a MTbx modulator to the subject. In one embodiment, the MTbx modulator is a MTbx protein. In another embodiment the MTbx modulator is a MTbx nucleic acid molecule. In yet another embodiment, the MTbx modulator is a peptide, peptidomimetic, or other small molecule. In a preferred embodiment, the disorder characterized by aberrant MTbx protein or nucleic acid expression is cardiovascular disorder, e.g., a disorder involving a loss in tissue integrity relating to disease and/or injury such as in an immune system disease, for example, HIV, leukemia, and chronic inflammatory disease, e.g., asthma, rheumatoid arthritis, inflammatory bowel disease and psoriasis; hibernating myocardium during myocardial ischemia and Dilated Cardiomyopathy.

The present invention also provides a diagnostic assay for identifying the presence or absence of a genetic alteration characterized by at least one of (i) aberrant modification or mutation of a gene encoding a MTbx protein; (ii) misregulation of said gene: and (iii) aberrant post-translational modification of a MTbx protein, wherein a wild-type form of said gene encodes an protein with a MTbx activity.

In another aspect the invention provides a method for identifying a compound that binds to or modulates the activity of a MTbx protein, by providing a indicator composition comprising a MTbx protein having MTbx activity, contacting the indicator composition with a test compound, and determining the effect of the test compound on MTbx activity in the indicator composition to identify a compound that modulates the activity of a MTbx protein.

Other features and advantages of the invention will be apparent from the following detailed description and claims.

BRIEF DESCRIPTION OF THE DRAWINGS

FIG. 1 depicts the cDNA sequence of human MTbx. The nucleotide sequence corresponds to nucleic acids 1 to 2491 of SEQ ID NO:1.

FIG. 2 depicts a predicted amino acid sequence of human MTbx. The amino acid sequence correspond to amino acids 1 to 517 of SEQ ID NO:2.

FIG. 3 depicts the global alignment of MTbx protein and Xenopus Eomesodermin protein (Accession No. P79944). This alignment was generated utilizing the ALIGN program with the following parameter setting: PAM120, gap penalties: –12/–4 (Myers, E, and Miller, W. (1989) "Optimal Alignments in Linear Space" CABIOS 4:11–17).

FIG. 4 depicts the global alignment of MTbx protein and human Tbr-1 protein (Accession No. Q16650). This alignment was generated utilizing the ALIGN program with the following parameter setting: PAM 120, gap penalties: –12/–4 (Myers, E, and Miller. W. (1989) "Optimal Alignments in Linear Space" CABIOS 4:11–17).

FIG. 5 depicts the global alignment of MTbx protein and Mouse Tbr-1 protein (Accession No. Q64336). This alignment was generated utilizing the ALIGN program with the following parameter setting: PAM120, gap penalties: –12/–4 (Myers, E, and Miller. W. (1989) "Optimal Alignments in Linear Space" CABIOS 4:11–17).

FIG. 6 depicts the global alignment of MTbx DNA and Xenopus Eomesodermin DNA (Accession No. U75996). This alignment was generated utilizing the ALIGN program with the following parameter setting: PAM 120, gap penalties: –12/–4 (Myers, E. and Miller, W. (1989) "Optimal Alignments in Linear Space" CABIOS 4:11–17).

FIG. 7 depicts the global alignment of MTbx DNA and Human Thr-1 DNA (Accession No. U49250). This alignment was generated utilizing the ALIGN program with the following parameter setting: PAM120, gap penalties: –12/–4 (Myers. E, and Miller, W. (1989) "Optimal Alignments in Linear Space" CABIOS 4:11–17).

FIG. 8 depicts the global alignment of MTbx DNA and Mouse Tbr-1 DNA (Accession No. U49251). This alignment was generated utilizing the ALIGN program with the following parameter setting: PAM120, gap penalties: –12/–4 (Myers. E, and Miller, W. (1989) "Optimal Alignments in Linear Space" CABIOS 4:11–17).

DETAILED DESCRIPTION OF THE INVENTION

The present invention is based, at least in part, on the discovery of novel molecules, referred to herein as MTbx nucleic acid and polypeptide molecules, which play a role in or function in a variety of cellular processes, e.g., cardiac cellular processes, for example, transcriptional regulation of gene expression involved in, for example, differentiation and stress response. In one embodiment, the MTbx molecules modulate the activity of one or more proteins involved in an immune system disease, for example, HIV, leukemia, and chronic inflammatory disease, e.g., asthma, rheumatoid arthritis, inflammatory bowel disease and psoriasis; a cardiovascular disorder, e.g., congestive heart failure, Dilated Cardiomyopathy, myocardial ischemia, for example, hibernating myocardium. In another embodiment, the MTbx molecules of the present invention are capable of modulating the transcription of genes involved in an immune system disease, for example, HIV, leukemia, and chronic inflammatory disease, e.g., asthma, rheumatoid arthritis, inflammatory bowel disease and psoriasis; a cardiovascular disorder, e.g., congestive heart failure, Dilated Cardiomyopathy, myocardial ischemia, for example, hibernating myocardium.

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondar, to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

As used herein, the term "cardiac cellular processes" includes intra-cellular or inter-cellular processes involved in the functioning of the heart. Cellular processes involved in the nutrition and maintenance of the heart, the development of the heart, or the ability of the heart to pump blood to the rest of the body are intended to be covered by this term. Such processes include, for example, cardiac muscle contraction, distribution and transmission of electrical impulses, and cellular processes involved in the opening and closing of the cardiac valves. The term "cardiac cellular processes" further includes processes such as the transcription, translation and post- translational modification of proteins involved in the functioning of the heart, e.g., myofilament specific proteins, such as troponin I, troponin T, myosin light chain 1 (MLC1), and α-actinin.

The present invention is further based on the discovery of novel molecules, referred to herein as MTbx protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

The MTbx nucleic acid molecules encode polypeptides, referred to herein as MTbx polypeptides. In one embodiment, MTbx polypeptides of the invention are involved in transcriptional regulation during early embryogenesis, organogenesis, organ regeneration, tissue repair, viral infection, and stress response. In a preferred embodiment, the MTbx polypeptides of the invention are involved in the regulation of transcription factors which are involved in early embryogenesis, organogenesis, organ regeneration, tissue repair, viral infection, and stress response.

Chromosome mapping studies reveal that the human MTbx gene maps to human chromosome 3 where CDCD-2 (cardiomyopathy, dilated, with conduction defect 2), MFS-2 (Marfan-like connective tissue disorder), and FACD (Fanconi Pancytopenia, complementation group D) reside. CDCD-2 is indicated in dilated cardiomyopathy wherein mutations in two classes of genes give rise to pathogenesis: structural genes and gene encoding transcription factors. MFS-2 is indicated in Marfan's syndrome which is a dominant heritable disorder effecting connective tissues wherein a number of conditions manifest such as ocular, skeletal and cardiovascular abnormalities. FACD is indicated in Fanconi's Anemia wherein one of the symptoms is pancytopenia arises in part from transcriptional modulation of transcription factors by reactive oxygen intermediates (ROIs). Accordingly, MTbx polypeptides of the invention may be directly or indirectly involved (e.g., by interacting with factors) in the appropriate development of cardiovascular structures as well as directly or indirectly involved (e.g., by interacting with factors) in the response of the cardiovascular system, e.g., connective tissues, to stress, e.g., mechanical and metabolic stress. Further, MTbx polypeptides of the invention may act as factors which mediate transcription factor behavior in diseases such as immune system disease, for example, HIV, leukemia, and chronic inflammatory disease, e.g., asthma, rheumatoid arthritis, inflammatory bowel disease and psoriasis; dilated cardiomyopathy; and congestive heart failure.

The MTbx nucleic acid molecule and polypeptides share sequence similarity with the Xenopus Eomesodermin (Eomes) gene and the mouse Tbr-1 gene product, respectively. Lack of a functional Xenopus Eomes homologue of the human T-Box gene causes gastrulation arrest and defective mesoderm-dependent gene activation (Ryan et al. (1996) *Cell* 87:989–1000). Accordingly, MTbx polypeptides of the invention may interact with (e.g., bind to) at least one transcription factor which is a member of the human immediate early gene family of transcription factors and, thus, may be involved in the regulation of transcriptional cascades involved in embryogenesis, organogenesis, organ regeneration, tissue repair, and stress response.

As transcription factors play a role in differentiative processes, the modulation of such elements may be useful for the recovery of tissues in the adult which have dedifferentiated in a response to a disease state. Left ventricular hypertrophy, or hibernating myocardium, occurs during chronic myocardial ischemia. The effect of this condition on the tissues can be characterized as an induction of a dedifferentiated embryonic phenotype which includes the following characteristics: a partial to complete loss of sarcomeres; an accumulation of glycogen; changes in mitochondrial size and shape; loss of lamin-A and the reorganization of nuclear chromatin and a depletion of the sarcoplasmic reticulum. Additionally, extracellular regions of the tissue structure suffer excessive infilling of type I collagen, type III collagen and fibronectin. Further, there is an increase in vimentin-positive cells (endothelial cells and fibroblasts) throughout the interstitium. These gross morphological changes to the tissue structure of the myocardium slow recovery following restoration of blood flow to those regions of the myocardium effected by chronic ventricular dysfunction. Accordingly, in one embodiment of the invention, the MTbx family of the protein and nucleic acid molecules are useful as differentiation-directed transcription factors to facilitate an efficient in situ tissue remediation treatment.

The MTbx family of protein and nucleic acid molecules may play a role in gene regulatory processes. Accordingly, the modulation of such family members may be useful for the treatment of disease arising from abnormal transcription factor behavior such as in an immune system disease, for example, HIV, leukemia, and chronic inflammatory disease, e.g., asthma, rheumatoid arthritis, inflammatory bowel disease and psoriasis. Accordingly, in one embodiment of the invention, the MTbx family of the protein and nucleic acid molecules are useful as targets for drugs effecting transcription factor function to modulate of aberrant transcription factor behavior in diseases such as those which effect the immune system, for example, HIV, leukemia, and chronic inflammatory disease, e.g., asthma, rheumatoid arthritis, inflammatory bowel disease and psoriasis.

In one embodiment of the invention, MTbx family members of the invention are identified based on the presence of at least one T-Box DNA-binding domain in the protein or corresponding nucleic acid molecule. As used herein, a "T-Box DNA-binding domain" includes a region of a protein having of an amino acid sequence of about 80–280, preferably about 100–260, more preferably about 120–240, and more preferably about 140–220, or about 160–200, or about 180–187 amino acid residues in length. Accordingly, in one embodiment, a MTbx protein includes at least one T-Box DNA-binding domain of about 187 amino acid residues. In another embodiment, a MTbx protein includes at least one T-Box DNA-binding domain of about 187 amino acid residues and includes about amino acid residues 50–238 of SEQ ID NO:2.

A T-Box DNA-binding domain is identified based on the presence of at least one, and preferably two "T-Box specific consensus sequences". As used herein, a "T-Box specific consensus sequence" includes an amino acid sequence of about 10–30, preferably about 15–25, more preferably 16–24, and more preferably about 17–23, 18, 19, 20, 21 or 22 amino acid residues in length. In one embodiment, the T-Box DNA-binding domain has a first T-Box specific consensus sequence (1): L-W-X(2)-[FC]-X(3,4)-[NT]-E-M-[LIV](2)-T-X(2)-G-[RG]-[KRQ], corresponding to SEQ ID NO:9. In another embodiment, the T-Box DNA-binding domain has a second T-Box specific consensus sequence (2): [LIVMYW]-H-[PADH]-[DEN]-[GS]-X(3)-G-X(2)-W-M-X(3)-[IVA]-X-F, corresponding to SEQ ID NO:10. In another embodiment, a MTbx protein includes both a first T-Box specific consensus sequence and a second T-Box specific consensus sequence. Accordingly, in one embodiment, a MTbx protein is human MTbx having a T-Box DNA-binding domain of about 187 amino acid residues, including a first and a second T-Box specific consensus sequence, wherein the first T-Box specific consensus sequence is about 21 amino acid residues and the second T-Box specific consensus sequence is about 20 amino acid residues. In one embodiment, a MTbx protein includes a first T-Box specific consensus sequence of about 21 amino acid residues and includes amino acid residues 138–157 of SEQ ID NO:2. In another embodiment, a MTbx protein includes a second T-Box specific consensus sequence of about 20 amino acid residues and includes amino acid residues 21–231 of SEQ ID NO:2. In yet another embodiment, a MTbx protein includes a first T-Box specific consensus sequence of about 21 amino acid residues and includes amino acid residues 138–157 of SEQ ID NO:2 and includes a second T-Box specific consensus sequence of about 20 amino acid residues and includes amino acid residues 213–231 of SEQ ID NO:2. The T-Box specific consensus sequence is further described in PROSITE Document, Accession No. PDOC00972 (http://expasy.hcuge.ch/cgi-bin/get-prodoc-entry?PDOC00972) and as PROSITE Accession No. PS01283; TBOX 1 and No. PSO 1264; TBOX 2.

The domains described herein are described according to standard Prosite Signature designation (e.g., all amino acids are indicated according to their universal single letter designation; X designates any amino acid; (n) designates an alphanumeric number of "n" amino acids, e.g., X (2) designates any 2 amino acids; and [LIV] (2) designates two of wither L, I, or V; X (3,4) designates any amino acid which appears either three or four times; and [LIVM] indicates any one of the amino acids appearing within the brackets, e.g., any one of L, I, V, or M, in the alternative, any one of Leu, Ile, Val, or Met).

In another embodiment of the invention, a MTbx family member is identified based on the presence of a MTbx C-terminal unique domain. The term "MTbx C-terminal unique domain" as used herein includes a protein domain of a MTbx protein family member which includes amino acid residues C-terminal to the C-terminus of a T-Box DNA-binding domain in the amino acid sequence of the MTbx protein, e.g., a protein domain which includes amino acid residues from the C-terminal amino acid residue of the T-Box DNA-binding domain to the N-terminal amino acid residue of the amino acid sequence of the protein. Further, as used herein, a "MTbx C-terminal unique domain" includes a protein domain which is at least about 200–300 amino acid residues in length, preferably at least about 200–450 amino acid residues in length, more preferably at least about 250–400, and more preferably at least about 300–350 or 335 amino acid residues in length, and has at least about 65%, 70%, 75%, 80%, 85%, 90%, 95% homology with the amino acid sequence of a MTbx C-terminal unique domain set forth in SEQ ID NO:2.

In another embodiment, a MTbx C-terminal unique domain has the amino acid sequence as set forth in SEQ ID NO:2. As further defined herein, a MTbx C-terminal unique domain of a MTbx protein family member, however, is not sufficiently homologous to the amino acid sequence of a member of another protein family, such as a non-T-Box DNA-binding transcription factor protein family.

In a preferred embodiment, MTbx proteins of the invention have an amino acid sequence of about 440–650 amino acid residues in length, preferably about 460–630, more preferably about 480–610, more preferably about 500–590, and even more preferably about 517 amino acid residues in length.

Isolated proteins of the present invention, preferably MTbx proteins, include an amino acid sequence sufficiently homologous to the amino acid sequence of SEQ ID NO:2 or are encoded by a nucleotide sequence which includes a nucleotide sequence sufficiently homologous to SEQ ID NO:1. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 30–40% homology, preferably 40–50% homology, more preferably 50–60%, and even more preferably 60–70%, 70–80%, or 80–90% or 95% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% or 95% homology and share a common functional activity are defined herein as sufficiently homologous.

As used interchangeably herein, a "MTbx activity", "biological activity of MTbx" or "functional activity of MTbx", refers to an activity exerted by a MTbx protein, polypeptide or nucleic acid molecule as determined in vivo, in vitro, or in situ, according to standard techniques. In one embodiment, a MTbx activity is a direct activity, such as an association with a MTbx-target molecule. As used herein, a "target molecule" is a molecule with which a MTbx protein binds or interacts in nature, such that MTbx-mediated function is achieved. A MTbx target molecule can be a MTbx protein or polypeptide of the present invention or a non-MTbx molecule. For example, a MTbx target molecule can be a non-MTbx protein molecule. Alternatively, a MTbx activity is an indirect activity, such as an activity mediated by interaction of the MTbx protein with a MTbx target molecule such that the target molecule modulates a downstream cellular activity (e.g., interaction of an MTbx molecule with a MTbx target molecule can modulate the activity of that target molecule on a transcriptional pathway).

In a preferred embodiment, a MTbx activity is at least one or more of the following activities: (i) interaction of a MTbx protein with a MTbx target molecule; (ii) interaction of a MTbx protein with a MTbx target molecule, wherein the MTbx target molecule is MTbx; (iii) interaction of a MTbx protein with a MTbx target molecule, wherein the MTbx target is a transcription factor, e.g., a transcription factor which participates in the immediate early response, a transcription factor which participates in an inflammatory response, e.g., chronic inflammatory disease, asthma, rheumatoid arthritis, ulcerative colitis; a transcription factor which participates in a stress response; (iv) interaction of a MTbx protein with a MTbx target molecule, wherein the MTbx target is a transcription factor that interacts with other transcription factors, e.g., transcription factors which participate in the immediate early response, a transcription factor which participates in an inflammatory response, e.g., chronic inflammatory disease, asthma, rheumatoid arthritis, ulcerative colitis; a transcription factor which participates in a stress response; (v) interaction of a MTbx protein with a MTbx target molecule, wherein the MTbx target is a transcription factor, for example, an immune system transcription factor, e.g., AP-1; cyclic AMP response-element binding protein (CREB); a cell cycle transcription factor, e.g., E2F; a T-Box transcription factor, e.g., Tbr, Tbx1, Tbx2, Tbx3, Tbx5, Eomes, dm-omb, x-VegT, dm-H15; (vi) interaction of a MTbx protein with a MTbx target molecule, wherein the MTbx target is a transcription factor that interacts with other transcription factors, e.g., an immune system transcription factor, e.g., AP-1; cyclic AMP response-element binding protein (CREB); a cell cycle transcription factor, e.g., E2F; T-Box transcription factor, for example, MTbx, Thr, Tbx1, Tbx2, Tbx3, Tbx5, Eomes, dm-omb, x-VegT, dm-H15; e.g., a non-T-Box transcription factor, for example, E2F; (vii) modulation of gene transcription, e.g., genes involved in mesoderm induction, cell cycle dynamics, differentiation, immune system function, e.g., T-cell function, B-cell function; (viii) modulation of gene transcription, e.g., genes involved in mesoderm induction, wherein the modulation is regulated by a Mesodermal Induction Factor (MIF), e.g., a TGFβ-family member, for example, activin; e.g., FGF, for example, FGF-4.

In yet another preferred embodiment, a MTbx activity is at least one or more of the following activities: (1) cellular regulation of cell types, e.g., immune system cells, for example, T-cells, B-cells; myocytes, mesodermal cell types, for example, dorsal, posterior, paraxial, either in vitro, in vivo or in situ; (2) regulation of development, e.g., processes immediately following onset of embryogenesis, for example, gastrulation, either in vitro, in vivo or in situ; (3) regulation of organogenesis, e.g., limb, CNS, PNS, body wall, thorax, skeletal elements, eye, heart, prostate, spleen, blood cells, small intestines, thymus, blood cells (e.g., T-cells, B-cells), small intestines, thymus, kidney, lungs, mammary gland, muscle, tail, tongue, either in vitro, in vivo or in situ; or (4) regulation of the differentiation of multipotent cells, for example, precursor or progenitor cells, in regeneration, e.g., organo and/or tissue regeneration, for example, limb, heart, liver, prostate, spleen, blood cells (e.g., T-cells, B-cells), small intestines, thymus, kidney, brain, lung, placenta, ovaries, testis, either in vitro, in vivo or in situ.

Accordingly, another embodiment of the invention features isolated MTbx proteins and polypeptides having a MTbx activity. Preferred proteins are MTbx proteins including a T-Box DNA-binding domain and, preferably, a MTbx activity. Preferred proteins are MTbx proteins including at least one, preferably two T-Box consensus sequences and, preferably, a MTbx activity. Additional preferred proteins are MTbx proteins having a MTbx C-terminal unique domain and, preferably having a MTbx activity. Additional preferred proteins are MTbx proteins including a T-Box DNA-binding domain and a MTbx C-terminal unique domain and, preferably having a MTbx activity. Additional preferred proteins are MTbx proteins including a T-Box DNA-binding domain and at least one, preferably two T-box consensus sequences and, preferably having a MTbx activity. Additional preferred proteins are MTbx proteins including a T-Box DNA-binding domain, at least one, preferably two T-box consensus sequences and, a MTbx C-terminal unique domain and, preferably having a MTbx activity. In still another preferred embodiment, the isolated protein is a MTbx protein having a T-Box DNA-binding domain, at least one, preferably two T-box consensus sequences and, a MTbx C-terminal unique domain and having a MTbx activity, and preferably, an amino acid sequence sufficiently homologous to an amino acid sequence of SEQ ID NO:2.

A human MTbx cDNA, which is approximately 2494 nucleotides in length, encodes a protein which is approximately 517 amino acid residues in length, contains a MTbx T-box DNA binding domain, including, for example, about amino acids 50–238 of SEQ ID NO:2, a T-box consensus sequence including, for example, about amino acids 138–157 of SEQ ID NO:2, a T-box consensus sequence including, for example, about amino acids 213–231 of SEQ ID NO:2, and contains a MTbx C-terminal unique domain, including, for example, about amino acids 238–517 of SEQ ID NO:2.

The nucleotide sequence of the isolated human MTbx cDNA and the predicted amino acid sequence of the human MTbx polypeptide are shown in FIG. 1 and in SEQ ID NOs: 1 and 2, respectively. A plasmid containing the full length nucleotide sequence encoding human MTbx was deposited with American Type Culture Collection (ATCC), 10801 University Boulevard, Manassas, Va. 20110-2209, on Jun. 15. 1998 and assigned Accession Number 209973. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Various aspects of the invention are described in further detail in the following subsections:

I. Isolated Nucleic Acid Molecules

One aspect of the invention pertains to isolated nucleic acid molecules that encode MTbx proteins or biologically active portions thereof, as well as nucleic acid fragments sufficient for use as hybridization probes to identify MTbx-encoding nucleic acids (e.g., MTbx mRNA) and fragments for use as PCR primers for the amplification or mutation of MTbx nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MTbx nucleic acid molecule can contain less than about 5 kb, 4kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or the nucleotide sequence of the DNA insert of the plasmid deposited with ATCC as Accession Number 209973, or a portion thereof, can be isolated using standard molecular biology techniques and the sequence information provided herein. Using all or portion of the nucleic acid sequence of SEQ ID NO:1, or the nucleotide sequence of the DNA insert of the plasmid deposited with ATCC as Accession Number 209973, as a hybridization probe, MTbx nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989).

Moreover, a nucleic acid molecule encompassing all or a portion of SEQ ID NO:1, or the nucleotide sequence of the DNA insert of the plasmid deposited with ATCC as Accession Number 209973 can be isolated by the polymerase chain reaction (PCR) using synthetic oligonucleotide primers designed based upon the sequence of SEQ ID NO:1, or the nucleotide sequence of the DNA insert of the plasmid deposited with ATCC as Accession Number 209973.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to MTbx nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human MTbx cDNA.

In another preferred embodiment, an isolated nucleic acid molecule of the invention comprises a nucleic acid molecule which is a complement of the nucleotide sequence shown in SEQ ID NO:1 or the nucleotide sequence of the DNA insert of the plasmid deposited with ATCC as Accession Number 209973, or a portion of any of these nucleotide sequences. A nucleic acid molecule which is complementary to the nucleotide sequence shown in SEQ ID NO:1 or the nucleotide sequence of the DNA insert of the plasmid deposited with ATCC as Accession Number 209973, is one which is sufficiently complementary to the nucleotide sequence shown in SEQ ID NO:1 or the nucleotide sequence of the DNA insert of the plasmid deposited with ATCC as Accession Number 209973, such that it can hybridize to the nucleotide sequence shown in SEQ ID NO:1 or the nucleotide sequence of the DNA insert of the plasmid deposited with ATCC as Accession Number 209973, thereby forming a stable duplex.

In still another preferred embodiment, an isolated nucleic acid molecule of the present invention comprises a nucleotide sequence which is at least about 30–35%, preferably about 35–40%, more preferably at least about 40–45%, more preferably at least about 45–50%, and even more preferably at least about 53.9%, 54%, 55%, 60%, 60–65%, 65–70%, 70–75%, 75–80%, 80–85%, 85–90%, or 90–95% or more homologous to the nucleotide sequences (e.g., to the entire length of the nucleotide sequence) shown in SEQ ID NO:1, or the nucleotide sequence of the DNA insert of the plasmid deposited with ATCC as Accession Number 209973, or a portion of any of these nucleotide sequences.

Moreover, the nucleic acid molecule of the invention can comprise only a portion of the nucleic acid sequence of SEQ ID NO:1 or the nucleotide sequence of the DNA insert of the plasmid deposited with ATCC as Accession Number 209973, for example a fragment which can be used as a probe or primer or a fragment encoding a biologically active portion of a MTbx protein. The nucleotide sequence determined from the cloning of the MTbx genes allows for the generation of probes and primers designed for use in identifying and/or cloning other MTbx family members, as well as MTbx homologues from other species. The probe/primer typically comprises substantially purified oligonucleotide. The oligonucleotide typically comprises a region of nucleotide sequence that hybridizes under stringent conditions to at least about 12 to 15% preferably about 20–25, more preferably about 30, 40, 50 or 75 consecutive nucleotides of a sense sequence of SEQ ID NO:1 or the nucleotide sequence of the DNA insert of the plasmid deposited with ATCC as Accession Number 209973, of an anti-sense sequence of SEQ ID NO:1 or the nucleotide sequence of the DNA insert of the plasmid deposited with ATCC as Accession Number 209973, or of a naturally occurring mutant of SEQ ID NO:1 or the nucleotide sequence of the DNA insert of the plasmid deposited with ATCC as Accession Number 209973. In an exemplary embodiment, a nucleic acid molecule of the present invention comprises a nucleotide sequence which is about 100, preferably 100–200, more preferably 200–300, more preferably 300–400, more preferably 400–500, and even more preferably 500–517 nucleotides in length and hybridizes under stringent hybridization conditions to a nucleic acid molecule of SEQ ID NO:1 or the nucleotide sequence of the DNA insert of the plasmid deposited with ATCC as Accession Number 209973.

Probes based on the MTbx nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a MTbx protein, such as by measuring a level of a MTbx-encoding nucleic acid in a sample of cells from a subject e.g., detecting MTbx mRNA levels or determining whether a genomic MTbx gene has been mutated or deleted. These probes can be used to a positionally locate mutations in an MTbx gene thereby predicting the phenotype of disease such as in Holt-Oram syndrome. Further, such probes can be designed to detect commonly occurring fused-gene sequences arising from gene translocations at the T-cell-receptor loci.

A nucleic acid fragment encoding a "biologically active portion of a MTbx protein" can be prepared by isolating a portion of the nucleotide sequence of SEQ ID NO:1, or the nucleotide sequence of the DNA insert of the plasmid deposited with ATCC as Accession Number 209973, which encodes a polypeptide having a MTbx biological activity (the biological activities of the MTbx proteins have previously been described), expressing the encoded portion of the MTbx protein (e.g., by recombinant expression in vitro) and assessing the activity of the encoded portion of the MTbx protein.

The invention further encompasses nucleic acid molecules that differ from the nucleotide sequence shown in SEQ ID NO:1 or the nucleotide sequence of the DNA insert of the plasmid deposited with ATCC as Accession Number 209973, due to degeneracy of the genetic code and thus encode the same MTbx proteins as those encoded by the nucleotide sequence shown in SEQ ID NO:1 or the nucleotide sequence of the DNA insert of the plasmid deposited with ATCC as Accession Number 209973. In another embodiment, an isolated nucleic acid molecule of the invention has a nucleotide sequence encoding a protein having an amino acid sequence shown in SEQ ID NO:2.

In addition to the MTbx nucleotide sequences shown in SEQ ID NO:1 or the nucleotide sequence of the DNA insert of the plasmid deposited with ATCC as Accession Number 209973, it will be appreciated by those skilled in the art that DNA sequence polymorphisms that lead to changes in the amino acid sequences of the MTbx proteins may exist within a population (e.g., the human population). Such genetic polymorphism in the MTbx genes may exist among individuals within a population due to natural allelic variation. As used herein, the terms "gene" and "recombinant gene" refer to nucleic acid molecules comprising an open reading frame encoding a MTbx protein, preferably a mammalian MTbx protein. Such natural allelic variations can typically result in 1–5% variance in the nucleotide sequence of a MTbx gene. Any and all such nucleotide variations and resulting amino acid polymorphisms in MTbx genes that are the result of natural allelic variation and that do not alter the functional activity of a MTbx protein are intended to be within the scope of the invention.

Moreover, nucleic acid molecules encoding other MTbx family members (e.g., MTbx-2), and thus which have a nucleotide sequence which differs from the MTbx sequences of SEQ ID NO:1 or the nucleotide sequence of the DNA insert of the plasmid deposited with ATCC as Accession Number 209973 are intended to be within the scope of the invention. For example, a MTbx-2 cDNA can be identified based on the nucleotide sequence of human MTbx. Moreover, nucleic acid molecules encoding MTbx proteins from different species, and thus which have a nucleotide sequence which differs from the MTbx sequences of SEQ ID NO:1, or the nucleotide sequence of the DNA insert of the plasmid deposited with ATCC as Accession Number 209973 are intended to be within the scope of the invention. For example, an mouse MTbx cDNA can be identified based on the nucleotide sequence of a human MTbx.

Nucleic acid molecules corresponding to natural allelic variants and homologues of the MTbx cDNAs of the invention can be isolated based on their homology to the MTbx nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15–20, 20–25, 25–30 nucleotides in length and hybridizes under stringent conditions to the nucleic acid molecule comprising the nucleotide sequence of SEQ ID NO:1, or the nucleotide sequence of the DNA insert of the plasmid deposited with ATCC as Accession Number 209973. In another embodiment, the nucleic acid is at least 30, 50, 100, 250, 300, 350, 400, 450, 500, 550, or 600 nucleotides or more in length. As used herein, the term "hybridizes under stringent conditions" is intended to describe conditions for hybridization and washing under which nucleotide sequences at least about 25%, 30%, 35%, 40%, 45%, 50%, 55%, 60%, 65%, 70%, 75%, 80%, 85%, 90%, 95% or more homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C. followed by one or more washes in 0.2× SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the MTbx sequences that may exist in the population, the skilled artisan will further appreciate that changes can be introduced by mutation into the nucleotide sequences of SEQ ID NO:1, or the nucleotide sequence of the DNA insert of the plasmid deposited with ATCC as Accession Number 209973, thereby leading to changes in the amino acid sequence of the encoded MTbx proteins, without altering the functional ability of the MTbx proteins. For example, nucleotide substitutions leading to amino acid substitutions at "non-essential" amino acid residues can be made in the sequence of SEQ ID NO:1, or the nucleotide sequence of the DNA insert of the plasmid deposited with ATCC as Accession Number 209973. A "non-essential" amino acid residue is a residue that can be altered from the wild-type sequence of MTbx (e.g., the sequence of SEQ ID NO:2) without altering the biological activity, whereas an "essential" amino acid residue is required for biological activity. For example, amino acid residues that are conserved among the MTbx proteins of the present invention, are predicted to be particularly unamenable to alteration (e.g., the ten conserved cysteines involved in forming disulfide linkages or the conserved histidine, aspartate, or serine of the active enzymatic site). Moreover, amino acid residues that are defined by the MTbx T-Box DNA-binding domain, T-Box signature consensus sequence domains and MTbx C terminal unique domain are particularly unamenable to alteration. Furthermore, additional amino acid residues that are conserved between the MTbx proteins of the present invention and other members of the T-Box superfamily or protein families containing T-Box DNA-binding domain, T-Box signature consensus sequence domains and MTbx C terminal unique domains are not likely to be amenable to alteration.

Accordingly, another aspect of the invention pertains to nucleic acid molecules encoding MTbx proteins that contain changes in amino acid residues that are not essential for activity. Such MTbx proteins differ in amino acid sequence from SEQ ID NO:2 yet retain biological activity. In one embodiment, the isolated nucleic acid molecule comprises a nucleotide sequence encoding a protein, wherein the protein comprises an amino acid sequence at least about 20%, 25%, 30%, 35%, 40%, 45%, 48%, 50%, 51%, 55%, 60%, 65%, 70%, 75%, 80%, 85%, 90%, 95% or more homologous to the amino acid sequence of SEQ ID NO:2. Preferably, the protein encoded by the nucleic acid molecule is at least about 70%, 71%, 71%, 73% or more homologous to SEQ ID NO:2, more preferably at least about 75–80% homologous to SEQ ID NO:2, even more preferably at least about 85–90% homologous to SEQ ID NO:2, and most preferably at least about 95% homologous to SEQ ID NO:2 (e.g., the entire amino acid sequence of SEQ ID NO:2).

An isolated nucleic acid molecule encoding a MTbx protein homologous to the protein of SEQ ID NO:2 can be created by introducing one or more nucleotide substitutions, additions or deletions into the nucleotide sequence of SEQ ID NO:1 or the nucleotide sequence of the DNA insert of the plasmid deposited with ATCC as Accession Number 209973, such that one or more amino acid substitutions, additions or deletions are introduced into the encoded protein. Mutations can be introduced into SEQ ID NO:1 or the nucleotide sequence of the DNA insert of the plasmid deposited with ATCC as Accession Number 209973 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a MTbx protein is preferably replaced with another amino acid residue from the same side chain family. Alternatively, in another embodiment, mutations can be introduced randomly along all or part of a MTbx coding sequence, such as by saturation mutagenesis, and the resultant mutants can be screened for MTbx biological activity to identify mutants that retain activity. Following mutagenesis of SEQ ID NO:1 or the nucleotide sequence of the DNA insert of the plasmid deposited with ATCC as Accession Number 209973, the encoded protein can be expressed recombinantly and the activity of the protein can be determined.

In a preferred embodiment, a mutant MTbx protein can be assayed for the ability to (1) regulate cellular function of cell types, e.g., immune system cells, for example, T-cells, B-cells; myocytes, mesodermal cell types, for example, dorsal, posterior, paraxial, either in vitro, in vivo or in situ; (2) regulate development, e.g., processes immediately following onset of embryogenesis, for example, gastrulation, either in vitro, in vivo or in situ; (3) regulate organogenesis, e.g., limb, CNS, PNS, body wall, thorax, skeletal elements, eye, heart, prostate, spleen, blood cells, small intestines, thymus, blood cells (e.g., T-cells, B-cells), small intestines, thymus, kidney, lungs, mammary gland, muscle, tail, tongue, either in vitro, in vivo or in situ; or (4) regulate differentiation of multipotent cells, for example, precursor or progenitor cells, in regeneration, e.g., organo and/or tissue regeneration, for example, limb, heart, liver, prostate, spleen, blood cells (e.g., T-cells, B-cells), small intestines, thymus, kidney, brain, lung, placenta, ovaries, testis, either in vitro, in vivo or in situ.

In addition to the nucleic acid molecules encoding MTbx proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MTbx coding strand, or to only a portion thereof. In one embodiment, an antisense nucleic acid molecule is antisense to a "coding region" of the coding strand of a nucleotide sequence encoding MTbx. The term "coding region" refers to the region of the nucleotide sequence comprising codons which are translated into amino acid residues (e.g., the coding region of human MTbx corresponds to ). In another embodiment, the antisense nucleic acid molecule is antisense to a "noncoding region" of the coding strand of a nucleotide sequence encoding MTbx. The term "noncoding region" refers to 5' and 3' sequences which flank the coding region that are not translated into amino acids (i.e., also referred to as 5' and 3' untranslated regions).

Given the coding strand sequences encoding MTbx disclosed herein (e.g., SEQ ID NO:1), antisense nucleic acids of the invention can be designed according to the rules of Watson and Crick base pairing. The antisense nucleic acid molecule can be complementary to the entire coding region of MTbx mRNA, but more preferably is an oligonucleotide which is antisense to only a portion of the coding or noncoding region of MTbx mRNA. For example, the antisense oligonucleotide can be complementary to the region surrounding the translation start site of MTbx mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a MTbx protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systematically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An a-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave MTbx mRNA transcripts to thereby inhibit translation of MTbx mRNA. A ribozyme having specificity for a MTbx-encoding nucleic acid can be designed based upon the nucleotide sequence of a MTbx cDNA disclosed herein (i.e., SEQ ID NO:1 or the nucleotide sequence of the DNA insert of the plasmid deposited with ATCC as Accession Number 209973). For example, a derivative of a Tetrahymena L-19 IVS RNA can be constructed in which the nucleotide sequence of the active site is complementary to the nucleotide sequence to be cleaved in a MTbx-encoding mRNA. See, e.g., Cech et al. U.S. Pat. No. 4,987,071; and Cech et al. U.S. Pat. No. 5,116,742. Alternatively, MTbx mRNA can be used to select a catalytic RNA having a specific ribonuclease activity from a pool of RNA molecules. See, e.g., Bartel, D. and Szostak, J. W. (1993) *Science* 261:1411–1418.

Alternatively, MTbx gene expression can be inhibited by targeting nucleotide sequences complementary to the regulatory region of the MTbx (e.g., the MTbx promoter and/or enhancers) to form triple helical structures that prevent transcription of the MTbx gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the MTbx nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms “peptide nucleic acids” or “PNAs” refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O’Keefe et al. PNAS 93: 14670–675.

PNAs of MTbx nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MTbx nucleic acid molecules can also be used in the analysis of single base pair mutations in a gene, (e.g., by PNA-directed PCR clamping); as ‘artificial restriction enzymes’ when used in combination with other enzymes, (e.g., S1 nucleases (Hyrup B. (1996) supra)); or as probes or primers for DNA sequencing or hybridization (Hyrup B. et al. (1996) supra; Perry-O’Keefe supra).

In another embodiment, PNAs of MTbx can be modified. (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of MTbx nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated MTbx Proteins and Anti-MTbx Antibodies

One aspect of the invention pertains to isolated MTbx proteins, and biologically active portions thereof, as well as polypeptide fragments suitable for use as immunogens to raise anti-MTbx antibodies. In one embodiment, native MTbx proteins can be isolated from cells or tissue sources by an appropriate purification scheme using standard protein purification techniques. In another embodiment, MTbx proteins are produced by recombinant DNA techniques. Alternative to recombinant expression, a MTbx protein or polypeptide can be synthesized chemically using standard peptide synthesis techniques.

An "isolated" or "purified" protein or biologically active portion thereof is substantially free of cellular material or other contaminating proteins from the cell or tissue source from which the MTbx protein is derived, or substantially free from chemical precursors or other chemicals when chemically synthesized. The language "substantially free of cellular material" includes preparations of MTbx protein in which the protein is separated from cellular components of the cells from which it is isolated or recombinantly produced. In one embodiment, the language "substantially free of cellular material" includes preparations of MTbx protein having less than about 30% (by dry weight) of non-MTbx protein (also referred to herein as a "contaminating protein"), more preferably less than about 20% of non-MTbx protein, still more preferably less than about 10% of non-MTbx protein, and most preferably less than about 5% non-MTbx protein. When the MTbx protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of MTbx protein in which the protein is separated from chemical precursors or other chemicals which are involved in the synthesis of the protein. In one embodiment, the language "substantially free of chemical precursors or other chemicals" includes preparations of MTbx protein having less than about 30% (by dry weight) of chemical precursors or non-MTbx chemicals, more preferably less than about 20% chemical precursors or non-MTbx chemicals, still more preferably less than about 10% chemical precursors or non-MTbx chemicals, and most preferably less than about 5% chemical precursors or non-MTbx chemicals.

Biologically active portions of a MTbx protein include peptides comprising amino acid sequences sufficiently homologous to or derived from the amino acid sequence of the MTbx protein, e.g., the amino acid sequence shown in SEQ ID NO:2, which include less amino acids than the full length MTbx proteins, and exhibit at least one activity of a MTbx protein. Typically, biologically active portions comprise a domain or motif with at least one activity of the MTbx protein. A biologically active portion of a MTbx protein can be a polypeptide which is, for example, 10, 25, 50, 100 or more amino acids in length.

In one embodiment, a biologically active portion of a MTbx protein comprises at least a T-Box DNA-binding domain. In another embodiment, a biologically active portion of a MTbx protein comprises at least one T-Box DNA-binding consensus domain. In another embodiment, a biologically active portion of a MTbx protein comprises at least a MTbx C terminal unique domain. In another embodiment, a biologically active portion of a MTbx protein comprises at least a T-Box DNA-binding domain and a MTbx C terminal unique domain.

It is to be understood that a preferred biologically active portion of a MTbx protein of the present invention may contain at least one of the above-identified structural domains. Another preferred biologically active portion of a MTbx protein may contain at least two of the above-identified structural domains. Moreover, other biologically active portions, in which other regions of the protein are deleted, can be prepared by recombinant techniques and evaluated for one or more of the functional activities of a native MTbx protein.

In a preferred embodiment, the MTbx protein has an amino acid sequence shown in SEQ ID NO:2. In other embodiments, the MTbx protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the MTbx protein is a protein which comprises an amino acid sequence at least about 57.6%, 60%, 65%, 70%, 75%, 80%, 85%, 90%, 95% or more homologous to the amino acid sequence of SEQ ID NO:2 and retains the functional activity of the MTbx proteins of SEQ ID NO:2, respectively. Preferably, the protein is at least about 30–35% homologous to SEQ ID NO:2, more preferably at least about 35–40% homologous to SEQ ID NO:2, even more preferably at least about 40–45% homologous to SEQ ID NO:2, and even more preferably at least about 45–50%, 50–55%, 55–60%, 60–65%, 65–70%, 70–75%, 75–80%, 80–85%, 85–90%, or 90–95% or more homologous to SEQ ID NO:2.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the MTbx amino acid sequence of SEQ ID NO:2 having 517 amino acid residues, at least 406, preferably at least 435, more preferably at least 465, even more preferably at least 494, and even more preferably at least 517 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed with the NBLAST program, score=100, wordlength=12 to obtain nucleotide sequences homologous to MTbx nucleic acid molecules of the invention. BLAST protein searches can be performed with the XBLAST program, score=50, wordlength=3 to obtain amino acid sequences homologous to MTbx protein molecules of the invention. To obtain gapped alignments for comparison purposes, Gapped BLAST can be utilized as described in Altschul et al., (1997) Nucleic Acids Research 25(17) :3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 2 or 4 can be used.

The invention also provides MTbx chimeric or fusion proteins. As used herein, a MTbx "chimeric protein" or "fusion protein" comprises a MTbx polypeptide operatively linked to a non-MTbx polypeptide. A "MTbx polypeptide" refers to a polypeptide having an amino acid sequence corresponding to MTbx, whereas a "non-MTbx polypeptide" refers to a polypeptide having an amino acid sequence corresponding to a protein which is not substantially homologous to the MTbx protein, e.g., a protein which is different from the MTbx protein and which is derived from the same or a different organism. Within a MTbx fusion protein the MTbx polypeptide can correspond to all or a portion of a MTbx protein. In a preferred embodiment, a MTbx fusion protein comprises at least one biologically active portion of a MTbx protein. In another preferred embodiment, a MTbx fusion protein comprises at least two biologically active portions of a MTbx protein. Within the fusion protein, the term "operatively linked" is intended to indicate that the MTbx polypeptide and the non-MTbx polypeptide are fused in-frame to each other. The non-MTbx polypeptide can be fused to the N-terminus or C-terminus of the MTbx polypeptide.

For example, in one embodiment, the fusion protein is a GST-MTbx fusion protein in which the MTbx sequences are fused to the C-terminus of the GST sequences. Such fusion proteins can facilitate the purification of recombinant MTbx.

In another embodiment, the fusion protein is a MTbx protein containing a heterologous signal sequence at its N-terminus. For example, the native MTbx signal sequence can be removed and replaced with a signal sequence from another protein. In certain host cells (e.g., mammalian host cells), expression and/or secretion of MTbx can be increased through use of a heterologous signal sequence.

The MTbx fusion proteins of the invention can be incorporated into pharmaceutical compositions and administered to a subject in vivo. The MTbx fusion proteins can be used to affect the bioavailability of a MTbx target molecule. Use of MTbx fusion proteins may be useful therapeutically for the treatment of an immune system disease, for example, HIV, leukemia, and chronic inflammatory disease, e.g., asthma, rheumatoid arthritis, inflammatory bowel disease and psoriasis; developmental disorders (e.g., cardiovascular disorder, e.g., Dilated Cardiomyopathy, congestive heart failure, Ulnar-Mammary syndrome and Holt-Oram syndrome) and for the remediation of the loss of tissue integrity relating to disease and/or injury, such as in hibernating myocardium during myocardial ischemia. Moreover, the MTbx-fusion proteins of the invention can be used as immunogens to produce anti-MTbx antibodies in a subject, to purify MTbx ligands and in screening assays to identify molecules which inhibit the interaction of MTbx with a MTbx target molecule.

Preferably, a MTbx chimeric or fusion protein of the invention is produced by standard recombinant DNA techniques. For example. DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A MTbx-encoding nucleic acid can be cloned into such an expression vector such that the fusion moiety is linked in-frame to the MTbx protein.

The present invention also pertains to variants of the MTbx proteins which function as either MTbx agonists (mimetics) or as MTbx antagonists. Variants of the MTbx proteins can be generated by mutagenesis, e.g., discrete point mutation or truncation of a MTbx protein. An agonist of the MTbx proteins can retain substantially the same, or a subset, of the biological activities of the naturally occurring form of a MTbx protein. An antagonist of a MTbx protein can inhibit one or more of the activities of the naturally occurring form of the MTbx protein by, for example, competitively inhibiting the protease activity of a MTbx protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MTbx protein.

In one embodiment, variants of a MTbx protein which function as either MTbx agonists (mimetics) or as MTbx antagonists can be identified by screening combinatorial libraries of mutants, e.g., truncation mutants, of a MTbx protein for MTbx protein agonist or antagonist activity. In one embodiment, a variegated library of MTbx variants is generated by combinatorial mutagenesis at the nucleic acid level and is encoded by a variegated gene library. A variegated library of MTbx variants can be produced by, for example, enzymatically ligating a mixture of synthetic oligonucleotides into gene sequences such that a degenerate set of potential MTbx sequences is expressible as individual polypeptides, or alternatively, as a set of larger fusion proteins (e.g., for phage display) containing the set of MTbx sequences therein. There are a variety of methods which can be used to produce libraries of potential MTbx variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MTbx sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a MTbx protein coding sequence can be used to generate a variegated population of MTbx fragments for screening and subsequent selection of variants of a MTbx protein. In one embodiment, a library of coding sequence fragments can be generated by treating a double stranded PCR fragment of a MTbx coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MTbx protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MTbx proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify MTbx variants (Arkin and Yourvan (1992) *PNAS* 89:7811–7815; Delgrave et al. (1993) *Protein Engineering* 6(3):327–331).

In one embodiment, cell based assays can be exploited to analyze a variegated MTbx library. For example, a library of expression vectors can be transfected into a cell line which ordinarily synthesizes and secretes MTbx. The transfected cells are then cultured such that MTbx and a particular mutant MTbx are secreted and the effect of expression of the mutant on MTbx activity in cell supernatants can be detected, e.g., by any of a number of enzymatic assays. Plasmid DNA can then be recovered from the cells which score for inhibition, or alternatively, potentiation of MTbx activity, and the individual clones further characterized.

An isolated MTbx protein, or a portion or fragment thereof, can be used as an immunogen to generate antibodies that bind MTbx using standard techniques for polyclonal and monoclonal antibody preparation. A full-length MTbx protein can be used or, alternatively, the invention provides antigenic peptide fragments of MTbx for use as immunogens. The antigenic peptide of MTbx comprises at least 8 amino acid residues of the amino acid sequence shown in SEQ ID NO:2 and encompasses an epitope of MTbx such that an antibody raised against the peptide forms a specific immune complex with MTbx. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of MTbx that are located on the surface of the protein, e.g., hydrophilic regions.

A MTbx immunogen typically is used to prepare antibodies by immunizing a suitable subject, (e.g., rabbit, goat, mouse or other mammal) with the immunogen. An appropriate immunogenic preparation can contain, for example, recombinantly expressed MTbx protein or a chemically synthesized MTbx polypeptide. The preparation can further include an adjuvant, such as Freund's complete or incomplete adjuvant, or similar immunostimulatory agent. Immunization of a suitable subject with an immunogenic MTbx preparation induces a polyclonal anti-MTbx antibody response.

Accordingly, another aspect of the invention pertains to anti-MTbx antibodies. The term "antibody" as used herein refers to immunoglobulin molecules and immunologically active portions of immunoglobulin molecules, i.e., molecules that contain an antigen binding site which specifically binds (immunoreacts with) an antigen, such as MTbx. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind MTbx. The term "monoclonal antibody" or "monoclonal antibody composition", as used herein, refers to a population of antibody molecules that contain only one species of an antigen binding site capable of immunoreacting with a particular epitope of MTbx. A monoclonal antibody composition thus typically displays a single binding affinity for a particular MTbx protein with which it immunoreacts.

Polyclonal anti-MTbx antibodies can be prepared as described above by immunizing a suitable subject with a MTbx immunogen. The anti-MTbx antibody titer in the immunized subject can be monitored over time by standard techniques, such as with an enzyme linked immunosorbent assay (ELISA) using immobilized MTbx. If desired, the antibody molecules directed against MTbx can be isolated from the mammal (e.g., from the blood) and further purified by well known techniques, such as protein A chromatography to obtain the IgG fraction. At an appropriate time after immunization, e.g., when the anti-MTbx antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy,* Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses,* Plenum Publishing Corp., New York, N.Y. (1980); E. A. Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a MTbx immunogen as described above, and the culture supernatants of the resulting hybridoma cells are screened to identify a hybridoma producing a monoclonal antibody that binds MTbx.

Any of the many well known protocols used for fusing lymphocytes and immortalized cell lines can be applied for the purpose of generating an anti-MTbx monoclonal antibody (see, e.g., G. Galfre et al. (1977) Nature 266:55052: Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind MTbx, e.g., using a standard ELISA assay.

Alternative to preparing monoclonal antibody-secreting hybridomas, a monoclonal anti-MTbx antibody can be identified and isolated by screening a recombinant combinatorial immunoglobulin library (e.g., an antibody phage display library) with MTbx to thereby isolate immunoglobulin library members that bind MTbx. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J 12:725–734; Hawkins et al. (1992) J. Mol. Biol. 226:889–896; Clarkson et al. (1991) Nature 352:624–628; Gram et al. (1992) PNAS 89:3576–3580; Garrad et al. (1991) Bio/Technology 9:1373–1377; Hoogenboom et al. (1991) Nuc. Acid Res. 19:4133–4137; Barbas et al. (1991) PNAS 88:7978–7982; and McCafferty et al, Nature (1990) 348:552–554.

Additionally, recombinant anti-MTbx antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira. et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041–1043; Liu et al. (1987) PNAS 84:3439–3443; Liu et al. (1987) J. Immunol. 139:3521–3526; Sun et al. (1987) PNAS 84:214–218; Nishimura et al. (1987) Canc. Res. 47:999–1005; Wood et al. (1985) Nature 314:446–449; and Shaw et al. (1988) J. Natl. Cancer Inst. 80:1553–1559): Morrison, S. L. (1985) Science 229:1202–1207; Oi et al. (1986) BioTechniques 4:214; Winter U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-MTbx antibody (e.g., monoclonal antibody) can be used to isolate MTbx by standard techniques, such as affinity chromatography or immunoprecipitation. An anti-MTbx antibody can facilitate the purification of natural MTbx from cells and of recombinantly produced MTbx expressed in host cells. Moreover, an anti-MTbx antibody can be used to detect MTbx protein (e.g., in a cellular lysate or cell supernatant) in order to evaluate the abundance and pattern of expression of the MTbx protein. Anti-MTbx antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a MTbx protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MTbx proteins, mutant forms of MTbx proteins, fusion proteins, etc.).

The recombinant expression vectors of the invention can be designed for expression of MTbx proteins in prokaryotic or eukaryotic cells. For example, MTbx proteins can be expressed in bacterial cells such as *E. coli,* insect cells (using baculovirus expression vectors) yeast cells or mammalian cells. Suitable host cells are discussed further in Goeddel, *Gene Expression Technology: Methods in Enymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified fusion proteins can be utilized in MTbx activity assays. (e.g., direct assays or competitive assays described in detail below), or to generate antibodies specific for MTbx proteins, for example. In a preferred embodiment, a MTbx fusion protein expressed in a retroviral expression vector of the present invention can be utilized to infect bone marrow cells which are subsequently transplanted into irradiated recipients. The pathology of the subject recipient is then examined after sufficient time has passed (e.g, six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the MTbx expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif).

Alternatively, MTbx proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular*

*Cloning: A Laboratory Manual. 2nd, ed., Cold Spring Harbor Laboratory,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MTbx mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a MTbx protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a MTbx protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a MTbx protein. Accordingly, the invention further provides methods for producing a MTbx protein using the host cells of the invention. In one embodiment, the method comprises culturing the host cell of invention (into which a recombinant expression vector encoding a MTbx protein has been introduced) in a suitable medium such that a MTbx protein is produced. In another embodiment, the method further comprises isolating a MTbx protein from the medium or the host cell.

The host cells of the invention can also be used to produce nonhuman transgenic animals. For example, in one embodiment, a host cell of the invention is a fertilized oocyte or an embryonic stem cell into which MTbx-coding sequences have been introduced. Such host cells can then be used to create non-human transgenic animals in which exogenous MTbx sequences have been introduced into their genome or homologous recombinant animals in which endogenous MTbx sequences have been altered. Such animals are useful for studying the function and/or activity of a MTbx and for identifying and/or evaluating modulators of MTbx activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous MTbx gene has been altered by homologous recombination between the endogenous gene and an exogenous DNA molecule introduced into a cell of the animal. e.g., an embryonic cell of the animal, prior to development of the animal.

A transgenic animal of the invention can be created by introducing a MTbx-encoding nucleic acid into the male pronuclei of a fertilized oocyte, e.g., by microinjection, retroviral infection, and allowing the oocyte to develop in a pseudopregnant female foster animal. The MTbx cDNA sequence of SEQ ID NO:1 can be introduced as a transgene into the genome of a non-human animal. Alternatively, a nonhuman homologue of a human MTbx gene, such as a mouse or rat MTbx gene, can be used as a transgene. Alternatively, a MTbx gene homologue, such as a MTbx-2 gene can be isolated based on hybridization to the MTbx cDNA sequences of SEQ ID NO:1, or the DNA insert of the plasmid deposited with ATCC as Accession Number 209973 (described further in subsection I above) and used as a transgene. Intronic sequences and polyadenylation signals can also be included in the transgene to increase the efficiency of expression of the transgene. A tissue-specific regulatory sequence(s) can be operably linked to a MTbx transgene to direct expression of a MTbx protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al, and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of a MTbx transgene in its genome and/or expression of MTbx mRNA in tissues or cells of the animals. A transgenic founder animal can then be used to breed additional animals carrying the transgene. Moreover, transgenic animals carrying a transgene encoding a MTbx protein can further be bred to other transgenic animals carrying other transgenes.

To create a homologous recombinant animal, a vector is prepared which contains at least a portion of a MTbx gene into which a deletion, addition or substitution has been introduced to thereby alter, e.g., functionally disrupt, the MTbx gene. The MTbx gene can be a human gene (e.g., the cDNA of ), but more preferably, is a non-human homologue of a human MTbx gene (e.g., a CDNA isolated by stringent hybridization with the nucleotide sequence of SEQ ID NO:1). For example, a mouse MTbx gene can be used to construct a homologous recombination vector suitable for altering an endogenous MTbx gene in the mouse genome. In a preferred embodiment, the vector is designed such that, upon homologous recombination, the endogenous MTbx gene is functionally disrupted (i.e., no longer encodes a functional protein; also referred to as a "knock out" vector). Alternatively, the vector can be designed such that, upon homologous recombination, the endogenous MTbx gene is mutated or otherwise altered but still encodes functional protein (e.g., the upstream regulatory region can be altered to thereby alter the expression of the endogenous MTbx protein). In the homologous recombination vector, the altered portion of the MTbx gene is flanked at its 5' and 3' ends by additional nucleic acid sequence of the MTbx gene to allow for homologous recombination to occur between the exogenous MTbx gene carried by the vector and an endogenous MTbx gene in an embryonic stem cell. The additional flanking MTbx nucleic acid sequence is of sufficient length for successful homologous recombination with the endogenous gene. Typically, several kilobases of flanking DNA (both at the 5' and 3' ends) are included in the vector (see e.g., Thomas, K. R, and Capecchi, M. R. (1987) *Cell* 51:503 for a description of homologous recombination vectors). The vector is introduced into an embryonic stem cell line (e.g., by electroporation) and cells in which the introduced MTbx gene has homologously recombined with the endogenous MTbx gene are selected (see e.g., Li, E. et al. (1992) *Cell* 69:915). The selected cells are then injected into a blastocyst of an animal (e.g., a mouse) to form aggregation chimeras (see e.g., Bradley, A, in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991 ) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. Alternatively, a cell, e.g., an embryonic stem cell, from the inner cell mass of a developing embryo can be transformed with a preferred transgene. Alternatively, a cell, e.g., a somatic cell, from a cell culture line can be transformed with a preferred transgene and induced to exit the growth cycle and enter $G_o$ phase. The cell can then be fused, e.g., through the use of electrical pulses, to an enucleated mammalian oocyte. The reconstructed oocyte is then cultured such that it develops to morula or blastocyst and then transferred to pseudopregnant female foster animal. The offspring borne of this female foster animal will be a clone of the animal from which the nuclear donor cell, e.g., the somatic cell, is isolated.

IV. Pharmaceutical Compositions

The MTbx nucleic acid molecules, MTbx proteins, and anti-MTbx antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a MTbx protein or anti-MTbx antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alpinic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

As described herein, a MTbx protein of the invention has one or more of the following activities: (i) interaction of a MTbx protein with a MTbx target molecule; (ii) interaction of a MTbx protein with a MTbx target molecule, wherein the MTbx target molecule is MTbx; (iii) interaction of a MTbx protein with a MTbx target molecule, wherein the MTbx target is a transcription factor, e.g., a transcription factor which participates in the immediate early response, a transcription factor which participates in an inflammatory response, e.g., chronic inflammatory disease, asthma, rheumatoid arthritis, ulcerative colitis; a transcription factor which participates in a stress response; (iv) interaction of a MTbx protein with a MTbx target molecule, wherein the MTbx target is a transcription factor that interacts with other transcription factors, e.g., transcription factors which participate in the immediate early response, a transcription factor which participates in an inflammatory response, e.g., chronic inflammatory disease, asthma rheumatoid arthritis, ulcerative colitis; a transcription factor which participates in a stress response; (v) interaction of a MTbx protein with a MTbx target molecule, wherein the MTbx target is a transcription factor, for example, an immune system transcription factor, e.g., AP-1; cyclic AMP response-element binding protein (CREB); a cell cycle transcription factor, e.g., E2F; a T-Box transcription factor, e.g., Tbr, Tbx1, Tbx2, Tbx3, Tbx5, Eomes, dm-omb, x-VegT, dm-H15; (vi) interaction of a MTbx protein with a MTbx target molecule, wherein the MTbx target is a transcription factor that interacts with other transcription factors, e.g., an immune system transcription factor, e.g., AP-1; cyclic AMP response-element binding protein (CREB); a cell cycle transcription factor, e.g., E2F; T-Box transcription factor, for example, MTbx, Tbr, Tbx1, Tbx2, Tbx3, Tbx5, Eomes, dm-omb, x-VegT, dm-H15; e.g., a non-T-Box transcription factor, for example, E2F; (vii) modulation of gene transcription, e.g., genes involved in mesoderm induction, cell cycle dynamics, differentiation, immune system function, e.g., T-cell function, B-cell function; (viii) modulation of gene transcription, e.g., genes involved in mesoderm induction, wherein the modulation is regulated by a Mesodermal Induction Factor (MIF), e.g., a TGFβ-family member, for example, activin; e.g., FGF, for example, FGF-4.

Further as described herein, a MTbx protein of the invention has one or more of the above activities and can thus be used in, for example, the: (1) cellular regulation of cell types, e.g., immune system cells, for example, T-cells, B-cells; myocytes, mesodermal cell types, for example, dorsal, posterior, paraxial, either in vitro, in vivo or in situ; (2) regulation of development, e.g., processes immediately following onset of embryogenesis, for example, gastrulation, either in vitro, in vivo or in situ; (3) regulation of organogenesis. e.g., limb, CNS, PNS, body wall, thorax, skeletal elements, eye, heart, prostate, spleen, blood cells, small intestines, thymus, blood cells (e.g., T-cells, B-cells), small intestines, thymus, kidney, lungs, mammary gland, muscle, tail, tongue, either in vitro, in vivo or in situ; or (4) regulation of the differentiation of multipotent cells, for example, precursor or progenitor cells, in regeneration, e.g., organo and/or tissue regeneration, for example, limb, heart, liver, prostate, spleen, blood cells (e.g., T-cells, B-cells), small intestines, thymus, kidney, brain, lung, placenta, ovaries, testis, either in vitro, in vivo or in situ. The isolated nucleic acid molecules of the invention can be used, for example, to express MTbx protein (e.g., via a recombinant expression vector in a host cell in gene therapy applications), to detect MTbx mRNA (e.g., in a biological sample) or a genetic alteration in a MTbx gene, and to modulate MTbx activity, as described further below. The MTbx proteins can be used to treat disorders characterized by insufficient or excessive production of a MTbx or MTbx target molecules. In addition, the MTbx proteins can be used to screen for naturally occurring MTbx target molecules, to screen for drugs or compounds which modulate MTbx activity, as well as to treat disorders characterized by insufficient or excessive production of MTbx protein or production of MTbx protein forms which have decreased or aberrant activity compared to MTbx wild type protein. Moreover, the anti-MTbx antibodies of the invention can be used to detect and isolate MTbx proteins, regulate the bioavailability of MTbx proteins, and modulate MTbx activity.

Accordingly one embodiment of the present invention involves a method of use (e.g., a diagnostic assay, prognostic assay, or a prophylactic/therapeutic method of treatment) wherein a molecule of the present invention (e.g., a MTbx protein, MTbx nucleic acid, or a MTbx modulator) is used, for example, to diagnose, prognose and/or treat a disease and/or condition in which any of the aforementioned activities (i.e., activities (i)–(viii) and (1)–(4) in the above paragraph) is indicated. In another embodiment, the present invention involves a method of use (e.g., a diagnostic assay, prognostic assay, or a prophylactic/therapeutic method of treatment) wherein a molecule of the present invention (e.g., a MTbx protein, MTbx nucleic acid, or a MTbx modulator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment) involve administering to a subject, preferably a human subject, a molecule of the present invention (e.g., a MTbx protein, MTbx nucleic acid, or a MTbx modulator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a MTbx protein, MTbx nucleic acid, or a MTbx modulator).

A. Screening Assays

The invention provides a method (also referred to herein as a "screening assay") for identifying modulators, i.e., candidate or test compounds or agents (e.g., peptides, peptidomimetics, small molecules or other drugs) which bind to MTbx proteins, have a stimulatory or inhibitory effect on, for example, MTbx expression or MTbx activity, or have a stimulatory or inhibitory effect on, for example, the activity of an MTbx target molecule.

In one embodiment, the invention provides assays for screening candidate or test compounds which are target molecules of a MTbx protein or polypeptide or biologically active portion thereof. In another embodiment, the invention provides assays for screening candidate or test compounds which bind to or modulate the activity of a MTbx protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409). plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a MTbx protein or biologically active portion thereof is contacted with a test compound and the ability of the test compound to modulate MTbx activity determined. Determining the ability of the test compound to modulate MTbx activity can be accomplished by monitoring the bioactivity of the MTbx protein or biologically active portion thereof. The cell, for example, can be of mammalian origin or a yeast cell. Determining the ability of the test compound to modulate MTbx activity can be accomplished, for example, by coupling the MTbx protein or biologically active portion thereof with a radioisotope or enzymatic label such that binding of the MTbx protein or biologically active portion thereof to its cognate target molecule can be determined by detecting the labeled MTbx protein or biologically active portion thereof in a complex. For example, compounds (e.g., MTbx protein or biologically active portion thereof) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., MTbx protein or biologically active portion thereof) to interact with its cognate target molecule without the labeling of any of the interactants. For example, a microphysiometer can be used to detect the interaction of a compound with its cognate target molecule without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a MTbx protein or biologically active portion thereof, with a target molecule to form an assay mixture, contacting the assay mixture with a test compound, and determining the ability of the test compound to modulate the activity of the MTbx protein or biologically active portion thereof, wherein determining the ability of the test compound to modulate the activity of the MTbx protein or biologically active portion thereof, comprises determining the ability of the test compound to modulate a biological activity of the MTbx expressing cell (e.g., determining the ability of the test compound to modulate transcriptional regulation, protein:protein interactions, or protein:DNA interactions).

In another preferred embodiment, the assay comprises contacting a cell which is responsive to a MTbx protein or biologically active portion thereof, with a MTbx protein or biologically-active portion thereof, to form an assay mixture, contacting the assay mixture with a test compound, and determining the ability of the test compound to modulate the activity of the MTbx protein or biologically active portion thereof, wherein determining the ability of the test compound to modulate the activity of the MTbx protein or biologically active portion thereof comprises determining the ability of the test compound to modulate a biological activity of the MTbx-responsive cell (e.g., determining the ability of the test compound to modulate transcriptional regulation, protein:protein interactions, or protein:DNA interactions).

In another embodiment, an assay is a cell-based assay comprising contacting a cell expressing a MTbx target molecule with a test compound and determining the ability of the test compound to modulate (e.g, stimulate or inhibit) the activity of the MTbx target molecule. Determining the ability of the test compound to modulate the activity of a MTbx target molecule can be accomplished, for example, by determining the ability of the MTbx protein to bind to or interact with the MTbx target molecule.

Determining the ability of the MTbx protein to bind to or interact with a MTbx target molecule can be accomplished by one of the methods described above for determining direct binding. In a preferred embodiment, determining the ability of the MTbx protein to bind to or interact with a MTbx target molecule can be accomplished by determining the activity of the target molecule. For example, the activity of the target molecule can be determined by detecting induction of transcription of immediate early response genes. For example, the activity of the target molecule can be determined by detecting induction of a cellular second messenger of the target (i.e, intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, transcriptional regulation, protein:protein interactions, or protein:DNA interactions.

In yet another embodiment, an assay of the present invention is a cell-free assay in which a MTbx protein or biologically active portion thereof is contacted with a test compound and the ability of the test compound to bind to the MTbx protein or biologically active portion thereof is determined. Binding of the test compound to the MTbx protein can be determined either directly or indirectly as described above. In a preferred embodiment, the assay includes contacting the MTbx protein or biologically active portion thereof with a known compound which binds MTbx (e.g., a MTbx target molecule) to form an assay mixture, contacting the assay mixture with a test compound, and determining the ability of the test compound to interact with a MTbx protein, wherein determining the ability of the test compound to interact with a MTbx protein comprises determining the ability of the test compound to preferentially bind to MTbx or biologically active portion thereof as compared to the known compound.

In another embodiment, the assay is a cell-free assay in which a MTbx protein or biologically active portion thereof is contacted with a test compound and the ability of the test compound to modulate (e.g., stimulate or inhibit) the activity of the MTbx protein or biologically active portion thereof is determined. Determining the ability of the test compound to modulate the activity of a MTbx protein can be accomplished, for example, by determining the ability of the MTbx protein to bind to a MTbx target molecule by one of the methods described above for determining direct binding. Determining the ability of the MTbx protein to bind to a MTbx target molecule can also be accomplished using a technology such as real-time Biomolecular Interaction Analysis (BIA). Sjolander, S, and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a MTbx protein can be accomplished by determining the ability of the MTbx protein to further modulate the activity of a downstream effector (e.g., a transcriptionally activated immediate early response pathway component) of a MTbx target molecule. For example, the activity of the effector molecule on an appropriate target can be determined or the binding of the effector to an appropriate target can be determined as previously described.

In yet another embodiment, the cell-free assay involves contacting a MTbx protein or biologically active portion thereof with a known compound which binds the MTbx protein to form an assay mixture, contacting the assay mixture with a test compound, and determining the ability of the test compound to interact with the MTbx protein, wherein determining the ability of the test compound to interact with the MTbx protein comprises determining the ability of the MTbx protein to preferentially bind to or modulate the activity of a MTbx target molecule.

The cell-free assays of the present invention are amenable to use of both soluble and/or membrane-bound forms of isolated proteins (e.g. MTbx proteins or biologically active portions thereof or receptors to which MTbx targets bind). In the case of cell-free assays in which a membrane-bound form of an isolated protein is used (e.g., a cell surface receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide Triton® X-100, Triton® X-114, Thesit®, Isotridecypoly(ethylene glycol ether)$_n$, 3-[(3-cholamidopropyl)dimethylamminio]-1-propane sulfonate (CHAPS), 3 -[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either MTbx or its target molecule to facilitate separation of complexed from uncomplexed forms of one or both of the proteins, as well as to accommodate automation of the assay. Binding of a test compound to a MTbx protein, or interaction of a MTbx protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ MTbx fusion proteins or glutathione-S-transferaseltarget fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or MTbx protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of MTbx binding or activity determined using standard techniques.

Other techniques for immobilizing proteins on matrices can also be used in the screening assays of the invention. For example, either a MTbx protein or a MTbx target molecule can be immobilized utilizing conjugation of biotin and streptavidin. Biotinylated MTbx protein or target molecules can be prepared from biotin-NHS (N-hydroxysuccinimide) using techniques well known in the art (e.g., biotinylation kit. Pierce Chemicals, Rockford, Ill.), and immobilized in the wells of streptavidin-coated 96 well plates (Pierce Chemical). Alternatively, antibodies reactive with MTbx protein or target molecules but which do not interfere with binding of the MTbx protein to its target molecule can be derivatized to the wells of the plate, and unbound target or MTbx protein trapped in the wells by antibody conjugation. Methods for detecting such complexes, in addition to those described above for the GST-immobilized complexes, include immunodetection of complexes using antibodies reactive with the MTbx protein or target molecule, as well as enzyme-linked assays which rely on detecting an enzymatic activity associated with the MTbx protein or target molecule.

In another embodiment, modulators of MTbx expression are identified in a method wherein a cell is contacted with a candidate compound and the expression of MTbx mRNA or protein in the cell is determined. The level of expression of MTbx mRNA or protein in the presence of the candidate compound is compared to the level of expression of MTbx mRNA or protein in the absence of the candidate compound. The candidate compound can then be identified as a modulator of MTbx expression based on this comparison. For example, when expression of MTbx mRNA or protein is greater (statistically significantly greater) in the presence of the candidate compound than in its absence, the candidate compound is identified as a stimulator of MTbx mRNA or protein expression. Alternatively, when expression of MTbx mRNA or protein is less (statistically significantly less) in the presence of the candidate compound than in its absence, the candidate compound is identified as an inhibitor of MTbx mRNA or protein expression. The level of MTbx mRNA or protein expression in the cells can be determined by methods described herein for detecting MTbx mRNA or protein.

In yet another aspect of the invention, the MTbx proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al (1993) *Oncogene* 8:1693–1696; and Brent WO94/10300), to identify other proteins, which bind to or interact with MTbx ("MTbx-binding proteins" or "MTbx-bp") and are involved in MTbx activity. Such MTbx-binding proteins are also likely to be involved in the propagation of signals by the MTbx proteins or MTbx targets as, for example, downstream elements of a MTbx-mediated signaling pathway. Alternatively, such MTbx-binding proteins are likely to be MTbx inhibitors.

The two-hybrid system is based on the modular nature of most transcription factors, which consist of separable DNA-binding and activation domains. Briefly, the assay utilizes two different DNA constructs. In one construct, the gene that codes for a MTbx protein is fused to a gene encoding the DNA binding domain of a known transcription factor (e.g., GAL4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a MTbx-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MTbx protein.

This invention further pertains to novel agents identified by the above-described screening assays and to processes for producing such agents by use of these assays. Accordingly, in one embodiment, the present invention includes a compound or agent obtainable by a method comprising the steps of any one of the aformentioned screening assays (e.g., cell-based assays or cell-free assays). For example, in one embodiment, the invention includes a compound or agent obtainable by a method comprising contacting a cell which expresses a MTbx target molecule with a test compound and the determining the ability of the test compound to bind to, or modulate the activity of, the MTbx target molecule. In another embodiment, the invention includes a compound or agent obtainable by a method comprising contacting a cell which expresses a MTbx target molecule with a MTbx protein or biologically-active portion thereof, to form an assay mixture, contacting the assay mixture with a test compound, and determining the ability of the test compound to interact with, or modulate the activity of, the MTbx target molecule. In another embodiment, the invention includes a compound or agent obtainable by a method comprising contacting a MTbx protein or biologically active portion thereof with a test compound and determining the ability of the test compound to bind to, or modulate (e.g., stimulate or inhibit) the activity of, the MTbx protein or biologically active portion thereof. In yet another embodiment, the present invention included a compound or agent obtainable by a method comprising contacting a MTbx protein or biologically active portion thereof with a known compound which binds the MTbx protein to form an assay mixture, contacting the assay mixture with a test compound, and determining the ability of the test compound to interact with, or modulate the activity of the MTbx protein.

Accordingly, it is within the scope of this invention to further use an agent identified as described herein in an appropriate animal model. For example, an agent identified as described herein (e.g., a MTbx modulating agent, an antisense MTbx nucleic acid molecule, a MTbx-specific antibody, or a MTbx-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a MTbx target molecule is contacted with a test compound and the ability of the test compound to bind to, or modulate the activity of, the MTbx target molecule is determined. In another exemplary embodiment, the present invention includes a method of synthesizing or producing a drug or pharmaceutical composition based on the structure and/or properties of a compound obtainable by a method in which a MTbx protein or biologically active portion thereof is contacted with a test compound and the ability of the test compound to bind to, or modulate (e.g., stimulate or inhibit) the activity of, the MTbx protein or biologically active portion thereof is determined.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the MTbx nucleotide sequences, described herein, can be used to map the location of the MTbx genes on a chromosome. The mapping of the MTbx sequences to chromosomes is an important first step in correlating these sequences with genes associated with disease.

Briefly, MTbx genes can be mapped to chromosomes by preparing PCR primers (preferably 15–25 bp in length) from the MTbx nucleotide sequences. Computer analysis of the MTbx sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the MTbx sequences will yield an amplified fragment. The MTbx gene has been mapped to position 3p23–24 in the human genome and to syntenic chromosome mo9,14.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the MTbx nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the MTbx gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The MTbx sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the MTbx nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The MTbx nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, can comfortably provide positive individual identification with a panel of perhaps 10 to 1,000 primers which each yield a noncoding amplified sequence of 100 bases. If predicted coding sequences, such as those in are used, a more appropriate number of primers for positive individual identification would be 500–2,000.

If a panel of reagents from MTbx nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial MTbx Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e, another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the MTbx nucleotide sequences or portions thereof, e.g., fragments derived from the noncoding regions of SEQ ID NO:1, having a length of at least 20 bases, preferably at least 30 bases.

The MTbx nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such MTbx probes can be used to identify tissue by species and/or by organ type.

In a similar fashion, these reagents, e.g., MTbx primers or probes can be used to screen tissue culture for contamination (i.e, screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining MTbx protein and/or nucleic acid expression as well as MTbx activity, in the context of a biological sample (e.g., blood, serum, cells, tissue) to thereby determine whether an individual is afflicted with a disease or disorder, or is at risk of developing a disorder, associated with aberrant MTbx expression or activity. The invention also provides for prognostic (or predictive) assays for determining whether an individual is at risk of developing a disorder associated with MTbx protein, nucleic acid expression or activity. For example, mutations in a MTbx gene can be assayed in a biological sample.

In one embodiment, assays for detecting mutations in the human MTbx gene enable the prediction of a phenotype of a particular genotypic profile of a specific mutation. Whereas in Holt-Oram syndrome the siting of a mutation in one portion of the TBX5 gene relates to a preponderance of cardiac abnormalities over skeletal abnormalities, the presence of a mutation in another region of the TBX5 gene gives rise to lesser cardiac abnormalities and more severe skeletal abnormalities. Further, a missense mutation in TBX5 gives rise to a severe phenotype wherein both skeletal and cardiac abnormalities are extensive. Similarly, assays for mutations in specific portions of the MTbx gene may allow the prediction of a phenotype associated with a particular disease or disorder.

Such assays can be used for prognostic or predictive purpose to thereby phophylactically treat an individual prior to the onset of a disorder characterized by or associated with MTbx protein, nucleic acid expression or activity.

Another aspect of the invention pertains to monitoring the influence of agents (e.g., drugs, compounds) on the expression or activity of MTbx in clinical trials.

These and other agents are described in further detail in the following sections.

1. Diagnostic Assays

An exemplary method for detecting the presence or absence of MTbx protein or nucleic acid in a biological sample involves obtaining a biological sample from a test subject and contacting the biological sample with a compound or an agent capable of detecting MTbx protein or nucleic acid (e.g., mRNA, genomic DNA) that encodes MTbx protein such that the presence of MTbx protein or nucleic acid is detected in the biological sample. A preferred agent for detecting MTbx mRNA or genomic DNA is a labeled nucleic acid probe capable of hybridizing to MTbx mRNA or genomic DNA. The nucleic acid probe can be, for example, a full-length MTbx nucleic acid, such as the nucleic acid of SEQ ID NO:1 (or that of, or the DNA insert of the plasmid deposited with ATCC as Accession Number 209973, or a portion thereof), such as an oligonucleotide of at least 15, 30, 50, 100, 250 or 500 nucleotides in length and sufficient to specifically hybridize under stringent conditions to MTbx mRNA or genomic DNA. Other suitable probes for use in the diagnostic assays of the invention are described herein.

A preferred agent for detecting MTbx protein is an antibody capable of binding to MTbx protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect MTbx mRNA, protein, or genomic DNA in a biological sample in vitro as well as in vivo. For example, in vitro techniques for detection of MTbx mRNA include Northern hybridizations and in situ hybridizations. In vitro techniques for detection of MTbx protein include enzyme linked immunosorbent assays (ELISAs), Western blots, immunoprecipitations and immunofluorescence. In vitro techniques for detection of MTbx genomic DNA include Southern hybridizations. Furthermore, in vivo techniques for detection of MTbx protein include introducing into a subject a labeled anti-MTbx antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting MTbx protein, mRNA, or genomic DNA, such that the presence of MTbx protein, mRNA or genomic DNA is detected in the biological sample, and comparing the presence of MTbx protein, mRNA or genomic DNA in the control sample with the presence of MTbx protein, mRNA or genomic DNA in the test sample.

The invention also encompasses kits for detecting the presence of MTbx in a biological sample. For example, the kit can comprise a labeled compound or agent capable of detecting MTbx protein or mRNA in a biological sample; means for determining the amount of MTbx in the sample; and means for comparing the amount of MTbx in the sample with a standard. The compound or agent can be packaged in a suitable container. The kit can further comprise instructions for using the kit to detect MTbx protein or nucleic acid.

2. Prognostic Assays

The diagnostic methods described herein can furthermore be utilized to identify subjects having or at risk of developing a disease or disorder associated with aberrant MTbx expression or activity. For example, the assays described herein, such as the preceding diagnostic assays or the following assays, can be utilized to identify a subject having or at risk of developing a disorder associated with MTbx protein, nucleic acid expression or activity such as an immune system disease, for example, HIV, leukemia, and chronic inflammatory disease, e.g., asthma, rheumatoid arthritis, inflammatory bowel disease and psoriasis; a cardiovascular disease, for example, Dilated Cardiomyopathy and congestive heart failure; an autosomal, dominant developmental syndrome, for example, Ulnar-Mammary syndrome, e.g., limb defects, abnormalities of apocrine glands such as the absence of breasts, axillary hair and perspiration, dental abnormalities such as ectopic, hypoplastic and absent canine teeth, and genital abnormalities such as micropenis, shawl scrotum and imperforate hymen; and Holt-Oram syndrome, e.g., cardiac septal defects and preaxial radial ray abnormalities of the forelimbs. Thus, the present invention provides a method for identifying a disease or disorder associated with aberrant MTbx expression or activity in which a test sample is obtained from a subject and MTbx protein or nucleic acid (e.g., mRNA, genomic DNA) is detected, wherein the presence of MTbx protein or nucleic acid is diagnostic for a subject having or at risk of developing a disease or disorder associated with aberrant MTbx expression or activity. As used herein, a "test sample" refers to a biological sample obtained from a subject of interest. For example, a test sample can be a biological fluid (e.g., serum), cell sample, or tissue.

In one embodiment, the present invention pertains to a method for detecting the presence of a mutation in a nucleic acid encoding an MTbx polypeptide in which a sample comprising nucleic acid molecules is contacted with a nucleic acid probe comprising at least 10, 15, 20, 25, 30, 40, 50 or more contiguous nucleotides of SEQ ID NO:1 or a complement thereof; and wherein hybridization of the nucleic acid probe with a nucleic acid molecule encoding a MTbx polypeptide is detected, thereby detecting the presence of a mutation in a nucleic acid encoding an MTbx polypeptide.

In another embodiment, the present invention describes a method for detecting the presence of a mutation in a MTbx polypeptide in which a sample comprising nucleic acid molecules is contacted with a first and a second amplification primer, said first primer comprising at least 10, 15, 20, 25, 30, 40, 50 or more contiguous nucleotides of SEQ ID NO:1 and said second primer comprising at least 10 contiguous nucleotides from a complement of SEQ ID NO:1. The sample is incubated under conditions suitable for nucleic acid amplification; and amplification of a nucleic acid molecule encoding a MTbx polypeptide is detected, thereby detecting the presence of a mutation in a nucleic acid encoding an MTbx polypeptide.

In one embodiment, the present invention describes a method wherein said probe is labeled. In another embodiment, the present invention describes a method wherein said detecting is by agarose gel electrophoresis and southern blotting. In yet another embodiment, the present invention describes a method wherein said detecting is by agarose gel electrophoresis and northern blotting. In another embodiment, the present invention describes the method wherein said detecting is by in situ hybridization. In another embodiment, the present invention describes the method wherein said sample comprising nucleic acid molecules is subjected to agarose gel electrophoresis after said incubation step. In another embodiment, the present invention describes the method wherein said nucleic acid probe or primer hybridizes to mRNA in said sample.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant MTbx expression or activity. For example, such methods can be used to determine whether a subject can be effectively treated with an agent for an immune system disease, for example, HIV, leukemia, and chronic inflammatory disease, e.g., asthma, rheumatoid arthritis, inflammatory bowel disease and psoriasis; Dilated Cardiomyopathy; congestive heart failure; Ulnar-Mammary, or Holt-Oram syndrome. Further, such methods can be used to determine whether a subject can be effectively treated with an agent for the remediation of the loss of tissue integrity due to disease and/or injury such as in an immune system disease, for example, HIV, leukemia, and chronic inflammatory disease, e.g., asthma, rheumatoid arthritis, inflammatory bowel disease and psoriasis; idiopathic dilated cardiomyopathy and in hibernating myocardium during myocardial ischemia. Thus, the present invention provides methods for determining whether a subject can be effectively treated with an agent for a disorder associated with aberrant MTbx expression, for the modulation of aberrant transcription factor behavior an immune system disease, for example, HIV, leukemia, and chronic inflammatory disease, e.g., asthma, rheumatoid arthritis, inflammatory bowel disease and psoriasis; remediation of the loss of tissue integrity due to disease and/or injury such as in hibernating myocardium during myocardial ischemia or activity in which a test sample is obtained and MTbx protein or nucleic acid expression or activity is detected (e.g., wherein the abundance of MTbx protein or nucleic acid expression or activity is diagnostic for a subject that can be administered the agent to treat a disorder associated with aberrant MTbx expression or activity.)

The methods of the invention can also be used to detect genetic alterations in a MTbx gene, thereby determining if a subject with the altered gene is at risk for a disorder characterized by aberrant developmental progression. In preferred embodiments, the methods include detecting, in a sample of cells from the subject, the presence or absence of a genetic alteration characterized by at least one of an alteration affecting the integrity of a gene encoding a MTbx-protein, or the mis-expression of the MTbx gene. For example, such genetic alterations can be detected by ascertaining the existence of at least one of 1) a deletion of one or more nucleotides from a MTbx gene; 2) an addition of one or more nucleotides to a MTbx gene; 3) a substitution of one or more nucleotides of a MTbx gene, 4) a chromosomal rearrangement of a MTbx gene; 5) an alteration in the level of a messenger RNA transcript of a MTbx gene, 6) aberrant modification of a MTbx gene, such as of the methylation pattern of the genomic DNA, 7) the presence of a non-wild type splicing pattern of a messenger RNA transcript of a MTbx gene, 8) a non-wild type level of a MTbx-protein, 9) allelic loss of a MTbx gene, and 10) inappropriate post-translational modification of a MTbx-protein. As described herein, there are a large number of assay techniques known in the art which can be used for detecting alterations in a MTbx gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the MTbx-gene (see Abravaya et al. (1995) *Nucleic Acids Res*. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a MTbx gene under conditions such that hybridization and amplification of the MTbx-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a MTbx gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MTbx can be identified by hybridizing a sample and control nucleic acids, e.g., DNA or RNA, to high density arrays containing hundreds or thousands of oligonucleotides probes (Cronin, M. T. et al. (1996) *Human Mutation* 7:244–255; Kozal, M. J. et al. (1996) *Nature Medicine* 2:753–759). For example, genetic mutations in MTbx can be identified in two dimensional arrays containing light-generated DNA probes as described in Cronin, M. T. et al, supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MTbx gene and detect mutations by comparing the sequence of the sample MTbx with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the MTbx gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type MTbx sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad. Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in MTbx cDNAs obtained from samples of cells. For example, the mutY enzyme of *E. coli* cleaves A at G/A mismatches and the thymidine DNA glycosylase from HeLa cells cleaves T at G/A mismatches (Hsu et al. (1994) *Carcinogenesis* 15:1657–1662). According to an exemplary embodiment, a probe based on a MTbx sequence, e.g., a wild-type MTbx sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in MTbx genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) *Genet Anal Tech Appl* 9:73–79). Single-stranded DNA fragments of sample and control MTbx nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a MTbx gene.

Furthermore, any cell type or tissue in which MTbx is expressed may be utilized in the prognostic assays described herein.

3. Monitoring of Effects During Clinical Trials

Monitoring the influence of agents (e.g., drugs, compounds) on the expression or activity of a MTbx protein (e.g., modulation of transcriptional activation) can be applied not only in basic drug screening, but also in clinical trials. For example, the effectiveness of an agent determined by a screening assay as described herein to increase MTbx gene expression, protein levels, or upregulate MTbx activity, can be monitored in clinical trials of subjects exhibiting decreased MTbx gene expression, protein levels, or downregulated MTbx activity. Alternatively, the effectiveness of an agent determined by a screening assay to decrease MTbx gene expression, protein levels, or downregulate MTbx activity, can be monitored in clinical trials of subjects exhibiting increased MTbx gene expression, protein levels, or upregulated MTbx activity. In such clinical trials, the expression or activity of a MTbx gene, and preferably, other genes that have been implicated in, for example, a developmental disorder can be used as a "read out" or markers of the phenotype of a particular cell.

For example, and not by way of limitation, genes, including MTbx, that are modulated in cells by treatment with an agent (e.g., compound, drug or small molecule) which modulates MTbx activity (e.g., identified in a screening assay as described herein) can be identified. Thus, to study the effect of agents on proliferative disorders, for example, in a clinical trial, cells can be isolated and RNA prepared and analyzed for the levels of expression of MTbx and other genes implicated in an immune system disease, for example, HIV, leukemia, and chronic inflammatory disease, e.g., asthma, rheumatoid arthritis, inflammatory bowel disease and psoriasis; dilated cardiomyopathy; congested heart failure; a developmental disorder and remediation of tissue damage. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of MTbx or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a MTbx protein, mRNA, or genomic DNA in the preadministration sample; (iii) obtaining one or more post-administration samples from the subject; (iv) detecting the level of expression or activity of the MTbx protein, mRNA, or genomic DNA in the post-administration samples; (v) comparing the level of expression or activity of the MTbx protein, mRNA, or genomic DNA in the pre-administration sample with the MTbx protein, mRNA, or genomic DNA in the post administration sample or samples; and (vi) altering the administration of the agent to the subject accordingly. For example, increased administration of the agent may be desirable to increase the expression or activity of MTbx to higher levels than detected, i.e., to increase the effectiveness of the agent. Alternatively, decreased administration of the agent may be desirable to decrease expression or activity of MTbx to lower levels than detected, i.e, to decrease the effectiveness of the agent. According to such an embodiment, MTbx expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder or having a disorder associated with aberrant MTbx expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MTbx molecules of the present invention or MTbx modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant MTbx expression or activity, by administering to the subject a MTbx or an agent which modulates MTbx expression or at least one MTbx activity. Subjects at risk for a disease which is caused or contributed to by aberrant MTbx expression or activity can be identified by, for example, any or a combination of diagnostic or prognostic assays as described herein. Administration of a prophylactic agent can occur prior to the manifestation of symptoms characteristic of the MTbx aberrancy, such that a disease or disorder is prevented or, alternatively, delayed in its progression. Depending on the type of MTbx aberrancy, for example, a MTbx, MTbx agonist or MTbx antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating MTbx expression or activity for therapeutic purposes. Accordingly, in an exemplary embodiment, the modulatory method of the invention involves contacting a cell with a MTbx or agent that modulates one or more of the activities of MTbx protein activity associated with the cell. An agent that modulates MTbx protein activity can be an agent as described herein, such as a nucleic acid or a protein, a naturally-occurring target molecule of a MTbx protein, a MTbx antibody, a MTbx agonist or antagonist, a peptidomimetic of a MTbx agonist or antagonist, or other small molecule. In one embodiment, the agent stimulates one or more MTbx activities. Examples of such stimulatory agents include active MTbx protein and a nucleic acid molecule encoding MTbx that has been introduced into the cell. In another embodiment, the agent inhibits one or more MTbx activities. Examples of such inhibitory agents include anti-sense MTbx nucleic acid molecules, anti-MTbx antibodies, and MTbx inhibitors. These modulatory methods can be performed in vitro (e.g., by culturing the cell with the agent), in vivo (e.g., by administering the agent to a subject), or alternatively in situ (e.g., at the site of lesion or injury, for example, in the heart, e.g., left ventricle). As such, the present invention provides methods of treating an individual afflicted with a disease or disorder characterized by aberrant expression or activity of a MTbx protein or nucleic acid molecule as in an immune system disease, for example, HIV, leukemia, and chronic inflammatory disease, e.g., asthma, rheumatoid arthritis, inflammatory bowel disease and psoriasis, as well as loss of tissue integrity relating to disease and/or injury such as in idiopathic Dilated Cardiomyopathy and in hibernating myocardium during myocardial ischemia. In one embodiment, the method involves administering an agent (e.g., an agent identified by a screening assay described herein), or combination of agents that modulates (e.g., upregulates or downregulates) MTbx expression or activity. In another embodiment, the method involves administering a MTbx protein or nucleic acid molecule as therapy to compensate for reduced or aberrant MTbx expression or activity.

Stimulation of MTbx activity is desirable in situations in which MTbx is abnormally downregulated and/or in which increased MTbx activity is likely to have a beneficial effect. For example, stimulation of MTbx activity is desirable in situations in which a MTbx is downregulated and/or in which increased MTbx activity is likely to have a beneficial effect. Likewise, inhibition of MTbx activity is desirable in situations in which MTbx is abnormally upregulated and/or in which decreased MTbx activity is likely to have a beneficial effect.

3. Pharmacogenomics

The MTbx molecules of the present invention, as well as agents, or modulators which have a stimulatory or inhibitory effect on MTbx activity (e.g., MTbx gene expression) as identified by a screening assay described herein can be administered to individuals to treat (prophylactically or therapeutically) disorders (e.g., an immune system disease, for example, HIV, leukemia, and chronic inflammatory disease, e.g., asthma, rheumatoid arthritis, inflammatory bowel disease and psoriasis, idiopathic Dilated Cardiomyopathy, congestive heart failure, Ulnar-Mammary syndrome, and Holt-Oram syndrome) associated with aberrant MTbx activity. Additionally, the MTbx molecules of the present invention, as well as agents, or modulators which have a stimulatory or inhibitory effect on MTbx activity (e.g., MTbx gene expression) as identified by a screening assay described herein can be administered to individuals to treat (prophylactically or therapeutically) an immune system disease, for example, HIV, leukemia, and chronic inflammatory disease, e.g., asthma, rheumatoid arthritis, inflammatory bowel disease and psoriasis; or a loss of tissue integrity relating to disease and/or injury such as in hibernating myocardium during myocardial ischemia. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a MTbx molecule or MTbx modulator as well as tailoring the dosage and/or therapeutic regimen of treatment with a MTbx molecule or MTbx modulator.

Pharmacogenomics deals with clinically significant hereditary variations in the response to drugs due to altered drug disposition and abnormal action in affected persons. See e.g., Eichelbaum, M., *Clin Exp Pharmacol Physiol,* 1996, 23(10–11):983–985 and Linder, M. W., *Clin Chem,* 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a MTbx protein or MTbx receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a MTbx molecule or MTbx modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a MTbx molecule or MTbx modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1
Identification and Characterization of Human MTbx cDNA

In this example, the identification and characterization of the gene encoding human MTbx is described.

Isolation of the Human MTbx cDNA

The invention is based, at least in part, on the discovery of a human gene encoding a novel protein, referred to herein as MTbx. The human MTbx was isolated from a cDNA library which was prepared from tissue obtained from a subject suffering from class IV ischemic cardiomyopathy. Briefly, a cardiac tissue sample was obtained from a biopsy of a 54 year old white male suffering from class IV ischemic cardiomyopathy, mRNA was isolated from the cardiac tissue and a cDNA library was prepared therefrom using art known methods (described in, for example, *Molecular Cloning A Laboratory Manual,* 2nd Ed., ed, by Sambrook, Fritsch and Maniatis (Cold Spring Harbor Laboratory Press: 1989).

A single, MTbx cDNA clone was obtained with the Marathon RACE protocol and reagents available commercially through Clontech Laboratories. Inc. RACE, or rapid amplification of cDNA ends, is useful to isolate a PCR fragment comprising the native 3' or 5' end of a cDNA open reading frame, and involves use of one or more gene-specific sense (for 3' RACE) or antisense (for 5' RACE) oligonucleotide primers. The RACE protocol used is generally as described in Siebert et al. (1995), 23 *Nucl. Acids Res.* 1087–1088, and in the Clontech, Inc. *User Manual for Marathon-Ready cDNA* (1996), the teachings of which are incorporated herein by reference. The RACE reagents included the Advantage KlenTaq Polymerase mix, 10× PCR reaction buffer, 50× dNTP mix and Tricine-EDTA buffer commercially available from Clontech, Inc. The protocol is practiced with 0.5 mL PCR reaction tubes and a thermal cycling device such as the DNA Thermal Cycler 480 available from Perkin-Elmer Corporation.

A plurality of nested, MTbx specific primers (antisense oligonucleotides, 5'-AAAAACACCACCAAGTCCATCTGC-3' (SEQ ID NO:7); 5'-GCATCAAGGTGGAAGGCAAACATC-3' (SEQ ID NO:8)) each 24 bp (base-pairs) in length, were prepared for use in a 5'-RACE protocol to amplify a PCR product comprising the 5' end of the MTbx open reading frame in a HUMVEC Marathon-Ready cDNA preparation. Thermal cycling was carried out according to the manufacturer's recommended Program 1 (a 94° C. hot start followed by 5 cycles at 94° C. to 72° C., then 5 cycles at 94° C. to 70° C., then 20–25 cycles at 94° C. to 68° C.). Confirmation that additional MTbx gene sequence has been obtained can be produced by routine Southern blot analysis or by subcloning and sequencing.

The present 1.7 kb 5'-RACE product also is useful to produce a full-length MTbx cDNA by long-distance PCR (generally as described in Barnes (1994), 91 *Proc. Natl. Acad. Sci. USA* 2216–2220, and Cheng et al. (1994), 91 *Proc. Natl. Acad. Sci. USA* 5695–5699) or by subcloning according to established techniques. The long-distance PCR technique involves the use of oligonucleotides corresponding to the native 5' and 3' ends of the MTbx gene ORF in a hot start cycling program commencing at 94° C., followed by 25 cycles at 94° C. to 68° C. Electrophoretic resolution of the amplified long-distance PCR product is expected to yield a single cDNA encoding a full-length MTbx polypeptide. The alternative subcloning technique capitalizes on the presence, if any, of overlapping sequence between the 5'-RACE product and the M154 cDNA insert. Exploitation of a restriction site, if present in the overlapping region, allows joining of overlapping partial cDNAs by T4 ligase to produce a single cDNA corresponding to expressed cellular MTbx.

Clones from this library were sequenced and compared to a proprietary sequence database for homology. A clone designated M154 was found to have 57.6% nucleotide homology to Xenopus T-box Eomesodermin DNA. The sequence of the entire clone was determined, was found to contain an open reading frame of 517 amino acids and was termed MTbx. SEQ ID NO:5 and SEQ ID NO:6 contain nucleotides and amino acid residues identical to those found in SEQ ID NO:1 and SEQ ID NO:2 disclosed in U.S. patent application Ser. No. 09/163,116, filed Sep. 29, 1998, in U.S. Provisional application Ser. No. 60/089,467, filed Jun. 16, 1998, and in SEQ ID NO:5 and SEQ ID NO:6 of U.S. patent application XX/XXX,XXX (MNI-046CP2), filed Nov. 9, 1998.

The nucleotide sequence encoding the human MTbx protein is shown in FIG. 1 and is set forth as SEQ ID NO:1. The full length protein encoded by this nucleic acid comprises about 517 amino acids and has the amino acid sequence shown in FIG. 1 and set forth as SEQ ID NO:2. Notable features of the human MTbx protein include a T-Box DNA-binding domain (about amino acids 50–238 of SEQ ID NO:2) consisting of two T-Box consensus sequence regions (about amino acids 138–157 and 213–231 of SEQ ID NO:2), a MTbx C-terminal unique domain (about amino acids 239–517 of SEQ ID NO:2). The clone comprising the entire coding region of human MTbx was deposited with the American Type Culture Collection (ATCC®), 10801 University Boulevard, Manassas, Va. 20110-2209, on Jun. 15, 1998, and assigned Accession Number 209973.

Analysis of Human MTbx

A BLAST search (Altschul et al. (1990) *J. Mol. Biol.* 215:403) of the nucleotide and protein sequences of human MTbx revealed that MTbx is similar to the following proteins: Xenopus Eomesodermin protein (protein: Accession No. P79944, DNA: Accession No. U75996), Mouse Thr-1 protein (protein: Accession No. Q64336, DNA: Accession No. U49250) and human Thr-1 protein (protein: Accession No. Q16650, DNA: Accession No. U49251). These DNAs are approximately 53.9% identical (over MTbx nucleic acids 1–2494), 42.6% identical (over MTbx nucleic acids 1–2494) to MTbx, and 49.7% identical (over MTbx nucleic acids 1–2494) to MTbx, respectively, at the nucleic acid level. Protein and DNA alignments were generated utilizing the ALIGN program with the following parameter setting: PAM120, gap penalties: −12/−4 (Myers. E, and Miller, W. (1989) "Optimal Alignments in Linear Space" CABIOS 4:11–17). A global alignment of MTbx protein and a Xenopus Eomesodermin protein is shown in FIG. 3. A global alignment of MTbx protein and human Tbr1 protein is shown in FIG. 4. A global alignment of MTbx protein and mouse Thr1 protein is shown in FIG. 5. A global alignment of MTbx DNA and Xenopus Eomesodermin DNA is shown in FIG. 6. A global alignment of MTbx DNA and human Tbr1 DNA is shown in FIG. 7. An alignment of MTbx DNA and mouse Tbr1 DNA is shown in FIG. 8.

Tissue Distribution of MTbx mRNA

This Example describes the tissue distribution of MTbx mRNA, as determined by Northern blot hybridization.

Northern blot hybridizations with the various RNA samples are performed under standard conditions and washed under stringent conditions, i.e., 0.2× SSC at 65° C. A DNA probe corresponding to the coding region of MTbx is used. The DNA is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Example 2

Chromosomal Localization of the Human MTbx Gene

The MTbx gene was mapped to chromosome 3p23-p24 by PCR typing of the Genebridge (G4) radiation hybrid panel (Research Genetics, Inc., Huntsville, Ala.). Typing of the DNA and comparison to radiation hybrid map data at the Whitehead Institute Center for Genome Research (WICGR) linked the MTbx gene to CDCD2, cardiomyopathy, dilated, with conduction defect2; MFS2, Marfan-like connective tissue disorder; and FACD, Fanconi Pancytopenia, complementation group D, on human chromosome 3.

As the panels used in the mapping studies included both human and hamster sequences, the two primers to be used in the mapping of the MTbx gene were tested to confirm that they were specific for human DNA rather than hamster DNA. Primers were designed from 3' UTR sequence of M154. The MTbx primers used in the PCR mapping studies were: forward AAGATACTAGGCCCAGGAGTC (SEQ ID NO:3) and reverse TCCTGAGTCCCACTGGCC (SEQ ID NO:4) were first tested on human and hamster cell line DNA for specific amplification. Each PCR reaction consisted of: 5 µl (10 ng) genomic DNA, 1.5 µl primers (6.6 µM each), 1.5 µl 10× PCR buffer (15 mM MgCl$_2$, 100 mM Tris-HCl, 500 mM KCl Perkin-Elmer, CoMTbx., Norwalk, Conn.), 5 u Taq polymerase (0.05 u/µl Perkin-Elmer AmpliTaq (Hot Start)., Norwalk, Conn.), and 1.2 µl Pharmacia dNTP mix (2.5 mM). Reactions were thermocycled on a Perkin-Elmer 9600 for 95° C. for 2 min Hot Start, 94° C. 40 sec, 55° C. 40 sec., 72° C., 40 sec., 35 cycles. Resulting PCR products were run out on a 2% agarose gel, post-stained with SYBR Gold (1:10,000 dil in 1× TBE), and scanned on a Molecular Dynamics 595 Fluorimager. The primers specifically amplified a 175 bp product from control human cell line DNA and a product of approximately 150 bp from control Hamster cell line DNA. These primers were used to amplify the 93 DNAs in duplicate from the Genebridge4 Radiation Hybrid Panel.

After the primers to be used in the mapping studies were determined to be specific for human DNA, the radiation hybrid mapping studies were performed as follows: PCR reactions of radiation hybrid panels, GeneBridge 4 (Research Genetics. Inc., Huntsville. Ala.), were assembled in duplicate using an automated PCR assembly program on a Hamilton Microlab 2200 robot. Each PCR reaction consisted of: 5 µl (10 ng) genomic DNA, 1.5 µl primers (6.6 µM each), 1.5 µl 10× PCR buffer (15 mM MgCl$_2$, 100 mM Tris-HCl, 500 mM KCl Perkin- Elmer, CoMTbx., Norwalk, Conn.), 5 u Taq polymerase (0.05 u/µl Perkin-Elmer AmpliTaq (Hot Start), Norwalk, Conn.), and 1.2 µl Pharmacia dNTP mix (2.5 mM). Reactions were thermocycled on a Perkin-Elmer 9600 for 95° C. for 2 min Hot Start, 94° C. 40 sec, 55° C. 40 sec., 72° C., 40 sec., 35 cycles. Resulting PCR products were run out on a 2% agarose gel, post-stained with SYBR Gold (1:10,000 dil in 1× TBE), and scanned on a Molecular Dynamics 595 Fluorimager.

Positive hybrids for the Genebridge 4 panel were: 1, 9, 11, 18, 19, 20, 21, 27, 28, 32, 37, 41, 44, 45, 46, 47, 49, 52, 55, 62, 63, 65, 70, 72, 74, 85, 89, 90, 92, and 93. The following Genebridge4 hybrid DNAs were scored as questionable: 36 and 68, and the remaining DNAs were scored as negative (no human band amplified). RH linkage analysis was performed using the Map Manager QTb21 software package, m154 was found to map 5.2 cR$_{3000}$ telomeric to the Whitehead Institute framework marker AFM319XG5, and 20.4 cR$_{3000}$ centromeric of the Whitehead Institute framework marker WI-9313. LOD scores for linkage were 20.3 for AFM319XG5, and 13.3 for WI-9313.

Example 3

Expression of Recombinant MTbx Protein in Bacterial Cells

In this example, MTbx is expressed as a recombinant glutathione-S-transferase (GST) fusion polypeptide in *E. coli* and the fusion polypeptide is isolated and characterized. Specifically, MTbx is fused to GST and this fusion polypeptide is expressed in *E. coli,* e.g., strain PEB 199. As the human MTbx protein is predicted to be approximately 26 kDa, and GST is predicted to be 26 kDa, the fusion polypeptide is predicted to be approximately 52 kDa, in molecular weight. Expression of the GST-MTbx fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4
Expression of Recombinant MTbx Protein in COS Cells

To express the MTbx gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire MTbx protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the MTbx DNA sequence is amplified by PCR using two primers. The 5' primer contains the restriction site of interest followed by approximately twenty nucleotides of the MTbx coding sequence starting from the initiation codon; the 3' end sequence contains complementary sequences to the other restriction site of interest, a translation stop codon, the HA tag or FLAG tag and the last 20 nucleotides of the MTbx coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the MTbx gene is inserted in the correct orientation. The ligation mixture is transformed into *E. coli* cells (strains HBO101, DH5a SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the MTbx-pcDNA/Amp plasmid DNA using the calcium phosphate or calcium chloride co-precipitation methods. DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual, 2nd, ed., Cold Spring Harbor Laboratory,* Cold Spring Harbor Laboratory Press, Cold Spring Harbor, N.Y., 1989. The expression of the MTbx polypeptide is detected by radiolabelling ($^{35}$S-methionine or $^{35}$S-cysteine available from NEN, Boston, Mass., can be used) and immunoprecipitation (Harlow, E, and Lane, D. *Antibodies: A Laboratory Manual,* Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the MTbx coding sequence is cloned directly into the polylinker of the pcDNA/Amp vector using the appropriate restriction sites. The resulting plasmid is transfected into COS cells in the manner described above, and the expression of the MTbx polypeptide is detected by radiolabelling and immunoprecipitation using an MTbx specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated mammalian T-box transcription factor polypeptide encoded by a nucleic acid molecule which hybridizes to a complement of a nucleic acid molecule comprising SEQ ID NO:1 at 6× SSC at 45° C., followed by one or more washes in 0.2× SSC, 0.1% SDS at 50–65° C.

2. An isolated mammalian T-box transcription factor polypeptide comprising an amino acid sequence which is at least 90% identical to the amino acid sequence of SEQ ID NO:2, wherein said percent identity is calculated using the ALIGN program for comparing amino acid sequences, a PAM 120 weight residue table, a gap length penalty of 12, and a gap penalty of 4.

3. An isolated mammalian T-box transcription factor polypeptide which is encoded by a nucleic acid molecule comprising a nucleotide sequence having 1–5% variance as compared to the nucleotide sequence of SEQ ID NO:1, wherein said 1–5% variance results in an amino acid substitution at a non-essential amino acid residue of the polypeptide.

4. An isolated mammalian T-box transcription factor polypeptide comprising the amino acid sequence of SEQ ID NO:2 within which a conservative amino acid substitution has been made.

5. An isolated mammalian T-box transcription factor which is encoded by the nucleotide sequence contained in the plasmid deposited with ATCC® as Accession Number 209973 or a complement thereof.

6. An isolated mammalian T-box transcription factor polypeptide encoded by a nucleic acid molecule which hybridizes to a complement of a nucleic acid molecule consisting of SEQ ID NO:1 at 6× SSC at 45° C., followed by one or more washes in 0.2× SSC, 0.1% SDS at 50–65° C.

7. An isolated mammalian T-box transcription factor polypeptide consisting of an amino acid sequence which is at least 90% identical to the amino acid sequence of SEQ ID NO:2, wherein said percent identity is calculated using the ALIGN program for comparing amino acid sequences, a PAM120 weight residue table, a gap length penalty of 12, and a gap penalty of 4.

8. An isolated mammalian T-box transcription factor polypeptide which is encoded by a nucleic acid molecule consisting of a nucleotide sequence having 1–5% variance as compared to the nucleotide sequence of SEQ ID NO:1, wherein said 1–5% variance results in an amino acid substitution at a non-essential amino acid residue of the polypeptide.

9. An isolated mammalian T-box transcription factor polypeptide consisting of the amino acid sequence of SEQ ID NO:2 within which a conservative amino acid substitution has been made.

10. An isolated polypeptide comprising at least 15 consecutive amino acid residues of the amino acid sequence of SEQ ID NO:2 or SEQ ID NO:6.

11. An isolated polypeptide comprising the amino acid sequence of SEQ ID NO:2.

12. An isolated polypeptide consisting of the amino acid sequence of SEQ ID NO:2.

13. An isolated polypeptide comprising the amino acid sequence of SEQ ID NO:6.

14. An isolated polypeptide consisting of the amino acid sequence of SEQ ID NO:6.

15. An isolated polypeptide comprising at least 50 consecutive amino acid residues of the amino acid sequence of SEQ ID NO:2.

16. An isolated polypeptide comprising at least 50 consecutive amino acid residues of the amino acid sequence of SEQ ID NO:6.

17. An isolated fusion polypeptide comprising the polypeptide of any one of claims 1–5, 11, 13, 15, or 16, operatively linked to a heterologous polypeptide.

* * * * *

UNITED STATES PATENT AND TRADEMARK OFFICE
CERTIFICATE OF CORRECTION

PATENT NO.: 6,031,078

DATED: Febraury 29, 2000

INVENTOR(S): Mehran Khodadoust

It is certified that error appears in the above-identified patent and that said Letters Patent is hereby corrected as shown below:

On the title page, lines 1-2: delete "MTBX Protein and Nucleic Acid Molecules And Uses Therefor" and insert -- Novel MTBX Polypeptides And Uses Therefor --

Claim 1: line 61, delete "." after "45°C"

Claim 6: line 10, delete "." after "45°C"

Delete Claim 10, and renumber claims 11-14 accordingly.

Signed and Sealed this

Thirteenth Day of February, 2001

NICHOLAS P. GODICI

*Attest:*

*Attesting Officer*  Acting Director of the United States Patent and Trademark Office

SEQUENCE LISTING

```
<160> NUMBER OF SEQ ID NOS: 10

<210> SEQ ID NO 1
<211> LENGTH: 2494
<212> TYPE: DNA
<213> ORGANISM: Homo sapiens
<220> FEATURE:
<221> NAME/KEY: CDS
<222> LOCATION: (164)..(1714)

<400> SEQUENCE: 1
catggacagc ctgagctccg agcggtacta cctccagtcc cccggtcctc aggggtcgga      60
gctggctgcg ccctgctcac tcttcccgta ccaggcggcg gctggggcgc cccacggacc     120
tgtgtacccg gctcctaacg ggcgcgcta cccctacggc tcc atg ctg ccc ccc        175
                                               Met Leu Pro Pro
                                                 1 ggc ggc ttc ccc gcg gct gtg tgc cca ccc ggg agg gcg cag ttc ggc       223
Gly Gly Phe Pro Ala Ala Val Cys Pro Pro Gly Arg Ala Gln Phe Gly
  5                  10                  15                  20 cca gga gcc ggt gcg ggc agt ggc gcg ggc ggt agc agc ggc ggg ggc       271
Pro Gly Ala Gly Ala Gly Ser Gly Ala Gly Gly Ser Ser Gly Gly Gly
                 25                  30                  35 ggc ggc ccg ggc acc tat cag tac aag cca ggg ggc tcc gct cta cgg       319
```

```
Gly Gly Pro Gly Thr Tyr Gln Tyr Lys Pro Gly Gly Ser Ala Leu Arg
             40                  45                  50 gcc cgt acc ctg gag ccc gca gcg gga tct tgc gga gga ctg ggg      367
Ala Arg Thr Leu Glu Pro Ala Ala Gly Ser Cys Gly Gly Leu Gly
         55                  60                  65 ggc ctg ggg gtt cca ggt tct ggc ttc cgt gcc cac gtc tac ctg tgc  415
Gly Leu Gly Val Pro Gly Ser Gly Phe Arg Ala His Val Tyr Leu Cys
 70                  75                  80 aac cgg cct ctg tgg ctc aaa ttc cac cgc cac caa act gag atg atc  463
Asn Arg Pro Leu Trp Leu Lys Phe His Arg His Gln Thr Glu Met Ile
 85                  90                  95                 100 att acg aaa cag ggc agg cgc atg ttt cct ttc ttg agc ttc aac ata  511
Ile Thr Lys Gln Gly Arg Arg Met Phe Pro Phe Leu Ser Phe Asn Ile
             105                 110                 115 aac gga ctc aat ccc act gcc cac tac aat gtg ttc gta gag gtg gtg  559
Asn Gly Leu Asn Pro Thr Ala His Tyr Asn Val Phe Val Glu Val Val
             120                 125                 130 ctg gcg gac ccc aac cac tgg cgc ttc cag ggg ggc aaa tgg gtg acc  607
Leu Ala Asp Pro Asn His Trp Arg Phe Gln Gly Gly Lys Trp Val Thr
             135                 140                 145 tgt ggc aaa gcc gac aat aac atg cag ggc aac aaa atg tat gtt cac  655
Cys Gly Lys Ala Asp Asn Asn Met Gln Gly Asn Lys Met Tyr Val His
150                 155                 160 cca gag tct cct aat act ggt tcc cac tgg atg aga cag gag att tca  703
Pro Glu Ser Pro Asn Thr Gly Ser His Trp Met Arg Gln Glu Ile Ser
165                 170                 175                 180 ttc ggg aaa tta aaa ctc acc aat aac aaa ggc gca aat aac aac aac  751
Phe Gly Lys Leu Lys Leu Thr Asn Asn Lys Gly Ala Asn Asn Asn Asn
             185                 190                 195 acc cag atg ata gtc tta caa tcc tta cac aaa tac caa ccc cga ctg  799
Thr Gln Met Ile Val Leu Gln Ser Leu His Lys Tyr Gln Pro Arg Leu
             200                 205                 210 cat att gtt gaa gtt aca gag gat ggc gtg gag gac ttg aat gag ccc  847
His Ile Val Glu Val Thr Glu Asp Gly Val Glu Asp Leu Asn Glu Pro
             215                 220                 225 tca aag acc cag act ttt acc ttc tca gaa acg caa ttc att gca gtg  895
Ser Lys Thr Gln Thr Phe Thr Phe Ser Glu Thr Gln Phe Ile Ala Val
             230                 235                 240 act gcc tac caa aac acc gat att act caa cta aag att gat cat aac  943
Thr Ala Tyr Gln Asn Thr Asp Ile Thr Gln Leu Lys Ile Asp His Asn
245                 250                 255                 260 ccc ttt gca aaa ggc ttc aga gac aac tat gat tcc atg tac acc gct  991
Pro Phe Ala Lys Gly Phe Arg Asp Asn Tyr Asp Ser Met Tyr Thr Ala
             265                 270                 275 tca gaa aat gac agg tta act cca tct ccc acg gat tct cct aga tcc  1039
Ser Glu Asn Asp Arg Leu Thr Pro Ser Pro Thr Asp Ser Pro Arg Ser
             280                 285                 290 cat cag att gtc cct gga ggt cgg tac ggc gtt caa tcc ttc ttc ccg  1087
His Gln Ile Val Pro Gly Gly Arg Tyr Gly Val Gln Ser Phe Phe Pro
             295                 300                 305 gag ccc ttt gtc aac act tta cct caa gcc cgc tat tat aat ggc gag  1135
Glu Pro Phe Val Asn Thr Leu Pro Gln Ala Arg Tyr Tyr Asn Gly Glu
             310                 315                 320 aga acc gtg cca cag acc aac ggc ctc ctt tca ccc caa cag agc gaa  1183
Arg Thr Val Pro Gln Thr Asn Gly Leu Leu Ser Pro Gln Gln Ser Glu
325                 330                 335                 340 gag gtg gcc aac cct ccc cag cgg tgg ctt gtc acg cct gtc cag caa  1231
Glu Val Ala Asn Pro Pro Gln Arg Trp Leu Val Thr Pro Val Gln Gln
             345                 350                 355
```

-continued

| | | |
|---|---|---|
| cct ggg acc aac aaa cta gac atc agt tcc tat gaa tct gaa tat act<br>Pro Gly Thr Asn Lys Leu Asp Ile Ser Ser Tyr Glu Ser Glu Tyr Thr<br>360 365 370 | 1279 | |
| tct agc aca ttg ctc cca tat ggc att aaa tcc ttg ccc ctt cag aca<br>Ser Ser Thr Leu Leu Pro Tyr Gly Ile Lys Ser Leu Pro Leu Gln Thr<br>375 380 385 | 1327 | |
| tcc cat gcc ctg ggg tat tac cca gac cca acc ttt cct gca atg gca<br>Ser His Ala Leu Gly Tyr Tyr Pro Asp Pro Thr Phe Pro Ala Met Ala<br>390 395 400 | 1375 | |
| ggg tgg gga ggt cga ggt tct tac cag agg aag atg gca gct gga cta<br>Gly Trp Gly Gly Arg Gly Ser Tyr Gln Arg Lys Met Ala Ala Gly Leu<br>405 410 415 420 | 1423 | |
| cca tgg acc tcc aga aca agc ccc act gtg ttc tct gaa gat cag ctc<br>Pro Trp Thr Ser Arg Thr Ser Pro Thr Val Phe Ser Glu Asp Gln Leu<br>425 430 435 | 1471 | |
| tcc aag gag aaa gtg aaa gag gaa att ggc tct tct tgg ata gag aca<br>Ser Lys Glu Lys Val Lys Glu Glu Ile Gly Ser Ser Trp Ile Glu Thr<br>440 445 450 | 1519 | |
| ccc cct tcc atc aaa tct cta gat tcc aat gat tca gga gta tac acc<br>Pro Pro Ser Ile Lys Ser Leu Asp Ser Asn Asp Ser Gly Val Tyr Thr<br>455 460 465 | 1567 | |
| agt gct tgt aag cga agg cgg ctg tct cct agc aac tcc agt aat gaa<br>Ser Ala Cys Lys Arg Arg Arg Leu Ser Pro Ser Asn Ser Ser Asn Glu<br>470 475 480 | 1615 | |
| aat tca ccc tcc ata aag tgt gag gac att aat gct gaa gag tat agt<br>Asn Ser Pro Ser Ile Lys Cys Glu Asp Ile Asn Ala Glu Glu Tyr Ser<br>485 490 495 500 | 1663 | |
| aaa gac acc tca aaa ggc atg gga ggg tat tat gct ttt tac aca act<br>Lys Asp Thr Ser Lys Gly Met Gly Gly Tyr Tyr Ala Phe Tyr Thr Thr<br>505 510 515 | 1711 | |
| ccc taaagagtta ttttaacctc aaaaattagc taactttttg cagatggact<br>Pro | 1764 | |
| tggtggtgtt ttttgttgtc ttctttgcct aggtkgccaa aaagawgttk gccttccacc | 1824 | |
| ttgatgcwtc ctgktttkgtg caattctcta aaagaaggtg ccaaagcttt ttgattgctg | 1884 | |
| caggtaactg aaacaaacct agcatttttw aaaaattarg attaatggaa gcctttaagg | 1944 | |
| attttaaatt cgaagggatc caaggttctg tatttatctt attggggaga cactaacmmt | 2004 | |
| tcaaagaagc aggctgtgaa cattgggtgc ccagtgctat cagatgagtt aaaacctttg | 2064 | |
| attctcattt ctatttgtaa attcttaagc aaatagaagc cgagtgttaa ggtgttttgc | 2124 | |
| ttctgaaaga gggctgtgcc ttccgtttca gaaggagaca ttttgctgtt acattctgcc | 2184 | |
| aggggcaaaa gatactaggc ccaggagtca agaaaagctt ttgtgaaagt gatagtttca | 2244 | |
| cctgactttg attccttaac ccccggcttt tggaacaagc catgtttgcc ctagtccagg | 2304 | |
| attgcctcac ttgagacttg ctaggcctct gctgtgtgct ggggtggcca gtgggactca | 2364 | |
| ggagagagca agctaaggag tcaccaaaaa aaaaaaaaaa aaaagggag aatttaaaag | 2424 | |
| tgtacagttg tgtgtttaga tacactatag aataatgtgg tatatattgt acaaatagtc | 2484 | |
| tacagggtgt | 2494 | |

<210> SEQ ID NO 2
<211> LENGTH: 517
<212> TYPE: PRT
<213> ORGANISM: Homo sapiens

<400> SEQUENCE: 2

Met Leu Pro Pro Gly Gly Phe Pro Ala Ala Val Cys Pro Pro Gly Arg
1               5                   10                  15

```
Ala Gln Phe Gly Pro Gly Ala Gly Ser Gly Ala Gly Gly Ser
         20                  25                  30

Ser Gly Gly Gly Gly Pro Gly Thr Tyr Gln Tyr Lys Pro Gly Gly
         35                  40                  45

Ser Ala Leu Arg Ala Arg Thr Leu Glu Pro Ala Ala Ala Gly Ser Cys
         50                  55                  60

Gly Gly Leu Gly Gly Leu Gly Val Pro Gly Ser Gly Phe Arg Ala His
 65                  70                  75                  80

Val Tyr Leu Cys Asn Arg Pro Leu Trp Leu Lys Phe His Arg His Gln
                 85                  90                  95

Thr Glu Met Ile Ile Thr Lys Gln Gly Arg Arg Met Phe Pro Phe Leu
                100                 105                 110

Ser Phe Asn Ile Asn Gly Leu Asn Pro Thr Ala His Tyr Asn Val Phe
                115                 120                 125

Val Glu Val Val Leu Ala Asp Pro Asn His Trp Arg Phe Gln Gly Gly
                130                 135                 140

Lys Trp Val Thr Cys Gly Lys Ala Asp Asn Asn Met Gln Gly Asn Lys
145                 150                 155                 160

Met Tyr Val His Pro Glu Ser Pro Asn Thr Gly Ser His Trp Met Arg
                165                 170                 175

Gln Glu Ile Ser Phe Gly Lys Leu Lys Leu Thr Asn Asn Lys Gly Ala
                180                 185                 190

Asn Asn Asn Asn Thr Gln Met Ile Val Leu Gln Ser Leu His Lys Tyr
                195                 200                 205

Gln Pro Arg Leu His Ile Val Glu Val Thr Glu Asp Gly Val Glu Asp
                210                 215                 220

Leu Asn Glu Pro Ser Lys Thr Gln Thr Phe Thr Phe Ser Glu Thr Gln
225                 230                 235                 240

Phe Ile Ala Val Thr Ala Tyr Gln Asn Thr Asp Ile Thr Gln Leu Lys
                245                 250                 255

Ile Asp His Asn Pro Phe Ala Lys Gly Phe Arg Asp Asn Tyr Asp Ser
                260                 265                 270

Met Tyr Thr Ala Ser Glu Asn Asp Arg Leu Thr Pro Ser Pro Thr Asp
                275                 280                 285

Ser Pro Arg Ser His Gln Ile Val Pro Gly Gly Arg Tyr Gly Val Gln
                290                 295                 300

Ser Phe Phe Pro Glu Pro Phe Val Asn Thr Leu Pro Gln Ala Arg Tyr
305                 310                 315                 320

Tyr Asn Gly Glu Arg Thr Val Pro Gln Thr Asn Gly Leu Leu Ser Pro
                325                 330                 335

Gln Gln Ser Glu Glu Val Ala Asn Pro Pro Gln Arg Trp Leu Val Thr
                340                 345                 350

Pro Val Gln Gln Pro Gly Thr Asn Lys Leu Asp Ile Ser Ser Tyr Glu
                355                 360                 365

Ser Glu Tyr Thr Ser Ser Thr Leu Leu Pro Tyr Gly Ile Lys Ser Leu
                370                 375                 380

Pro Leu Gln Thr Ser His Ala Leu Gly Tyr Tyr Pro Asp Pro Thr Phe
385                 390                 395                 400

Pro Ala Met Ala Gly Trp Gly Gly Arg Gly Ser Tyr Gln Arg Lys Met
                405                 410                 415

Ala Ala Gly Leu Pro Trp Thr Ser Arg Thr Ser Pro Thr Val Phe Ser
                420                 425                 430
```

```
Glu Asp Gln Leu Ser Lys Glu Lys Val Lys Glu Ile Gly Ser Ser
            435                 440                 445

Trp Ile Glu Thr Pro Pro Ser Ile Lys Ser Leu Asp Ser Asn Asp Ser
        450                 455                 460

Gly Val Tyr Thr Ser Ala Cys Lys Arg Arg Leu Ser Pro Ser Asn
465                 470                 475                 480

Ser Ser Asn Glu Asn Ser Pro Ser Ile Lys Cys Glu Asp Ile Asn Ala
                485                 490                 495

Glu Glu Tyr Ser Lys Asp Thr Ser Lys Gly Met Gly Gly Tyr Tyr Ala
            500                 505                 510

Phe Tyr Thr Thr Pro
        515

<210> SEQ ID NO 3
<211> LENGTH: 21
<212> TYPE: DNA
<213> ORGANISM: Homo sapiens

<400> SEQUENCE: 3
aagatactag gcccaggagt c                                              21

<210> SEQ ID NO 4
<211> LENGTH: 18
<212> TYPE: DNA
<213> ORGANISM: Homo sapiens

<400> SEQUENCE: 4
tcctgagtcc cactggcc                                                  18

<210> SEQ ID NO 5
<211> LENGTH: 1529
<212> TYPE: DNA
<213> ORGANISM: Homo sapiens
<220> FEATURE:
<221> NAME/KEY: CDS
<222> LOCATION: (3)..(749)

<400> SEQUENCE: 5 ac aac tat gat tcc atg tac acc gct tca gaa aat gac agg tta act       47
   Asn Tyr Asp Ser Met Tyr Thr Ala Ser Glu Asn Asp Arg Leu Thr
    1               5                  10                  15 cca tct ccc acg gat tct cct aga tcc cat cag att gtc cct gga ggt      95
Pro Ser Pro Thr Asp Ser Pro Arg Ser His Gln Ile Val Pro Gly Gly
                20                  25                  30 cgg tac ggc gtt caa tcc ttc ttc ccg gag ccc ttt gtc aac act tta     143
Arg Tyr Gly Val Gln Ser Phe Phe Pro Glu Pro Phe Val Asn Thr Leu
            35                  40                  45 cct caa gcc cgc tat tat aat ggc gag aga acc gtg cca cag acc aac     191
Pro Gln Ala Arg Tyr Tyr Asn Gly Glu Arg Thr Val Pro Gln Thr Asn
        50                  55                  60 ggc ctc ctt tca ccc caa cag agc gaa gag gtg gcc aac cct ccc cag     239
Gly Leu Leu Ser Pro Gln Gln Ser Glu Glu Val Ala Asn Pro Pro Gln
 65                  70                  75 cgg tgg ctt gtc acg cct gtc cag caa cct ggg acc aac aaa cta gac     287
Arg Trp Leu Val Thr Pro Val Gln Gln Pro Gly Thr Asn Lys Leu Asp
 80                  85                  90                  95 atc agt tcc tat gaa tct gaa tat act tct agc aca ttg ctc cca tat     335
Ile Ser Ser Tyr Glu Ser Glu Tyr Thr Ser Ser Thr Leu Leu Pro Tyr
                100                 105                 110 ggc att aaa tcc ttg ccc ctt cag aca tcc cat gcc ctg ggg tat tac     383
Gly Ile Lys Ser Leu Pro Leu Gln Thr Ser His Ala Leu Gly Tyr Tyr
```

-continued

```
                   115                 120                 125
cca gac cca acc ttt cct gca atg gca ggg tgg gga ggt cga ggt tct      431
Pro Asp Pro Thr Phe Pro Ala Met Ala Gly Trp Gly Gly Arg Gly Ser
        130                 135                 140 tac cag agg aag atg gca gct gga cta cca tgg acc tcc aga aca agc      479
Tyr Gln Arg Lys Met Ala Ala Gly Leu Pro Trp Thr Ser Arg Thr Ser
145                 150                 155 ccc act gtg ttc tct gaa gat cag ctc tcc aag gag aaa gtg aaa gag      527
Pro Thr Val Phe Ser Glu Asp Gln Leu Ser Lys Glu Lys Val Lys Glu
160                 165                 170                 175 gaa att ggc tct tct tgg ata gag aca ccc cct tcc atc aaa tct cta      575
Glu Ile Gly Ser Ser Trp Ile Glu Thr Pro Pro Ser Ile Lys Ser Leu
                180                 185                 190 gat tcc aat gat tca gga gta tac acc agt gct tgt aag cga agg cgg      623
Asp Ser Asn Asp Ser Gly Val Tyr Thr Ser Ala Cys Lys Arg Arg Arg
                195                 200                 205 ctg tct cct agc aac tcc agt aat gaa aat tca ccc tcc ata aag tgt      671
Leu Ser Pro Ser Asn Ser Ser Asn Glu Asn Ser Pro Ser Ile Lys Cys
        210                 215                 220 gag gac att aat gct gaa gag tat agt aaa gac acc tca aaa ggc atg      719
Glu Asp Ile Asn Ala Glu Glu Tyr Ser Lys Asp Thr Ser Lys Gly Met
225                 230                 235 gga ggg tat tat gct ttt tac aca act ccc taaagagtta ttttaacctc        769
Gly Gly Tyr Tyr Ala Phe Tyr Thr Thr Pro
240                 245 aaaaattagc taacttttg cagatggact tggtggtgtt ttttgttgtc ttctttgcct    829
aggttgccaa aaagatgttt gccttccacc ttgatgcatc ctgttttgtg caattctcta    889
aaagaaggtg ccaaagcttt tgattgctg caggtaacta aaacaaacct agcatttttw     949
aaaaattarg attaatggaa gcctttaagg attttaaatt cgaagggatc caaggttctg   1009
tatttatctt attggggaga cactaacmmt tcaaagaagc aggctgtgaa cattgggtgc   1069
ccagtgctat cagatgagtt aaaacctttg attctcattt ctatttgtaa attcttaagc   1129
aaatagaagc cgagtgttaa ggtgttttgc ttctgaaaga gggctgtgcc ttccgtttca   1189
gaaggagaca ttttgctgtt acattctgcc aggggcaaaa gatactaggc ccaggagtca   1249
agaaaagctt ttgtgaaagt gatagtttca cctgactttg attccttaac ccccggcttt   1309
tggaacaagc catgtttgcc ctagtccagg attgcctcac ttgagacttg ctaggcctct   1369
gctgtgtgct ggggtggcca gtgggactca ggagagagca agctaaggag tcaccaaaaa   1429
aaaaaaaaaa aaaagggag aatttaaaag tgtacagttg tgtgtttaga tacactatag    1489
aataatgtgg tatatattgt acaaatagtc tacagggtgt                          1529
```

<210> SEQ ID NO 6
<211> LENGTH: 249
<212> TYPE: PRT
<213> ORGANISM: Homo sapiens

<400> SEQUENCE: 6

```
Asn Tyr Asp Ser Met Tyr Thr Ala Ser Glu Asn Asp Arg Leu Thr Pro
 1               5                  10                  15

Ser Pro Thr Asp Ser Pro Arg Ser His Gln Ile Val Pro Gly Gly Arg
                20                  25                  30

Tyr Gly Val Gln Ser Phe Phe Pro Glu Pro Phe Val Asn Thr Leu Pro
            35                  40                  45

Gln Ala Arg Tyr Tyr Asn Gly Glu Arg Thr Val Pro Gln Thr Asn Gly
        50                  55                  60
```

```
Leu Leu Ser Pro Gln Gln Ser Glu Glu Val Ala Asn Pro Pro Gln Arg
 65                  70                  75                  80

Trp Leu Val Thr Pro Val Gln Gln Pro Gly Thr Asn Lys Leu Asp Ile
                 85                  90                  95

Ser Ser Tyr Glu Ser Glu Tyr Thr Ser Thr Leu Leu Pro Tyr Gly
            100                 105                 110

Ile Lys Ser Leu Pro Leu Gln Thr Ser His Ala Leu Gly Tyr Tyr Pro
        115                 120                 125

Asp Pro Thr Phe Pro Ala Met Ala Gly Trp Gly Arg Gly Ser Tyr
    130                 135                 140

Gln Arg Lys Met Ala Ala Gly Leu Pro Trp Thr Ser Arg Thr Ser Pro
145                 150                 155                 160

Thr Val Phe Ser Glu Asp Gln Leu Ser Lys Glu Lys Val Lys Glu Glu
                165                 170                 175

Ile Gly Ser Ser Trp Ile Glu Thr Pro Pro Ser Ile Lys Ser Leu Asp
            180                 185                 190

Ser Asn Asp Ser Gly Val Tyr Thr Ser Ala Cys Lys Arg Arg Arg Leu
    195                 200                 205

Ser Pro Ser Asn Ser Ser Asn Glu Asn Ser Pro Ser Ile Lys Cys Glu
    210                 215                 220

Asp Ile Asn Ala Glu Glu Tyr Ser Lys Asp Thr Ser Lys Gly Met Gly
225                 230                 235                 240

Gly Tyr Tyr Ala Phe Tyr Thr Thr Pro
                245

<210> SEQ ID NO 7
<211> LENGTH: 24
<212> TYPE: DNA
<213> ORGANISM: Homo sapiens

<400> SEQUENCE: 7
aaaaacacca ccaagtccat ctgc                                             24

<210> SEQ ID NO 8
<211> LENGTH: 24
<212> TYPE: DNA
<213> ORGANISM: Homo sapiens

<400> SEQUENCE: 8
gcatcaaggt ggaaggcaaa catc                                             24

<210> SEQ ID NO 9
<211> LENGTH: 24
<212> TYPE: PRT
<213> ORGANISM: Artificial Sequence
<220> FEATURE:
<223> OTHER INFORMATION: Xaas at postitions 3, 7 and 19 may be any amino
      acid
<220> FEATURE:
<223> OTHER INFORMATION: Any on of the Xaas at postions 4 through 5 may
      be absent - intended to indicate a range of 1-2 amino acids
<220> FEATURE:
<223> OTHER INFORMATION: Xaa at postion 6 may be either Phe or Cys
<220> FEATURE:
<223> OTHER INFORMATION: Any one of the Xaas at postions 8 through 11
      may be absent - intended to indicate a range of 3-4
      amino acids
<220> FEATURE:
<223> OTHER INFORMATION: Xaa at postion 12 may be Asn or Thr
<220> FEATURE:
<223> OTHER INFORMATION: Xaa at postion 15 may be Leu, Ile or Val
<220> FEATURE:
```

```
<223> OTHER INFORMATION: Any on of the Xaas at positions 16 through 17
      may be absent - intended to indicate a range of 1-2
      amino acids
<220> FEATURE:
<223> OTHER INFORMATION: Any one of the Xaas at postions 20 through 21
      may be absent - intended to indicate a range of 1-2
      amino acids
<220> FEATURE:
<223> OTHER INFORMATION: Xaa at postion 23 may be Arg or Gly
<220> FEATURE:
<223> OTHER INFORMATION: Xaa at postion 24 may be Lys, Arg or Gln
<220> FEATURE:
<223> OTHER INFORMATION: Description of Artificial Sequence: T-box
      consensus sequence

<400> SEQUENCE: 9

Leu Trp Xaa Xaa Xaa Xaa Xaa Xaa Xaa Xaa Xaa Xaa Glu Met Xaa Xaa
 1               5                  10                  15

Xaa Thr Xaa Xaa Xaa Gly Xaa Xaa
            20

<210> SEQ ID NO 10
<211> LENGTH: 22
<212> TYPE: PRT
<213> ORGANISM: Artificial Sequence
<220> FEATURE:
<223> OTHER INFORMATION: Xaas at postions 6,11,16, and 21 may be any
      amino acid
<220> FEATURE:
<223> OTHER INFORMATION: Xaa at postion 1 may be Leu, Ile, Val, Met, Tyr
      or Trp
<220> FEATURE:
<223> OTHER INFORMATION: Xaa at postion 3 may be Phe, Ala, Asp or His
<220> FEATURE:
<223> OTHER INFORMATION: Xaa at postion 4 may be Asp, Glu or Asn
<220> FEATURE:
<223> OTHER INFORMATION: Xaa at postion 5 may be Glu or Ser
<220> FEATURE:
<223> OTHER INFORMATION: Any one or two of the Xaas at postions 7
      through 9 may be absent - intended to indicate a range of
      1-3 amino acids
<220> FEATURE:
<223> OTHER INFORMATION: Any on of the Xaas at postions 12 through 13
      may be absent - intended to indicate a range of 1-2 amino acids
<220> FEATURE:
<223> OTHER INFORMATION: Any one or two of the Xaas at postions 17
      through 19 may be absent - intended to indicate a range of
      1-3 amino acids
<220> FEATURE:
<223> OTHER INFORMATION: Xaa at postion 20 may be Ile, Val or Ala
<220> FEATURE:
<223> OTHER INFORMATION: Description of Artificial Sequence: T-box
      consensus sequence

<400> SEQUENCE: 10

Xaa His Xaa Xaa Xaa Xaa Xaa Xaa Xaa Gly Xaa Xaa Xaa Trp Met Xaa
 1               5                  10                  15

Xaa Xaa Xaa Xaa Xaa Phe
            20
```